(12) United States Patent
Haketa et al.

(10) Patent No.: US 12,069,943 B2
(45) Date of Patent: Aug. 20, 2024

(54) COMPOUND, MATERIAL FOR ORGANIC ELECTROLUMINESCENT ELEMENTS, ORGANIC ELECTROLUMINESCENT ELEMENT, AND ELECTRONIC DEVICE

(71) Applicant: IDEMITSU KOSAN CO., LTD., Chiyoda-ku (JP)

(72) Inventors: Tasuku Haketa, Chiyoda-ku (JP); Hirokatsu Ito, Sodegaura (JP); Yu Kudo, Sodegaura (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 576 days.

(21) Appl. No.: 17/298,363

(22) PCT Filed: Dec. 3, 2019

(86) PCT No.: PCT/JP2019/047140
§ 371 (c)(1),
(2) Date: May 28, 2021

(87) PCT Pub. No.: WO2020/116418
PCT Pub. Date: Jun. 11, 2020

(65) Prior Publication Data
US 2022/0045272 A1    Feb. 10, 2022

(30) Foreign Application Priority Data
Dec. 3, 2018 (JP) .................. 2018-226815

(51) Int. Cl.
*H10K 50/11* (2023.01)
*C07C 211/54* (2006.01)
(Continued)

(52) U.S. Cl.
CPC .......... *H10K 85/633* (2023.02); *C07C 211/54* (2013.01); *C07D 307/91* (2013.01);
(Continued)

(58) Field of Classification Search
None
See application file for complete search history.

(56) References Cited

U.S. PATENT DOCUMENTS

| 2012/0217492 A1 | 8/2012 | Kim et al. |
| 2017/0077412 A1 | 3/2017 | Lim et al. |

(Continued)

FOREIGN PATENT DOCUMENTS

| CN | 105408310 A | 3/2016 |
| CN | 105531278 A | 4/2016 |

(Continued)

OTHER PUBLICATIONS

International Search Report issued Feb. 18, 2020 in PCT/JP2019/047140 filed Dec. 3, 2019, 3 pages.
(Continued)

*Primary Examiner* — Robert S Loewe
(74) *Attorney, Agent, or Firm* — Oblon, McClelland, Maier & Neustadt, L.L.P.

(57) ABSTRACT

The present invention relates to a compound represented by the formula (1):

(Continued)

wherein $R^1$ to $R^4$ and $L^1$ to $L^4$ are those defined in the specification, and Ar is the following formula (A) or (B):

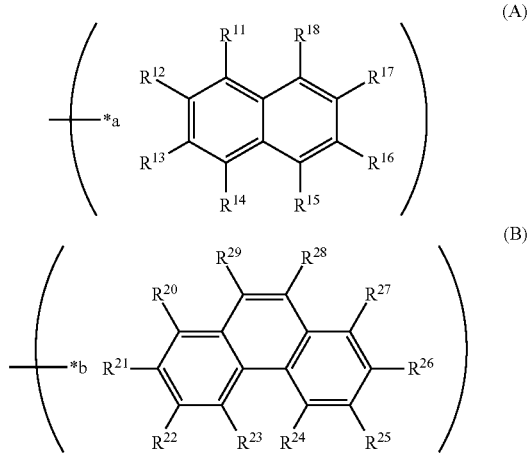

wherein $R^{11}$ to $R^{18}$ and $R^{20}$ to $R^{29}$ are those defined in the specification, and Ar is one defined in the specification.

27 Claims, 1 Drawing Sheet

(51) Int. Cl.
    *C07D 307/91*     (2006.01)
    *C07D 405/12*     (2006.01)
    *C09K 11/06*     (2006.01)
    *H10K 85/60*     (2023.01)
    *H10K 50/15*     (2023.01)

(52) U.S. Cl.
    CPC ............ *C07D 405/12* (2013.01); *C09K 11/06* (2013.01); *H10K 85/636* (2023.02); *C07B 2200/05* (2013.01); *C07C 2603/26* (2017.05); *C09K 2211/1007* (2013.01); *C09K 2211/1011* (2013.01); *C09K 2211/1014* (2013.01); *C09K 2211/1018* (2013.01); *H10K 50/11* (2023.02); *H10K 50/156* (2023.02); *H10K 85/615* (2023.02); *H10K 85/6574* (2023.02); *H10K 85/6576* (2023.02)

(56) References Cited

U.S. PATENT DOCUMENTS

| | | | |
|---|---|---|---|
| 2018/0072695 A1 | 3/2018 | Byun et al. | |
| 2018/0123048 A1* | 5/2018 | So | ........................ C07D 409/10 |
| 2019/0189927 A1 | 6/2019 | Lee et al. | |
| 2020/0044161 A1* | 2/2020 | Han | ........................ C07D 307/91 |
| 2022/0093870 A1 | 3/2022 | Mun. et al. | |

FOREIGN PATENT DOCUMENTS

| | | |
|---|---|---|
| CN | 107406402 A | 11/2017 |
| CN | 107531684 A | 1/2018 |
| CN | 108101898 A | 6/2018 |
| JP | 2017-197482 A | 11/2017 |
| KR | 10-2012-0097320 A | 9/2012 |
| KR | 10-2013-0059513 A | 6/2013 |
| KR | 10-1373587 B1 | 3/2014 |
| KR | 10-2015-0072768 A | 6/2015 |
| KR | 10-2016-0059609 A | 5/2016 |
| KR | 10-2018-0011429 A | 2/2018 |
| KR | 10-2018-0019880 A | 2/2018 |
| WO | WO 2016/072690 A1 | 5/2016 |
| WO | WO 2017/204556 A1 | 11/2017 |
| WO | WO 2018/012780 A1 | 1/2018 |
| WO | WO 2018/021737 A1 | 2/2018 |

OTHER PUBLICATIONS

Combined Chinese Office Action and Search Report issued Dec. 1, 2023 in Chinese Patent Application No. 201980079977.8 (with unedited computer-generated English translation), 21 pages.
Official communication issued in CN application 201980079977.8 on May 11, 2024, (with English language translation).

* cited by examiner

COMPOUND, MATERIAL FOR ORGANIC ELECTROLUMINESCENT ELEMENTS, ORGANIC ELECTROLUMINESCENT ELEMENT, AND ELECTRONIC DEVICE

TECHNICAL FIELD

The present invention relates to a compound, a material for organic electroluminescent devices using the compound, an organic electroluminescent device containing the compound, and an electronic device including the organic luminescent device.

BACKGROUND ART

In general, an organic electroluminescent device (organic EL device) includes an anode, a cathode, and an organic layer sandwiched between the anode and the cathode. When a voltage is applied between the both electrodes, electrons from the cathode side, and holes from the anode side are injected into a light emitting region. The injected electrons and holes are recombined in the light emitting region to generate an excited state. On the occasion when the excited state returns to a ground state, light is emitted. In consequence, development of a compound which efficiently transports electrons or holes into a light emitting region, and promotes recombination of the electrons with the holes is important in obtaining a high-performance organic EL device. In addition, in recent years, for more diffusion of smartphones, organic EL televisions, organic EL lightings, and the like using an organic EL device, any compound satisfying a sufficient device lifetime is required.

PTL 1 describes compounds in which a triphenylene group is bonded to a benzene ring of a metaphenylenediamine skeleton (Compounds 2 to 20).

PTL 2 describes a compound in which a 4-dibenzofuranyl group is bonded to a benzene ring of a metaphenylenediamine skeleton; a compound in which a 4-dibenzpthiophenyl group is bonded to a benzene ring of a metaphenylenediamine skeleton; and a compound in which a phenyl group is bonded to a benzene ring of a metaphenylenediamine skeleton (see pages 12 to 13).

PTL 3 describes a compound in which a 7-(2-cyano) phenanthryl group is bonded to a benzene ring of a metaphenylenediamine skeleton (T-35).

PTL 4 describes a compound in which a 4-(9-carbazolyl) phenyl group is bonded to a benzene ring of a metaphenylenediamine skeleton (1-31); a compound in which a terphenylyl group is bonded to a benzene ring of a metaphenylenediamine skeleton (2-63); and a compound in which a 2-(9-dimethyl)fluorenyl group is bonded to a benzene ring of a metaphenylenediamine skeleton (2-64).

CITATION LIST

Patent Literature

PTL 1: US 2017/0077412 A
PTL 2: KR 10 2015 0072768 A
PTL 3: JP 2017 197482 A
PTL 4: WO 2018/012780 A

SUMMARY OF INVENTION

Technical Problem

Many compounds have conventionally been reported as a material for producing organic EL devices, but there is still a demand for a compound that further improves characteristics of organic EL devices.

The present invention has been made in order to solve the aforementioned problems, and an object thereof is to provide an organic EL device with a more improved lifetime and a novel compound capable of realizing such an organic EL device.

Solution to Problem

In order to achieve the aforementioned object, the present inventors made extensive and intensive investigations. As a result, it has been found that a metaphenylenediamine compound in which a naphthyl group or a phenanthryl group is bonded to a benzene ring of a metaphenylenediamine skeleton provides an organic EL device with a more improved lifetime.

In one aspect, the present invention provides a compound represented by the formula (1) (hereinafter occasionally referred to as "compound (1)").

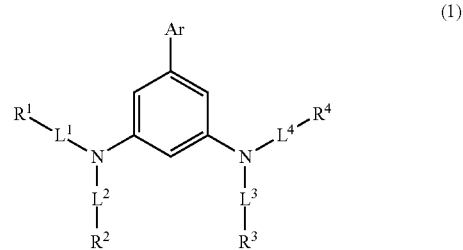

In the formula,
$R^1$ to $R^4$ are each independently selected from the group consisting of a substituted or unsubstituted aryl group having 6 to 30 ring carbon atoms and a substituted or unsubstituted heteroaryl group having 5 to 30 ring atoms.
$L^1$ to $L^4$ are each independently selected from the group consisting of a single bond and a substituted or unsubstituted arylene group having 6 to 30 ring carbon atoms.
$R^1$ or $L^1$ does not bond to $R^2$ or $L^2$ to form a ring structure, and $R^3$ or $L^3$ does not bond to $R^4$ or $L^4$ to form a ring structure. $R^1$ does not bond to $R^3$ to form a ring structure, $R^1$ does not bond to $R^4$ to form a ring structure, $R^2$ does not bond to $R^3$ to form a ring structure, and $R^2$ does not bond to $R^4$ to form a ring structure.
Ar is the following formula (A) or (B).

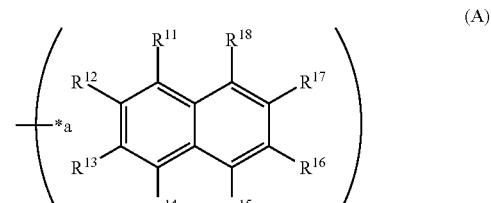

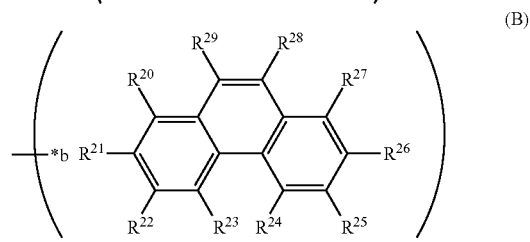

In the formulae (A) and (B), $R^{11}$ to $R^{18}$ and $R^{20}$ to $R^{29}$ are each independently a hydrogen atom or a substituent, and the substituent is selected from the group consisting of a halogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted aralkyl group having 7 to 36 carbon atoms, a substituted or unsubstituted alkoxy group having 1 to 30 carbon atoms, a substituted or unsubstituted aryloxy group having 6 to 30 ring carbon atoms, a mono-, di-, or tri substituted silyl group having a substituent selected from a substituted or unsubstituted alkyl group having 1 to 30 carbon atoms and a substituted or unsubstituted aryl group having 6 to 30 ring carbon atoms, and a substituted or unsubstituted heteroaryl group having 5 to 30 ring atoms.

Adjacent two selected from $R^{11}$ to $R^{18}$ do not form a ring structure, and adjacent two selected from $R^{20}$ to $R^{29}$ do not form a ring structure.

However, one selected from $R^{11}$ to $R^{18}$ is a single bond bonding to *a, and one selected from $R^{20}$ to $R^{29}$ is a single bond bonding to *b.

Ar does not bond to a benzene ring bonding to Ar to form a ring structure.

In another aspect, the present invention provides a material for organic electroluminescent devices including the compound (1).

In a further aspect, the present invention provides an organic electroluminescent device including a cathode, an anode, and organic layers between the cathode and the anode, wherein the organic layers include a light emitting layer, and at least one layer of the organic layers contains a compound (1).

In a still further aspect, the present invention provides an electronic device including the organic electroluminescent device.

Advantageous Effects of Invention

The compound (1) provides an organic EL device with a more improved lifetime.

DESCRIPTION OF EMBODIMENTS

Figure 1:
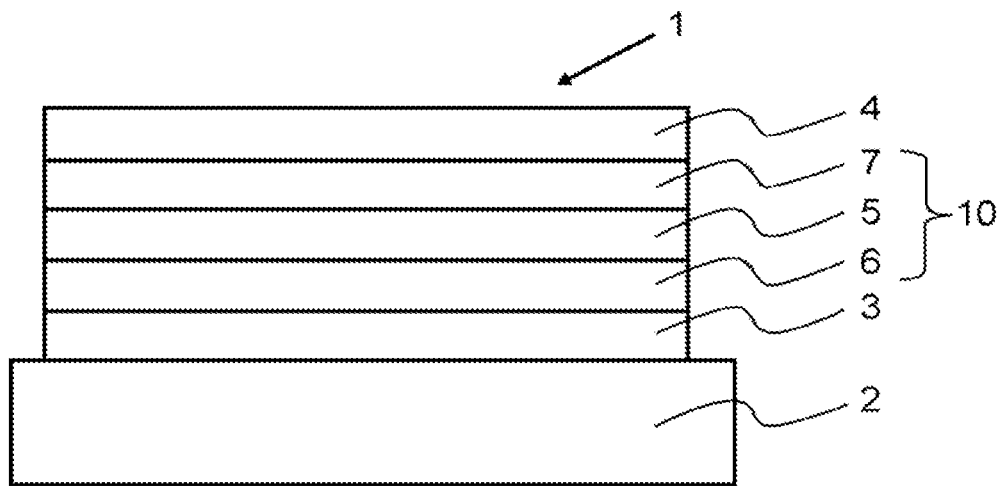
FIG. 1 is a schematic view illustrating an example of a layer configuration of an organic EL device according to an embodiment of the present invention.

In this specification, the term of "XX to YY carbon atoms" referred to by "a substituted or unsubstituted group ZZ having XX to YY carbon atoms" indicates the number of carbon atoms of the unsubstituted group ZZ, and does not include any carbon atom in the substituent of the substituted group ZZ.

In this specification, the term of "XX to YY atoms" referred to by "a substituted or unsubstituted group ZZ having XX to YY atoms" indicates the number of atoms of the unsubstituted group ZZ, and does not include any atom in the substituent of the substituted group ZZ.

In this specification, the "unsubstituted group ZZ" in the case of the "substituted or unsubstituted group ZZ" indicates that a hydrogen atom in the group ZZ is not substituted with a substituent.

In this specification, the "hydrogen atom" includes isotopes having different numbers of neutrons, that is, protium, deuterium, and tritium.

The number of "ring carbon atoms" referred to in this specification indicates the number of carbon atoms among the atoms forming the ring itself of a compound with a structure in which the atoms are cyclically bonded (for example, a monocyclic compound, a fused ring compound, a cross-linked compound, a carbocyclic compound, and a heterocyclic compound). If the ring is substituted with a substituent, the carbon atom included in the substituent is not included in the ring carbon atom. The same applies to the number of "ring carbon atoms" described below unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. Also, when the benzene ring or the naphthalene ring is substituted with, for example, an alkyl group as a substituent, the carbon atom in the alkyl group is not counted as the number of ring carbon atoms. Also, in a case of a fluorene ring to which, for example, a fluorene ring as a substituent is bonded (inclusive of a spirofluorene ring), the carbon atom in the fluorene ring as the substituent is not counted as the number of ring carbon atoms.

The number of "ring atoms" referred to in this specification indicates the number of atoms forming the ring itself of a compound (for example, a monocyclic compound, a fused ring compound, a cross-linked compound, a carbocyclic compound, and a heterocyclic compound) with a structure in which the atoms are cyclically bonded (for example, a monocyclic ring, a fused ring, a ring assembly). The atom not forming the ring (for example, a hydrogen atom that terminates a bond of atoms forming the ring), and the atom included in a substituent if the ring is substituted with the substituent, are not counted as the number of ring atoms. The same applies to the number of "ring atoms" described below unless otherwise noted. For example, a pyridine ring has 6 ring atoms, a quinazoline ring has 10 ring atoms, and a furan ring has 5 ring atoms. The hydrogen atom bonded to each ring carbon atom in the pyridine ring or the quinazoline ring, and the atom constituting a substituent, are not counted as the number of ring atoms. Also, in a case of a fluorene ring to which, for example, a fluorene ring as a substituent is bonded (inclusive of a spirobifluorene ring), the atom in the fluorene ring as the substituent is not counted as the number of ring atoms.

In this specification, the "aryl group" is a monovalent residue of an aromatic hydrocarbon and does not include a heteroaryl group. The "arylene group" is a divalent residue of an aromatic hydrocarbon and does not include a heteroarylene group.

The compound (1) according to one embodiment of the present invention is represented by the formula (1).

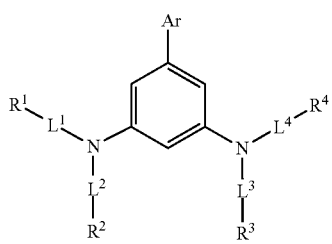

(1)

R¹ to R⁴ are each independently selected from the group consisting of a substituted or unsubstituted aryl group having 6 to 30, preferably 6 to 25, and more preferably 6 to 18 ring carbon atoms; and a substituted or unsubstituted heteroaryl group having 5 to 30, preferably 5 to 24, and more preferably 5 to 13 ring atoms.

In the substituted or unsubstituted aryl group having 6 to 30 ring carbon atoms, the aryl group having 6 to 30 ring carbon atoms is, for example, a phenyl group, a biphenylyl group, a terphenylyl group, a biphenylenyl group, a naphthyl group, an anthryl group, a benzoanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, or a triphenylenyl group; preferably a phenyl group, a biphenylyl group, a terphenylyl group, or a fluorenyl group; more preferably a p-, o-, or m-biphenylyl group, a 1,1':4',1''-terphenyl-4-yl group, a 1,1':3',1''-terphenyl-4-yl group, a 1,1':3',1''-terphenyl-2-yl group, or a 1-, 2-, 3-, or 4-fluorenyl group; and still more preferably a p-biphenylyl group, a 1,1':4',1''-terphenyl-4-yl group, a 1,1':3',1''-terphenyl-4-yl group, a 1,1':3',1''-terphenyl-2-yl group, a 2-fluorenyl group, or a 4-fluorenyl group.

The 9,9-positions of the fluorenyl group are preferably substituted with a group selected from the group consisting of a substituted or unsubstituted alkyl group having 1 to 30 carbon atoms and a substituted or unsubstituted aryl group having 1 to 30 carbon atoms, and more preferably substituted with, for example, a methyl group or a phenyl group. The 9,9-positions of the fluorenyl group may be the same as or different from each other, and for example, both of the 9,9-positions may be an alkyl group, both of them may be aryl group, or one of them may be an alkyl group, whereas the other may be an aryl group.

The aryl group having 6 to 30 ring carbon atoms includes isomer groups if present.

In the substituted or unsubstituted heteroaryl having 5 to 30 ring atoms, the heteroaryl group having 5 to 30 ring atoms contains 1 to 5, preferably 1 to 3, and more preferably 1 to 2 ring hetero atoms. The ring hetero atom is selected from, for example, a nitrogen atom, a sulfur atom, and an oxygen atom. The free valency of the heteroaryl group is present on a ring carbon atom, or is present on a ring nitrogen atom if possible.

The heteroaryl group having 5 to 30 ring atoms is, for example, a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzoisoxazolyl group, a benzisothiazolyl group, a phenanthridinyl group, an acridinyl group, a phenanthrolinyl group, a phenazinyl group, a phenothiazinyl group, a phenoxazinyl group, a xanthenyl group, a benzofuranyl group, an isobenzofuranyl group, a naphthobenzofuranyl group, a dibenzofuranyl group, a benzothiophenyl group (a benzothienyl group, hereinafter the same), an isobenzothiophenyl group (an isobenzothienyl group, hereinafter the same), a naphthobenzothiophenyl group (a naphthobenzothienyl group, hereinafter the same), a dibenzothiophenyl group (a dibenzothienyl group, hereinafter the same), or a carbazolyl group.

A dibenzofuranyl group, a benzothiophenyl group, or a carbazolyl group is preferred; a 2- or 3-dibenzofuranyl group, a 2- or 3-dibenzothiophenyl group, or a 2- or 3-carbazolyl group is more preferred; 2-dibenzofuranyl group, a 2-dibenzothiophenyl group, or a 2-carbazolyl group is still more preferred.

The N atom of the carbazolyl group is preferably substituted with a group selected from substituted or unsubstituted aryl groups having 1 to 30 carbon atoms, and is more preferably substituted with a phenyl group, a biphenyl group, a naphthyl group, or a phenanthryl group.

The substituted or unsubstituted heteroaryl group having 5 to 30 ring atoms includes isomer groups if present.

In one embodiment of the present invention, R¹ to R⁴ are preferably unsubstituted.

L¹ to L⁴ are each independently selected from the group consisting of a single bond and a substituted or unsubstituted arylene group having 6 to 30, preferably 6 to 25, and more preferably 6 to 18 ring carbon atoms.

In the substituted or unsubstituted arylene group having 6 to 30 ring carbon atoms, which is represented by L¹ to L⁴, the arylene group having 6 to 30 ring carbon atoms is, for example, a phenylene group, a biphenylene group, a terphenylene group, a biphenylenylene group, a naphthylene group, an anthrylene group, a benzoanthrylene group, a phenanthrylene group, a benzophenanthrylene group, a phenalenylene group, a picenylene group, a pentaphenylene group, a pyrenylene group, a chrysenylene group, a benzochrysenylene group, a fluorenylene group, a fluoranthenylene group, a perylenylene group, or a triphenylenylene group; preferably a phenylene group, a biphenylene group, or a naphthylene group; more preferably a 1,4-phenylene group, a 1,3-phenylene group, or a 1,2-phenylene group; and still more preferably a 1,4-phenylene group.

The arylene group having 6 to 30 ring carbon atoms includes isomer groups if present.

In one embodiment of the present invention, L¹ to L⁴ are preferably a single bond.

R¹ or L¹ does not bond to R² or L² to form a ring structure, and R³ or L³ does not bond to R⁴ or L⁴ to form a ring structure. That is, R¹ and R², R¹ and L², L¹ and R², and L¹ and L² do not bond to form a ring structure, and R³ and R⁴, R³ and L⁴, L³ and R⁴, and L³ and L⁴ do not bond to form a ring structure. In addition, R¹ does not bond to R³ to form a ring structure; R¹ does not bond to R⁴ to form a ring structure; R² does not bond to R³ to form a ring structure; and R² does not bond to R⁴ to form a ring structure.

Ar is the following formula (A) or (B).

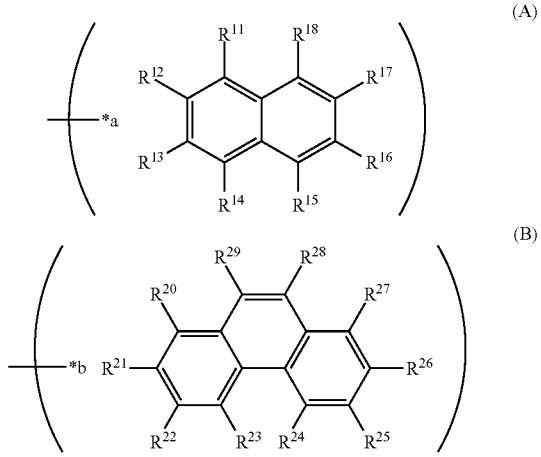

In the formula (A) and the formula (B), $R^{11}$ to $R^{18}$ and $R^{20}$ to $R^{29}$ are each independently a hydrogen atom or a substituent, and the substituent is selected from the group consisting of a halogen atom; a substituted or unsubstituted alkyl group having 1 to 30, preferably 1 to 18, and more preferably 1 to 8 carbon atoms; a substituted or unsubstituted cycloalkyl group having 3 to 30, preferably 3 to 10, more preferably 3 to 8, and still more preferably 5 or 6 ring carbon atoms; a substituted or unsubstituted aryl group having 6 to 30, preferably 6 to 25, and more preferably 6 to 18 ring carbon atoms; a substituted or unsubstituted aralkyl group having 7 to 36, preferably 7 to 26, and more preferably 7 to 20 carbon atoms; a substituted or unsubstituted alkoxy group having 1 to 30, preferably 1 to 18, and more preferably 1 to 8 carbon atoms; a substituted or unsubstituted aryloxy group having 6 to 30, preferably 6 to 25, and more preferably 6 to 18 ring carbon atoms; a mono-, di-, or tri-substituted silyl group having a substituent selected from a substituted or unsubstituted alkyl group having 1 to 30, preferably 1 to 18, and more preferably 1 to 8 carbon atoms and a substituted or unsubstituted aryl group having 6 to 30, preferably 6 to 25, and more preferably 6 to 18 ring carbon atoms; and a substituted or unsubstituted heteroaryl group having 5 to 30, preferably 5 to 24, and more preferably 5 to 13 ring atoms.

The substituent represented by $R^{11}$ to $R^{18}$ and $R^{20}$ to $R^{29}$ is preferably selected from the group consisting of a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a mono-, di-, or tri-substituted silyl group having a substituent selected from a substituted or unsubstituted alkyl group having 1 to 30 carbon atoms and a substituted or unsubstituted aryl group having 6 to 30 ring carbon atoms, and a substituted or unsubstituted heteroaryl group having 5 to 30 ring atoms; more preferably selected from the group consisting of a substituted or unsubstituted alkyl group having 1 to 30 carbon atoms, a substituted or unsubstituted aryl group having 6 to 30 ring carbon atoms, and a substituted or unsubstituted heteroaryl group having 5 to 30 ring atoms; still more preferably a substituted or unsubstituted alkyl group having 1 to 30 carbon atoms or a substituted or unsubstituted aryl group having 6 to 30 ring carbon atoms; and especially preferably a substituted or unsubstituted alkyl group having 1 to 30 carbon atoms.

The halogen atom is a fluorine atom, a chlorine atom, a bromine atom, or an iodine atom, and preferably a fluorine atom.

In the substituted or unsubstituted alkyl group having 1 to 30 carbon atoms, the alkyl group having 1 to 30 carbon atoms is, for example, a methyl group, an ethyl group, an n-propyl group, an isopropyl group, an n-butyl group, an isobutyl group, an s-butyl group, a t-butyl group, a pentyl group, a hexyl group, a heptyl group, an octyl group, a nonyl group, a decyl group, an undecyl group, or a dodecyl group; preferably a methyl group, an ethyl group, an n-propyl group, an isopropyl group, an n-butyl group, an isobutyl group, an s-butyl group, a t-butyl group, or a pentyl group; more preferably a methyl group, an ethyl group, an n-propyl group, an isopropyl group, an n-butyl group, an isobutyl group, an s-butyl group, or a t-butyl group; and still more preferably a methyl group or a t-butyl group.

The substituted or unsubstituted alkyl group having 1 to 30 carbon atoms includes isomer groups if present.

In the substituted or unsubstituted cycloalkyl group having 3 to 30 ring carbon atoms, the cycloalkyl group having 3 to 30 ring carbon atoms is, for example, a cyclopropyl group, a cyclobutyl group, a cyclopentyl group, a cyclohexyl group, or a cycloheptyl group, and preferably a cyclopentyl group or a cyclohexyl group.

The substituted or unsubstituted cycloalkyl group having 3 to 30 ring carbon atoms includes isomer groups if present.

In the substituted or unsubstituted aryl group having 6 to 30 ring carbon atoms, the aryl group having 6 to 30 ring carbon atoms is, for example, a phenyl group, a biphenylyl group, a terphenylyl group, a biphenylenyl group, a naphthyl group, an anthryl group, a benzoanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, or a triphenylenyl group, and preferably a phenyl group, a biphenylyl group, a terphenylyl group, or a naphthyl group.

The substituted aryl group having 6 to 30 ring carbon atoms is, for example, a tolyl group, a t-butylphenyl group, a 9,9-dimethylfluorenyl group, a 9,9-diphenylfluorenyl group, a 9,9'-spirobifluorenyl group, a benzo-9,9-dimethylfluorenyl group, a benzo-9,9-diphenylfluorenyl group, or a benzo-9,9'-spirobifluorenyl group.

In the substituted or unsubstituted aralkyl group having 7 to 36 carbon atoms, the aryl moiety of the aralkyl group having 7 to 36 carbon atoms is selected from the aforementioned aryl groups having 6 to 30, preferably 6 to 25, and more preferably 6 to 18 ring carbon atoms; and the alkyl moiety is selected from the aforementioned substituted or unsubstituted alkyl groups having 1 to 30, preferably 1 to 18, and more preferably 1 to 8 carbon atoms. The aralkyl group having 7 to 36 carbon atoms is, for example, a benzyl group, a phenethyl group, or a phenylpropyl group, and preferably a benzyl group.

The substituted or unsubstituted aralkyl group having 7 to 36 carbon atoms includes isomer groups if present.

In the substituted or unsubstituted alkoxy group having 1 to 30 carbon atoms, the alkyl moiety of the alkoxy group having 1 to 30 carbon atoms is selected from the aforementioned substituted or unsubstituted alkyl groups having 1 to 30, preferably 1 to 18, and more preferably 1 to 8 carbon atoms. The alkoxy group having 1 to 30 carbon atoms is, for example, a t-butoxy group, a propoxy group, an ethoxy group, or a methoxy group, preferably an ethoxy group or a methoxy group, and more preferably a methoxy group.

The substituted or unsubstituted alkoxy group having 1 to 30 carbon atoms includes isomer groups if present.

In the substituted or unsubstituted aryloxy group having 6 to 30 ring carbon atoms, the aryl moiety of the aryloxy group having 6 to 30 ring carbon atoms is selected from the aforementioned substituted or unsubstituted aryl groups having 6 to 30, preferably 6 to 25, and more preferably 6 to 18 ring carbon atoms. The aryloxy group having 6 to 30 ring carbon atoms is, for example, a terphenyloxy group, a biphenyloxy group, or a phenoxy group, preferably a biphenyloxy group or a phenoxy group, and more preferably a phenoxy group.

The substituted or unsubstituted aryloxy group having 6 to 30 carbon atoms includes isomer groups if present.

The substituent which the mono-, di-, or tri-substituted silyl group has is selected from the aforementioned substituted or unsubstituted alkyl groups having 1 to 30, preferably 1 to 18, and more preferably 1 to 8 carbon atoms, and the aforementioned substituted or unsubstituted aryl groups having 6 to 30, preferably 6 to 25, and more preferably 6 to 18 ring carbon atoms. The tri-substituted silyl group is preferred, and for example, a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, or a tritolylsilyl group is more preferred.

The mono-, di-, or tri-substituted silyl group includes isomer groups if present.

In the substituted or unsubstituted heteroaryl group having 5 to 30 ring atoms, the heteroaryl group having 5 to 30 ring atoms contains 1 to 5, preferably 1 to 3, and more preferably 1 to 2 ring hetero atoms. The ring hetero atom is selected from, for example, a nitrogen atom, a sulfur atom, and an oxygen atom. The free valency of the heteroaryl group is present on a ring carbon atom, or is present on a ring nitrogen atom if possible.

The heteroaryl group having 5 to 30 ring atoms is, for example, a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzoisoxazolyl group, a benzisothiazolyl group, a phenanthridinyl group, an acridinyl group, a phenanthrolinyl group, a phenazinyl group, a phenothiazinyl group, a phenoxazinyl group, a xanthenyl group, a benzofuranyl group, an isobenzofuranyl group, a naphthobenzofuranyl group, a dibenzofuranyl group, a benzothiophenyl group (a benzothienyl group, hereinafter the same), an isobenzothiophenyl group (an isobenzothienyl group, hereinafter the same), a naphthobenzothiophenyl group (a naphthobenzothienyl group, hereinafter the same), a dibenzothiophenyl group (a dibenzothienyl group, hereinafter the same), or a carbazolyl group.

A benzofuranyl group, an isobenzofuranyl group, a naphthobenzofuranyl group, a dibenzofuranyl group, a benzothiophenyl group, an isobenzothiophenyl group, a naphthobenzothiophenyl group, a dibenzothiophenyl group, or a carbazolyl group (a 9-carbazolyl group, or a 1-, 2-, 3-, or 4-carbazolyl group) is preferred.

The substituted heteroaryl group having 5 to 30 ring atoms is, for example, a 9-phenylcarbazolyl group, a 9-biphenylylcarbazolyl group, a 9-phenylphenylcarbazolyl group, a 9-naphthylcarbazolyl group, a phenyldibenzofuranyl group, or a phenyldibenzothiophenyl group (a phenyldibenzothienyl group, hereinafter the same).

The substituted or unsubstituted heteroaryl group having 5 to 30 ring atoms includes isomer groups if present.

Adjacent two selected from $R^{11}$ to $R^{18}$ do not form a ring structure, and adjacent two selected from $R^{20}$ to $R^{29}$ do not form a ring structure.

However, one selected from $R^{11}$ to $R^{18}$ is a single bond bonding to *a, and one selected from $R^{20}$ to $R^{29}$ is a single bond bonding to *b.

Ar does not bond to a benzene ring bonding to Ar to form a ring structure.

In one embodiment of the present invention, preferably, Ar is the formula (A), and $R^{11}$ or $R^{12}$ is a single bond bonding to *a.

In one embodiment of the present invention, preferably, $R^{11}$ to $R^{18}$ which are not a single bond bonding to *a are a hydrogen atom.

In one embodiment of the present invention, preferably, Ar is the formula (B), and one selected from $R^{20}$ to $R^{23}$ and $R^{29}$ is a single bond bonding to *b, and more preferably, $R^{29}$ is a single bond bonding to *b.

In one embodiment of the present invention, preferably $R^{20}$ to $R^{29}$ which are not a single bond bonding to *b are a hydrogen atom.

In this specification, an arbitrary substituent to be meant by the wording "substituted or unsubstituted" is, unless otherwise specifically indicated, selected from the group consisting of a halogen atom; an alkyl group having 1 to 30, preferably 1 to 18, and more preferably 1 to 8 carbon atoms; a cycloalkyl group having 3 to 30, preferably 3 to 10, more preferably 3 to 8, and still more preferably 5 or 6 ring carbon atoms; an aryl group having 6 to 30, preferably 6 to 25, and more preferably 6 to 18 ring carbon atom; an aralkyl group having 7 to 36, preferably 7 to 26, and more preferably 7 to 20 carbon atoms; an alkoxy group having 1 to 30, preferably 1 to 18, and more preferably 1 to 8 carbon atoms; an aryloxy group having 6 to 30, more preferably 6 to 25, and still more preferably 6 to 18 ring carbon atoms; a mono-, di-, or tri-substituted silyl group having a substituent selected from an alkyl group having 1 to 30, preferably 1 to 18, and more preferably 1 to 8 carbon atoms, and an aryl group having 6 to 30, preferably 6 to 25, and more preferably 6 to 18 ring carbon atoms; and a heteroaryl group having 5 to 30, preferably 5 to 24, and more preferably 5 to 13 ring atoms.

Details of the aforementioned arbitrary substituent are as follows.

The halogen atom is a fluorine atom, a chlorine atom, a bromine atom, or an iodine atom, and preferably a fluorine atom.

The alkyl group having 1 to 30 carbon atoms is, for example, a methyl group, an ethyl group, an n-propyl group, an isopropyl group, an n-butyl group, an isobutyl group, an s-butyl group, a t-butyl group, a pentyl group, a hexyl group, a heptyl group, an octyl group, a nonyl group, a decyl group, an undecyl group, or a dodecyl group; preferably a methyl group, an ethyl group, an n-propyl group, an isopropyl group, an n-butyl group, an isobutyl group, an s-butyl group, a t-butyl group, or a pentyl group; more preferably a methyl group, an ethyl group, an n-propyl group, an isopropyl group, an n-butyl group, an isobutyl group, an s-butyl group, or a t-butyl group; and still more preferably a methyl group or a t-butyl group.

The cycloalkyl group having 3 to 30 ring carbon atoms is, for example, a cyclopropyl group, a cyclobutyl group, a cyclopentyl group, a cyclohexyl group, or a cycloheptyl group, and preferably a cyclopentyl group or a cyclohexyl group.

The aryl group having 6 to 30 ring carbon atoms is, for example, a phenyl group, a biphenylyl group, a terphenylyl group, a biphenylenyl group, a naphthyl group, an anthryl group, a benzoanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, or a triphenylenyl group; preferably a phenyl group, a biphenylyl group, a terphenylyl group, or a naphthyl group; more preferably a phenyl group, a 2-, 3-, or 4-biphenylyl group, a 2-, 3-, or 4-o-terphenylyl group, a 2-, 3-, or 4-m-terphenylyl group, a 2-, 3-, or 4-p-terphenylyl group, or a 1- or 2-naphthyl group; still more preferably a phenyl group, a 2-, 3-, or 4-biphenylyl group or a 1- or 2-naphthyl group; and especially preferably a phenyl group.

The aryl moiety of the aralkyl group having 7 to 36 carbon atoms is selected from the aforementioned aryl groups having 6 to 30, preferably 6 to 25, and more preferably 6 to 18 ring carbon atoms; and the alkyl moiety is selected from the aforementioned alkyl groups having 1 to 30, preferably 1 to 18, and more preferably 1 to 8 carbon atoms. The aralkyl group having 7 to 36 carbon atoms is, for example, a benzyl group, a phenethyl group, or a phenylpropyl group, and preferably a benzyl group.

The alkyl moiety of the alkoxy group having 1 to 30 carbon atoms is selected from the aforementioned alkyl groups having 1 to 30, preferably 1 to 18, and more preferably 1 to 8 carbon atoms. The alkoxy group having 1 to 30 carbon atoms is, for example, a t-butoxy group, a propoxy group, an ethoxy group, or a methoxy group, preferably an ethoxy group or a methoxy group, and more preferably a methoxy group.

The aryl moiety of the aryloxy group having 6 to 30 ring carbon atoms is selected from the aforementioned aryl groups having 6 to 30, preferably 6 to 25, and more preferably 6 to 18 ring carbon atoms. The aryloxy group having 6 to 30 ring carbon atoms is, for example, a terphenyloxy group, a biphenyloxy group, or a phenoxy group, preferably a biphenyloxy group or a phenoxy group, and more preferably a phenoxy group.

The substituent which the mono-, di-, or tri-substituted silyl group has is selected from the aforementioned alkyl groups having 1 to 30, preferably 1 to 18, and more preferably 1 to 8 carbon atoms, and the aforementioned aryl groups having 6 to 30, preferably 6 to 25, and more preferably 6 to 18 ring carbon atoms. The tri-substituted silyl group is preferred, and for example, a trimethylsilyl group, a triethylsilyl group, a t-butyldimethylsilyl group, a propyldimethylsilyl group, an isopropyldimethylsilyl group, a triphenylsilyl group, a phenyldimethylsilyl group, a t-butyldiphenylsilyl group, or a tritolylsilyl group is more preferred.

The heteroaryl group having 5 to 30 ring atoms contains 1 to 5, preferably 1 to 3, and more preferably 1 to 2 ring hetero atoms. The ring hetero atom is selected from, for example, a nitrogen atom, a sulfur atom, and an oxygen atom. The free bond of the heteroaryl group is present on a ring carbon atom, or is present on a ring nitrogen atom if possible.

The heteroaryl group having 5 to 30 ring atoms is, for example, a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzoisoxazolyl group, a benzisothiazolyl group, a phenanthridinyl group, an acridinyl group, a phenanthrolinyl group, a phenazinyl group, a phenothiazinyl group, a phenoxazinyl group, a xanthenyl group, a benzofuranyl group, an isobenzofuranyl group, a naphthobenzofuranyl group, a dibenzofuranyl group, a benzothiophenyl group (a benzothienyl group, hereinafter the same), an isobenzothiophenyl group (an isobenzothienyl group, hereinafter the same), a naphthobenzothiophenyl group (a naphthobenzothienyl group, hereinafter the same), a dibenzothiophenyl group (a dibenzothienyl group, hereinafter the same), or a carbazolyl group.

As mentioned above, the "hydrogen atom" which is used in this specification includes a protium atom, a deuterium atom, and tritium atom. In consequence, the compound (1) may contain a naturally-derived deuterium atom.

In addition, by using a compound resulting from partially or wholly deuterating a raw material compound, the deuterium atom may be intentionally introduced into the compound (1). In consequence, in one embodiment of the present invention, the compound (1) contains at least one deuterium atom. That is, the compound (1) is a compound represented by the formula (1) or a formula of a preferred embodiment thereof and is a compound in which at least one of hydrogen atoms contained in the foregoing compound is a deuterium atom.

Furthermore, in one embodiment of the present invention, in the formula (1), at least one hydrogen atom selected from hydrogen atoms which the aryl group or heteroaryl group represented by $R^1$ to $R^4$ has, hydrogen atoms which the arylene group represented by $L^1$ to $L^4$ has, hydrogen atoms represented by $R^{11}$ to $R^{18}$ which are not a single bond bonding to *a, hydrogen atoms represented by $R^{20}$ to $R^{21}$ which are not a single bond bonding to *b, and hydrogen atoms which the benzene ring bonding to Ar has is a deuterium atom.

In one embodiment of the present invention, the compound (1) includes a deuterium atom, and in that case, a deuteration rate (a proportion of the number of deuterium atoms relative to the number of all hydrogen atoms in the compound (1)) depends upon a deuteration rate of the raw material compound to be used. Since it is typically difficult to make the deuteration rate of all of raw material compounds to be used to 100%, the deuteration rate of the compound (1) is less than 100%, preferably 95% or less, more preferably 90% or less, and still more preferably 80% or less.

In the case where the compound (1) includes deuterium, the deuteration rate (a proportion of the number of deuterium atoms relative to the number of all hydrogen atoms in the compound (1)) is 1% or more, preferably 3% or more, more preferably 5% or more, and still more preferably 10% or more.

The compound (1) may also be a mixture of a deuterated compound and a non-deuterated compound or a mixture of two or more compounds having a different deuteration rate from each other. The deuteration rate of such a mixture (a proportion of the number of deuterium atoms relative to the number of all hydrogen atoms in the compound (1)) is 1% or more, preferably 3% or more, more preferably 5% or more, and still more preferably 10% or more, and it is less than 100%, preferably 95% or less, and more preferably 90% or less.

In one embodiment of the present invention, the compound (1) includes deuterium, and at least one hydrogen atom selected from hydrogen atoms which the aryl group or the heteroaryl group represented by $R^1$ to $R^4$ has is a deuterium atom. The deuteration rate (a proportion of the number of deuterium atoms relative to the number of all hydrogen atoms which the aryl group or the heteroaryl group represented by $R^1$ to $R^4$ has) is 1% or more, preferably 3% or more, more preferably 5% or more, and still more preferably 10% or more, and it is less than 100%, preferably 95% or less, and more preferably 90% or less.

In one embodiment of the present invention, the compound (1) includes deuterium, and at least one hydrogen atom selected from hydrogen atoms which the arylene group represented by $L^1$ to $L^4$ has is a deuterium atom. The deuteration rate (a proportion of the number of deuterium atoms relative to the number of all hydrogen atoms which the arylene group represented by $L^1$ to $L^4$ has) is 1% or more, preferably 3% or more, more preferably 5% or more, and still more preferably 10% or more, and it is less than 100%, preferably 95% or less, and more preferably 90% or less.

In one embodiment of the present invention, the compound (1) includes deuterium, and at least one hydrogen atom selected from hydrogen atoms represented by $R^{11}$ to $R^{18}$ is a deuterium atom. The deuteration rate (a proportion of the number of deuterium atoms relative to the number of all hydrogen atoms represented by $R^{11}$ to $R^{18}$) is 1% or more, preferably 3% or more, more preferably 5% or more, and still more preferably 10% or more, and it is less than 100%, preferably 95% or less, and more preferably 90% or less.

In one embodiment of the present invention, the compound (1) includes deuterium, and at least one hydrogen atom selected from hydrogen atoms represented by $R^{20}$ to $R^{29}$ is a deuterium atom. The deuteration rate (a proportion of the number of deuterium atoms relative to the number of all hydrogen atoms represented by $R^{20}$ to $R^{29}$) is 1% or more, preferably 3% or more, more preferably 5% or more, and still more preferably 10% or more, and it is less than 100%, preferably 95% or less, and more preferably 90% or less.

In one embodiment of the present invention, the compound (1) includes deuterium, and at least one hydrogen atom selected from hydrogen atoms which the benzene ring bonding to Ar has is a deuterium atom. The deuteration rate (a proportion of the number of deuterium atoms relative to the number of all hydrogen atoms which the benzene ring bonding to Ar has) is 1% or more, preferably 3% or more, more preferably 5% or more, and still more preferably 10% or more, and it is less than 100%, preferably 95% or less, and more preferably 90% or less.

A method of producing the compound (1) is not particularly limited, and those skilled in the art can easily perform production by a method described in the following Examples, or by a method obtained by modifying the method with reference to a known synthesis method.

Specific examples of the compound (1) of the present invention are hereunder described, but it should be construed that the present invention is not limited thereto.

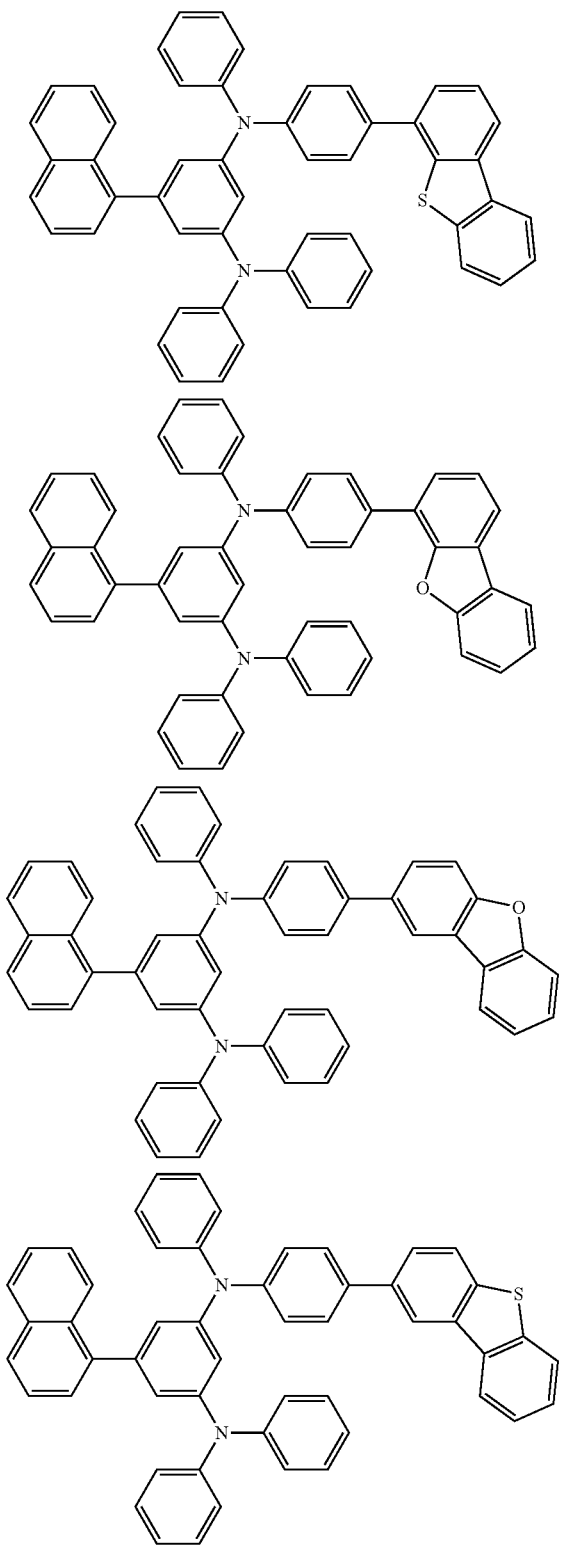

-continued
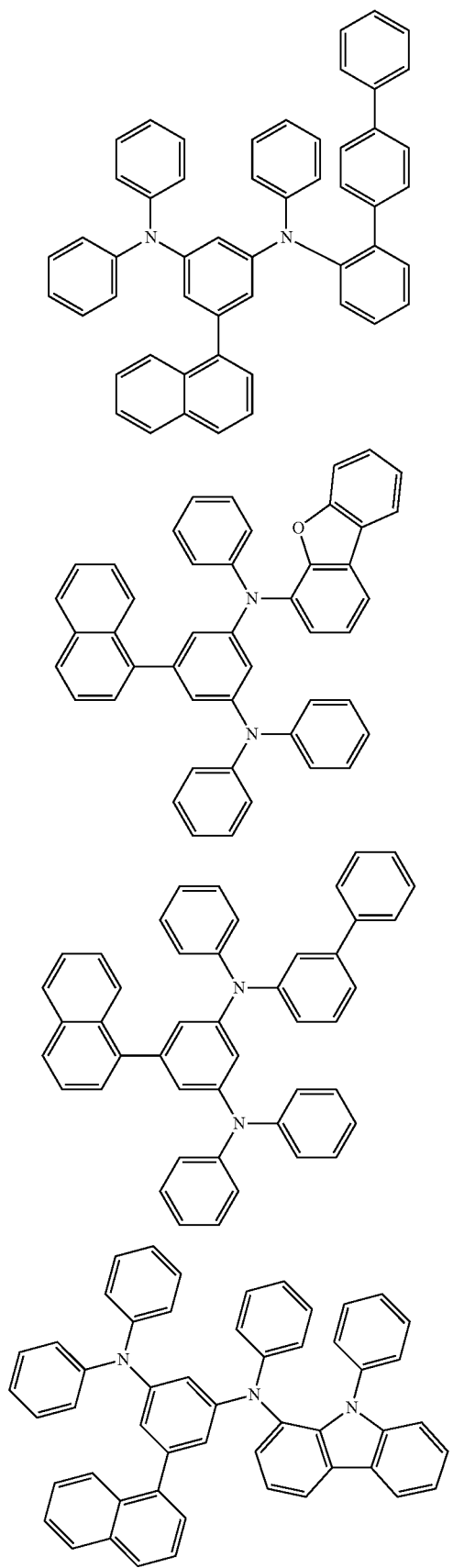
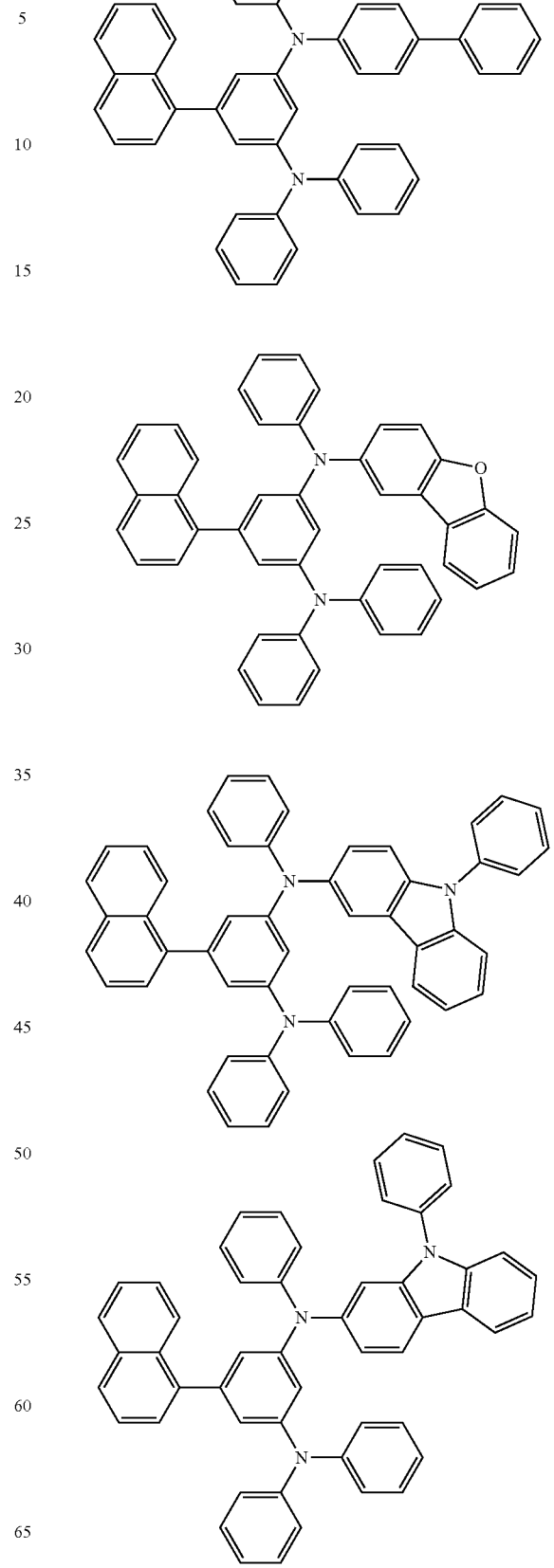

-continued
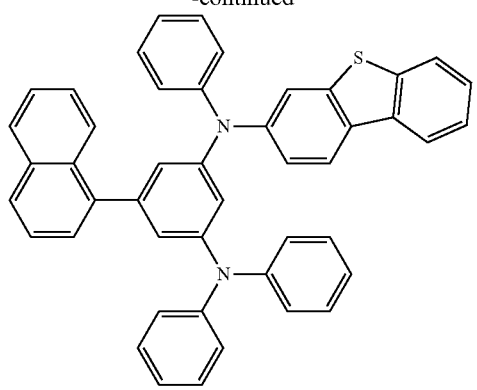
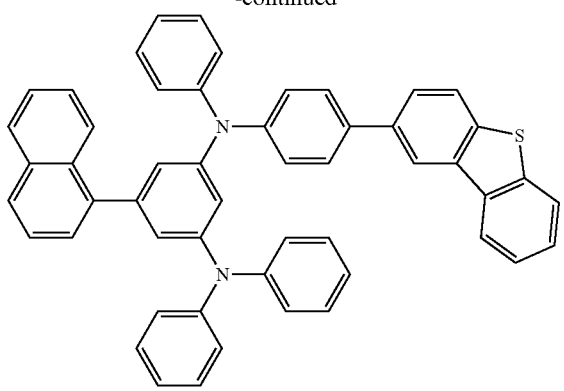
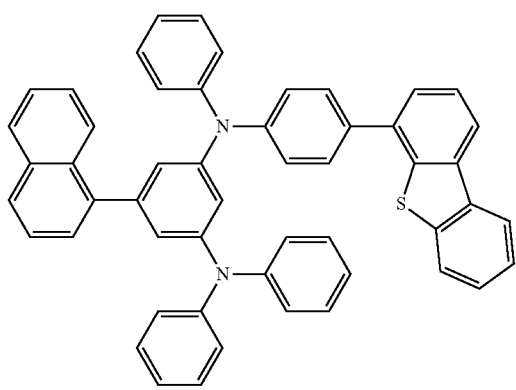
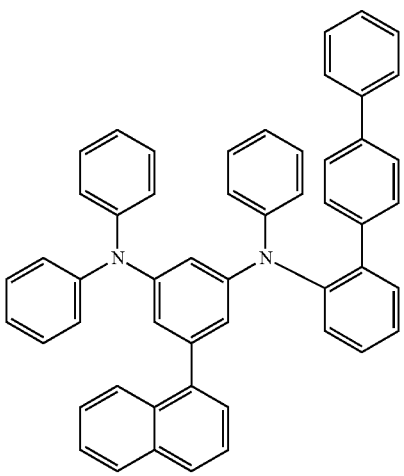
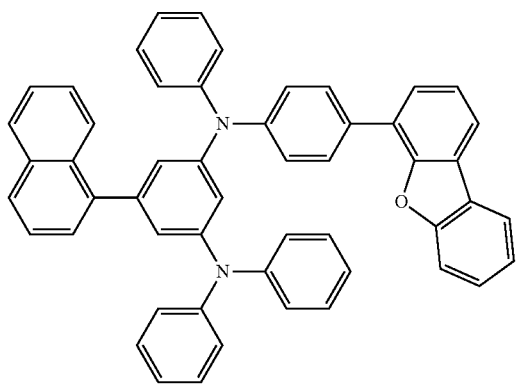
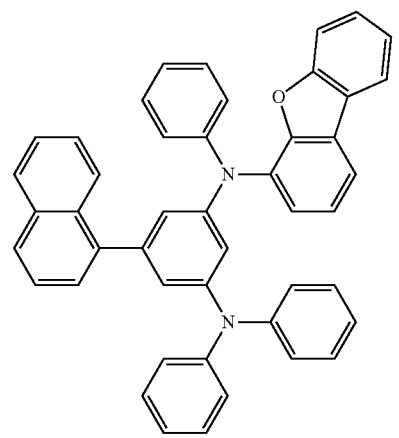
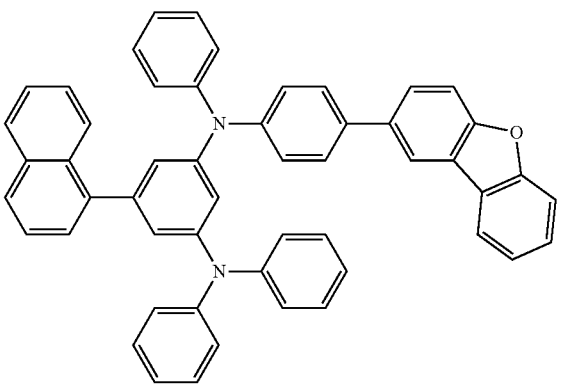
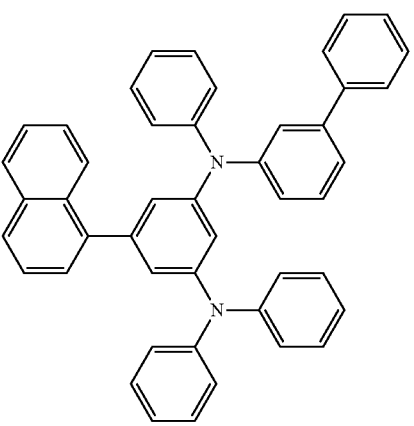

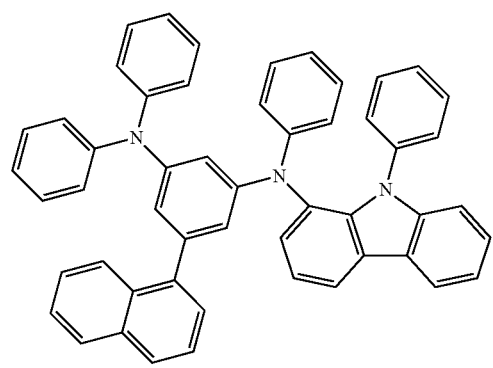
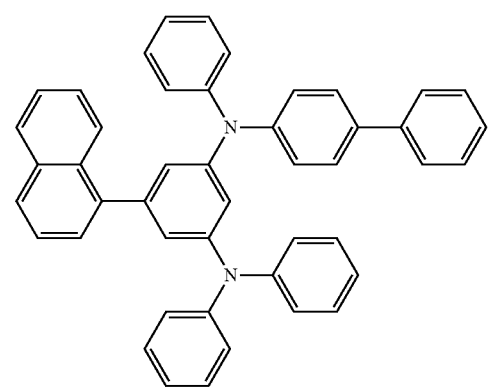
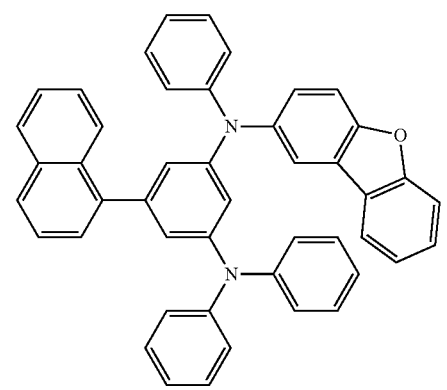
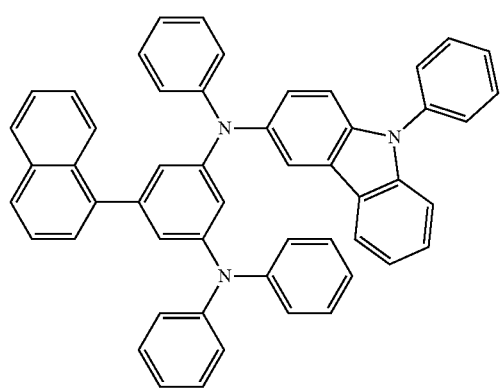
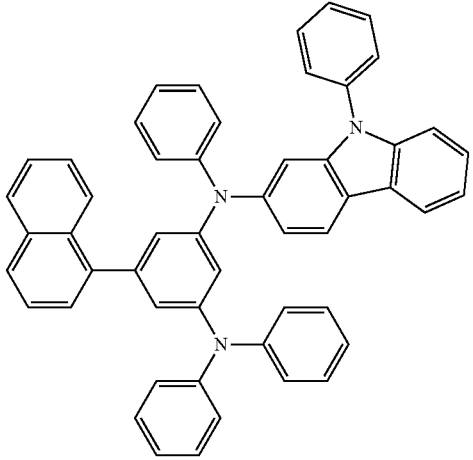
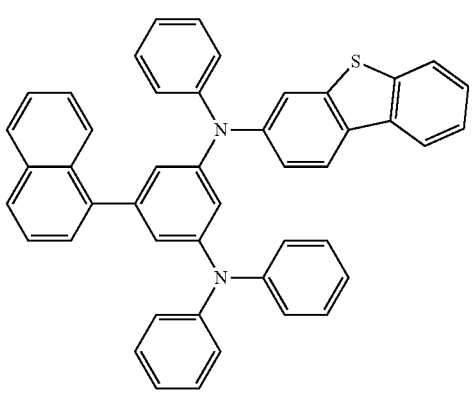
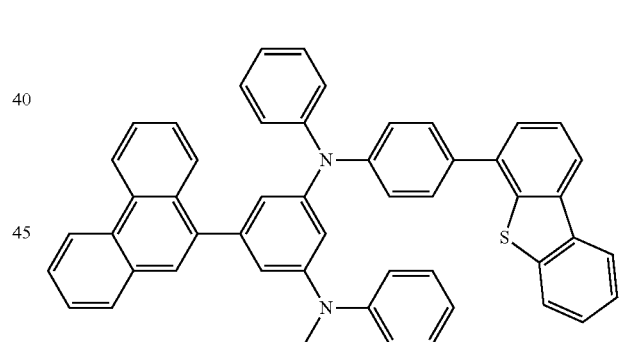
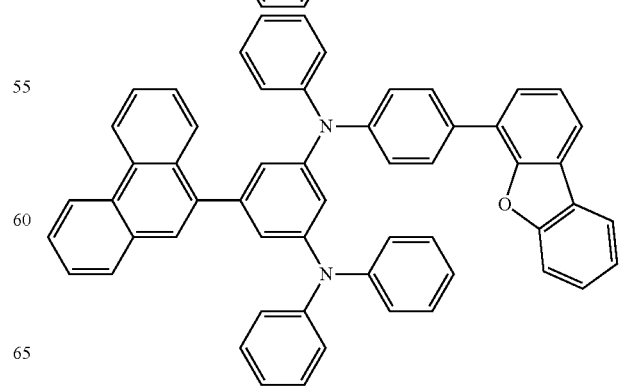

-continued
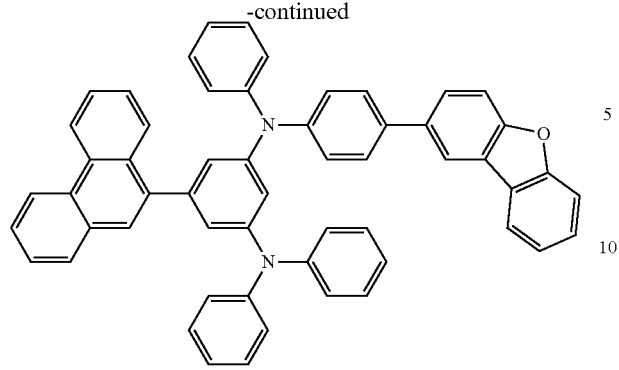
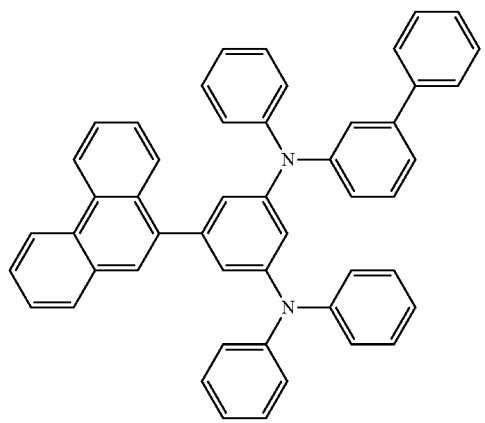
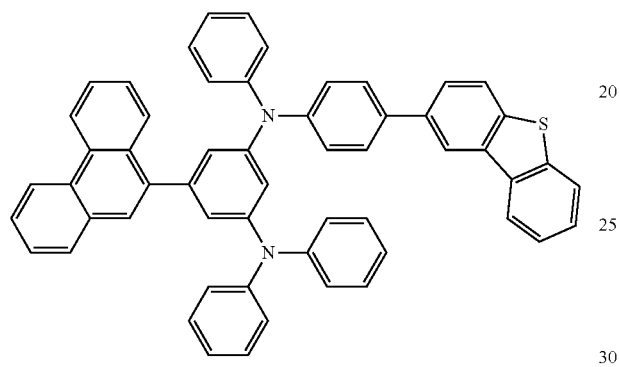
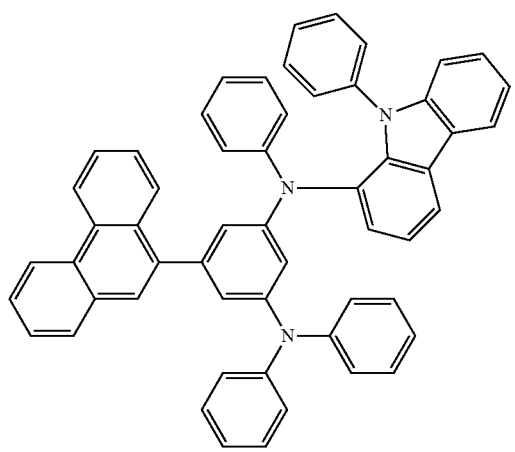
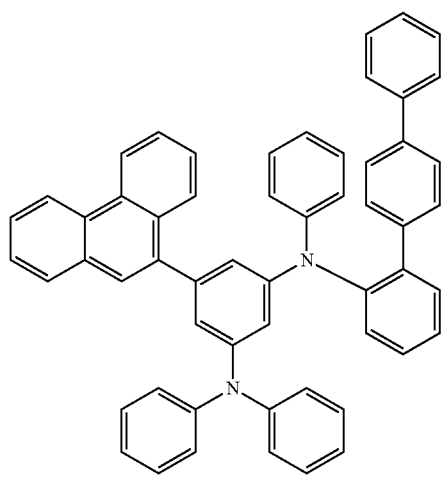
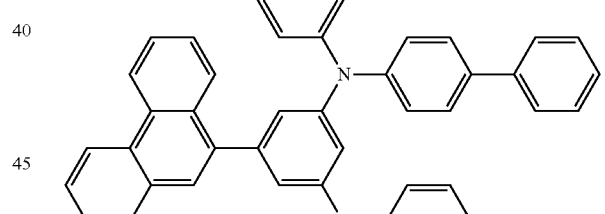
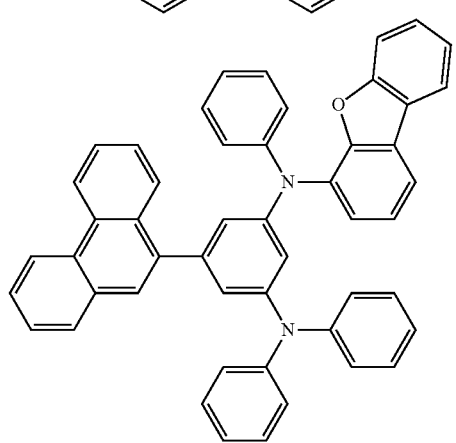
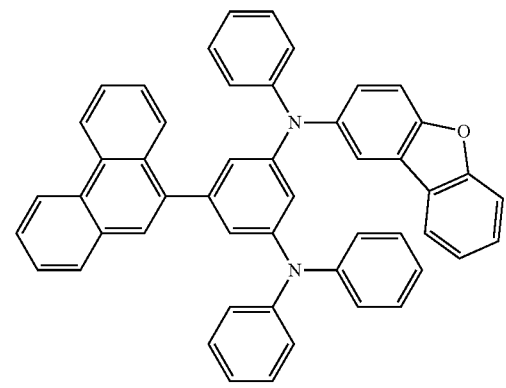

-continued
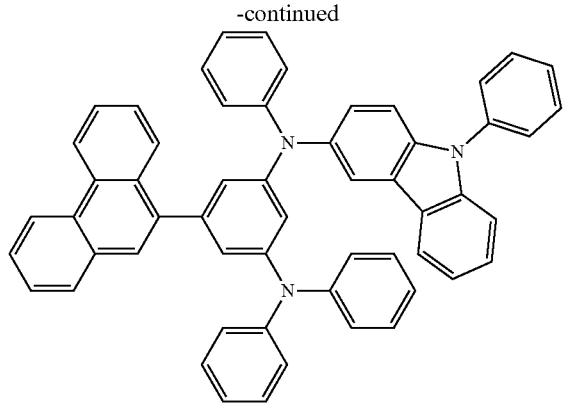
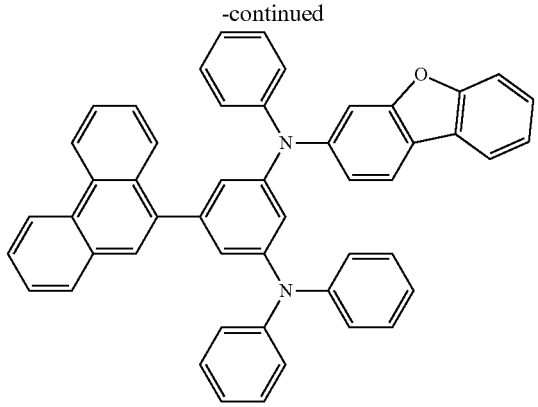
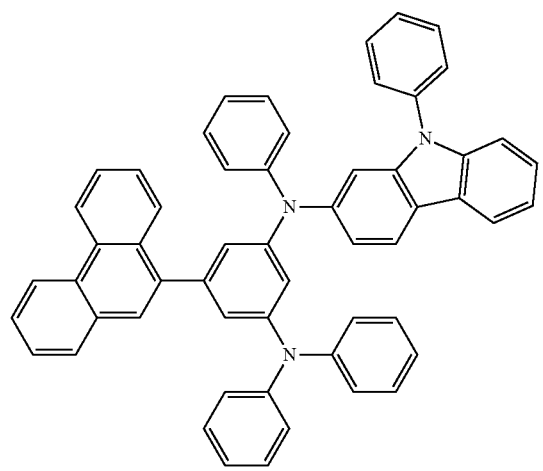
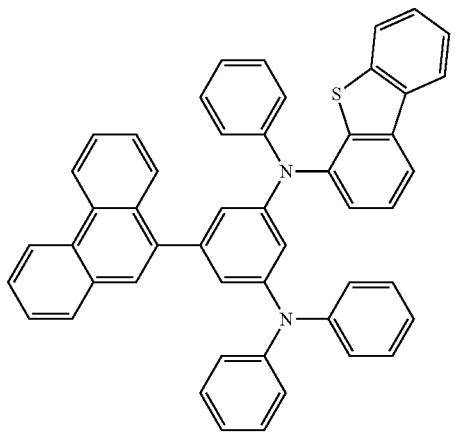
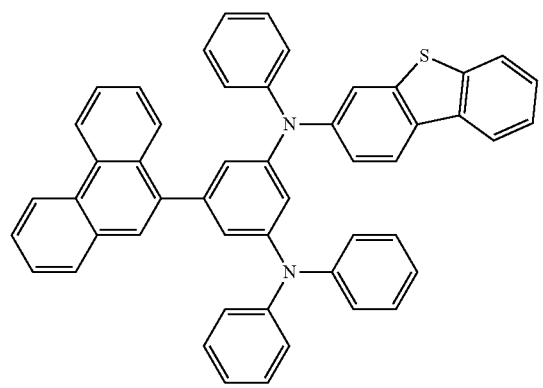
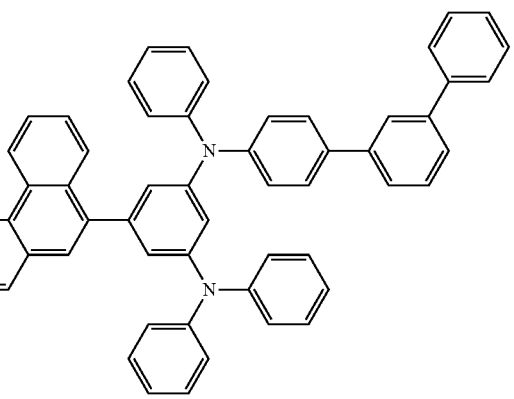
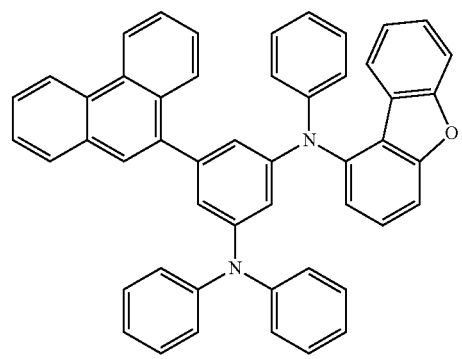
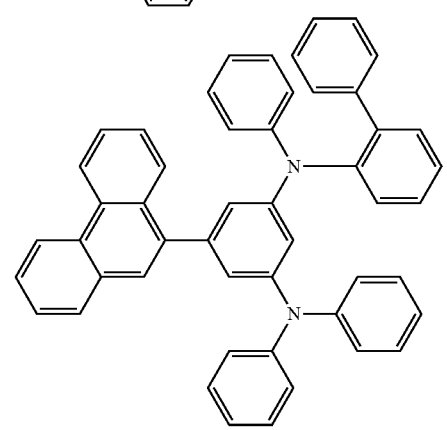

25
-continued
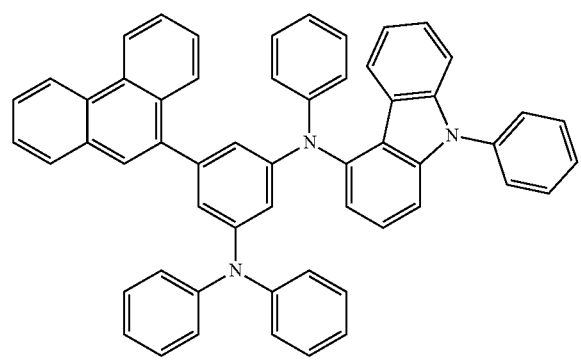
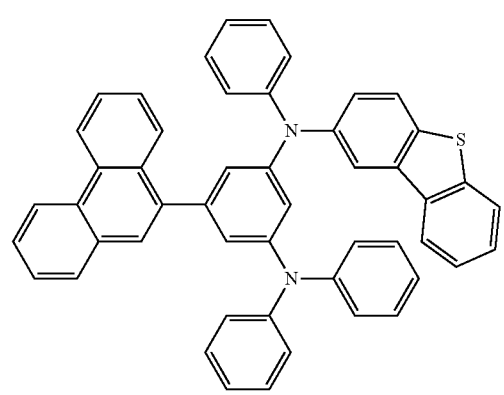
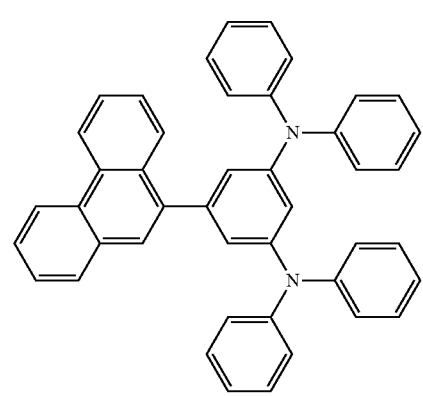
26
-continued
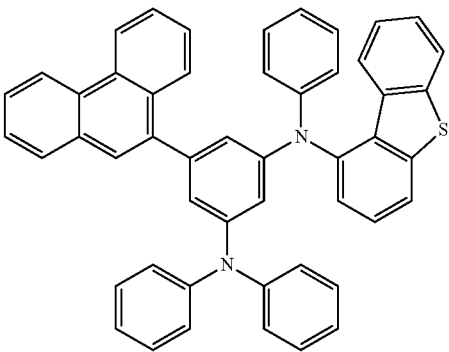
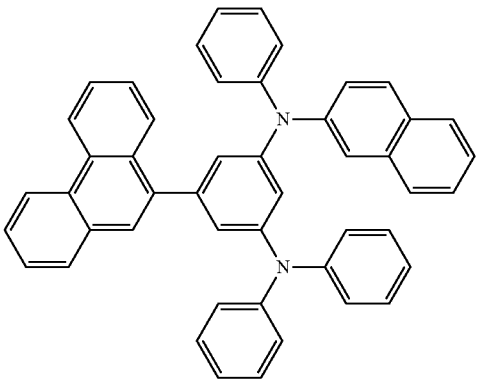
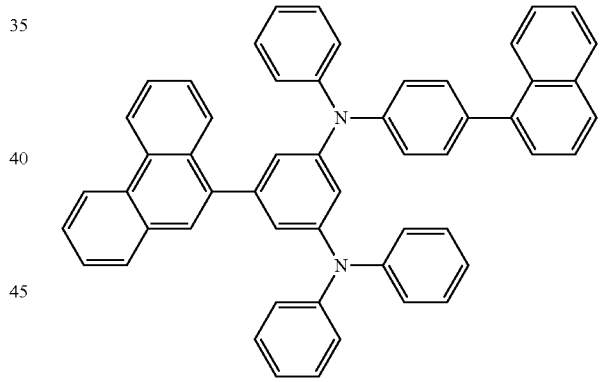
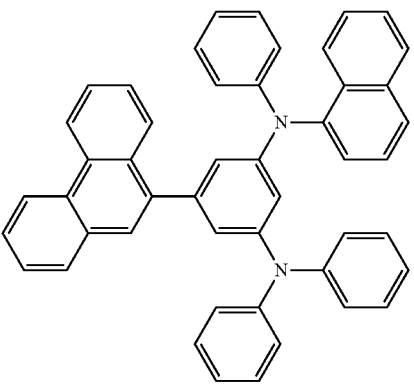

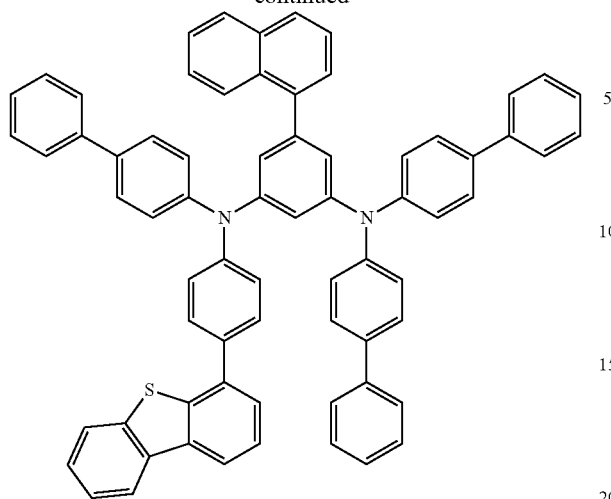
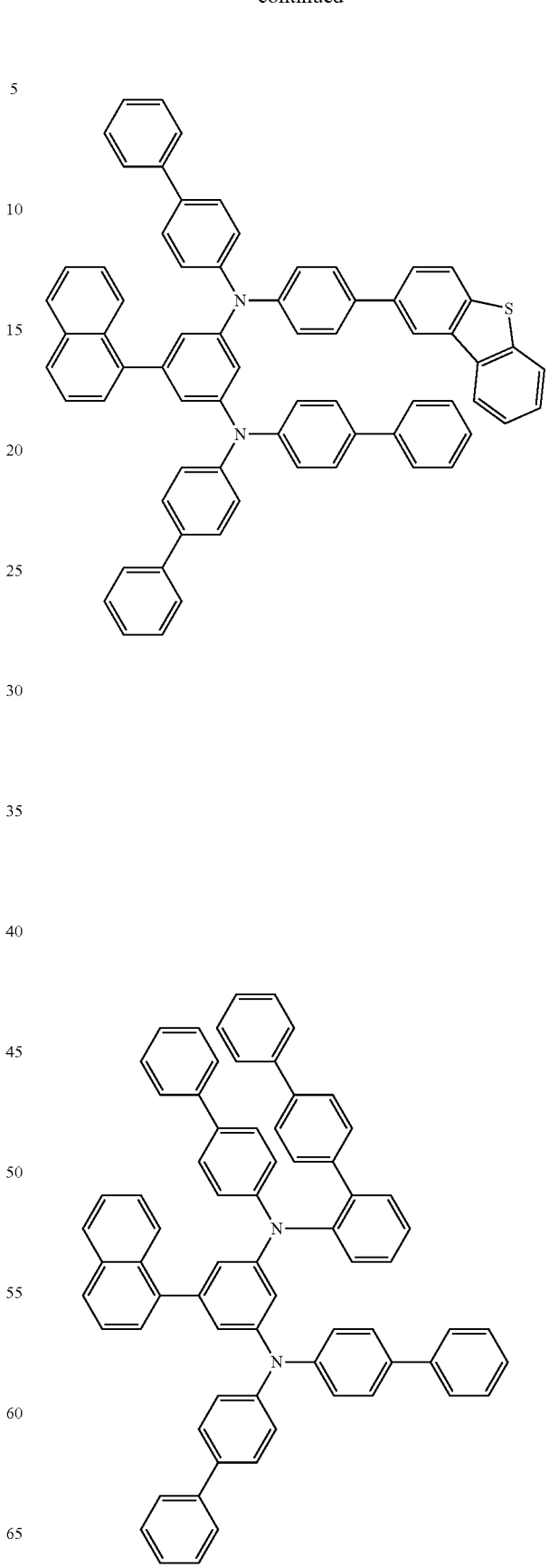

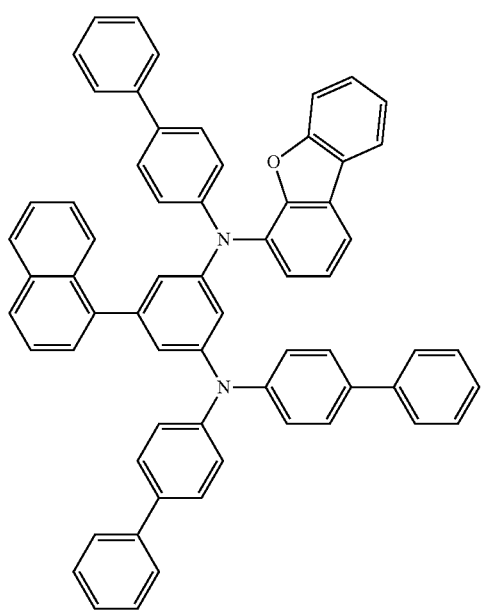
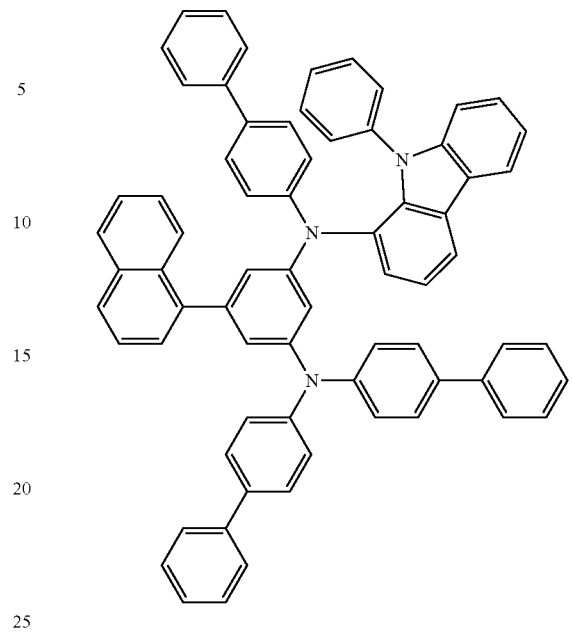
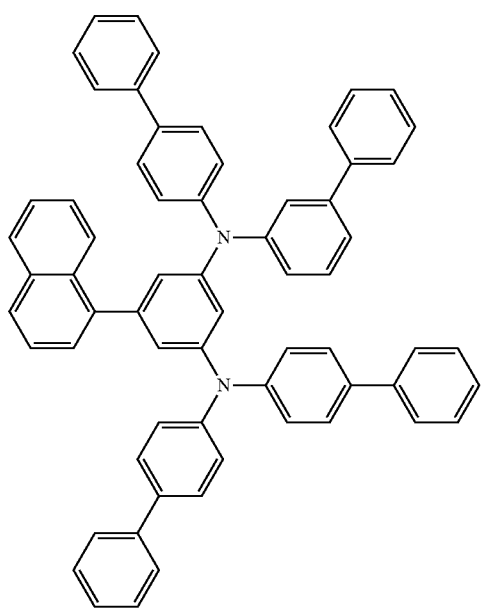
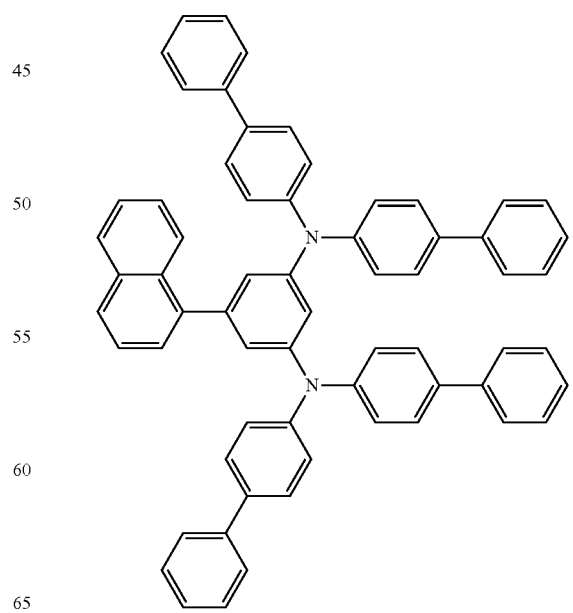

31
-continued
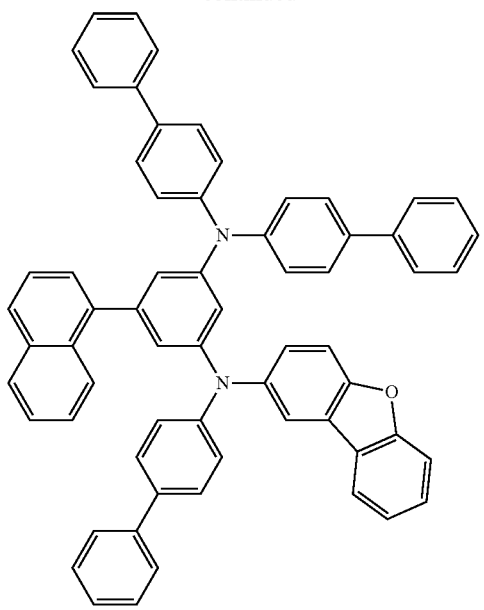
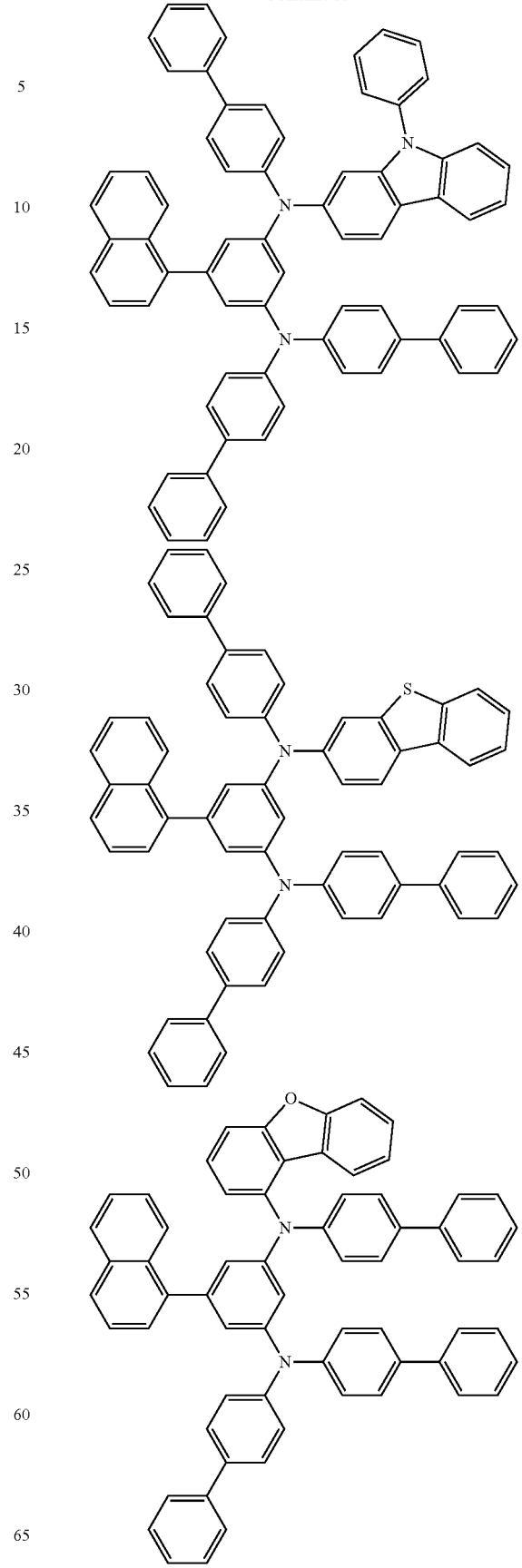
32
-continued
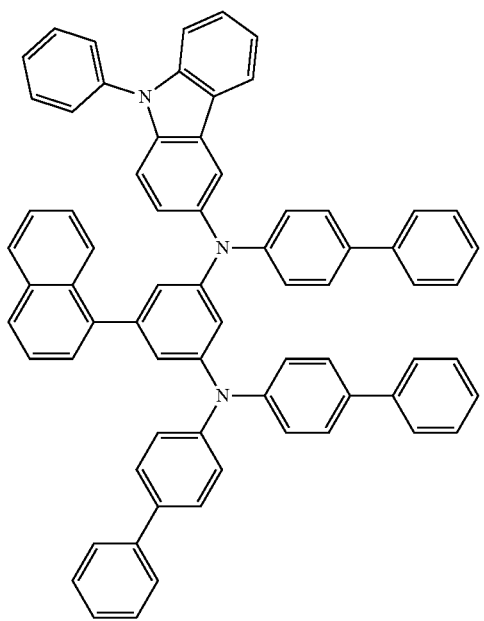

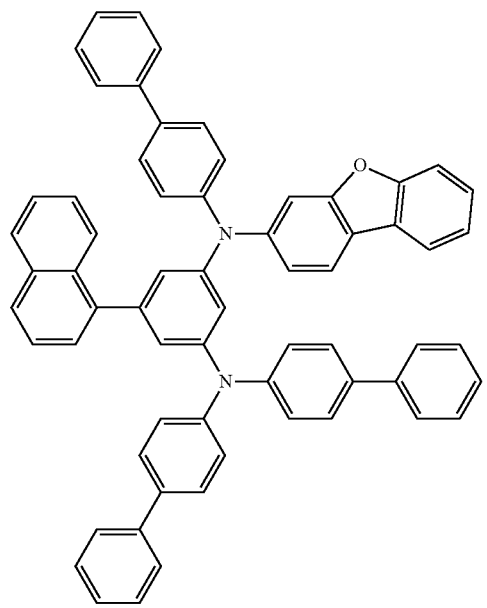
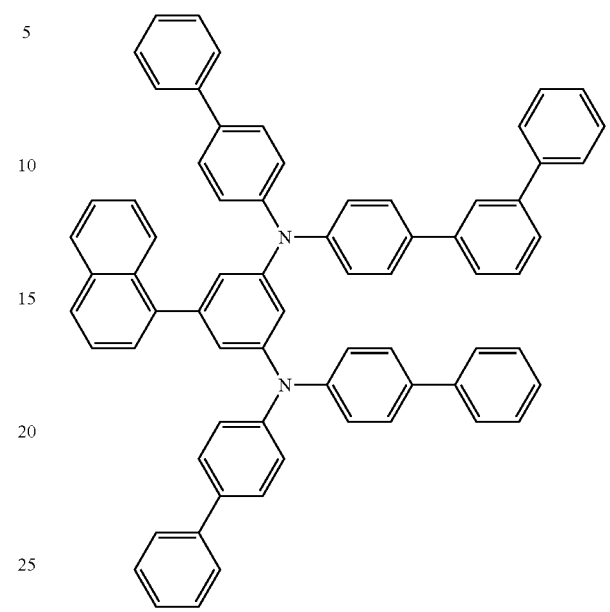
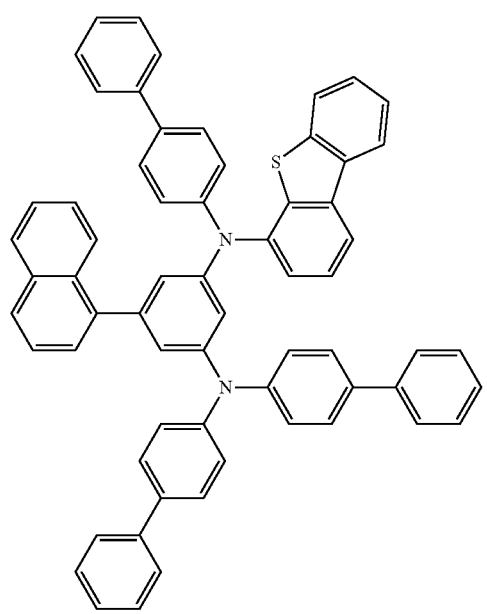 [SMILES: c1ccc(-c2ccc(N(c3ccc(-c4ccccc4)cc3)c3cc(-c4cccc5ccccc45)cc(N(c4ccc(-c5ccccc5)cc4)c4cccc5ccccc45)c3)cc2)cc1]
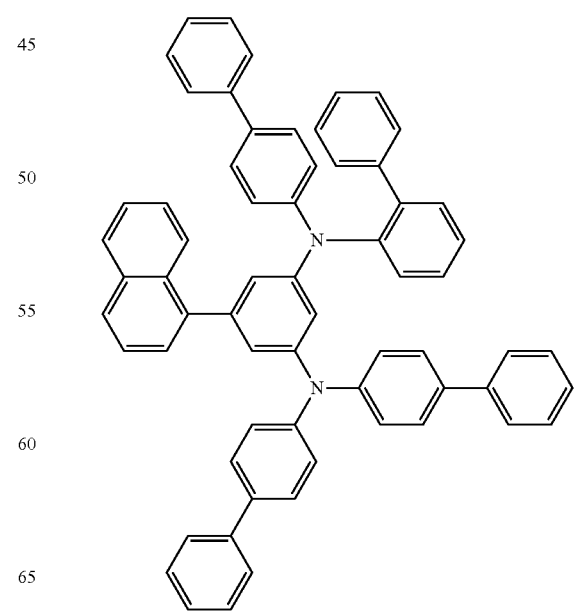

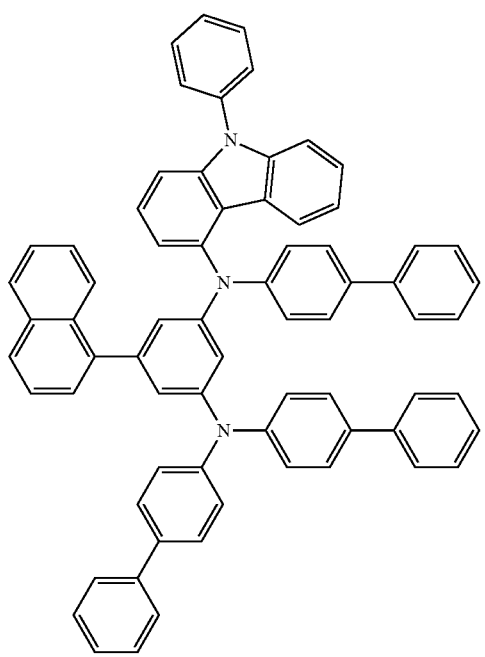
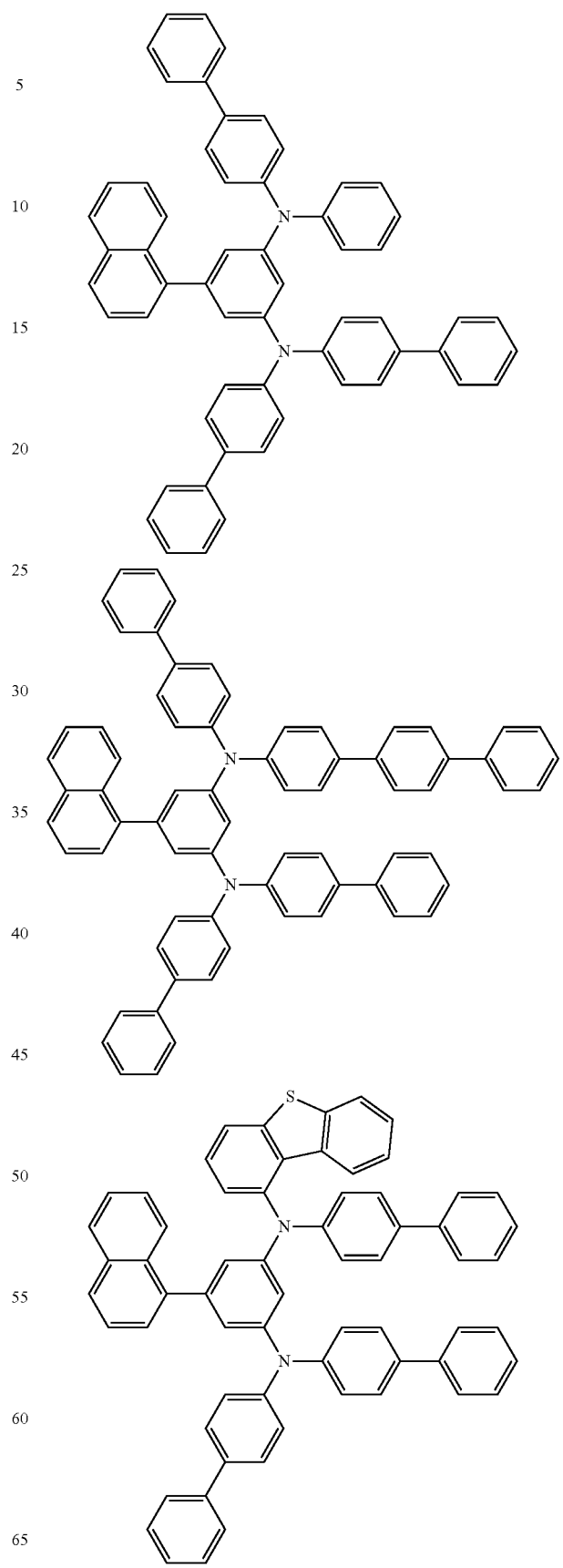

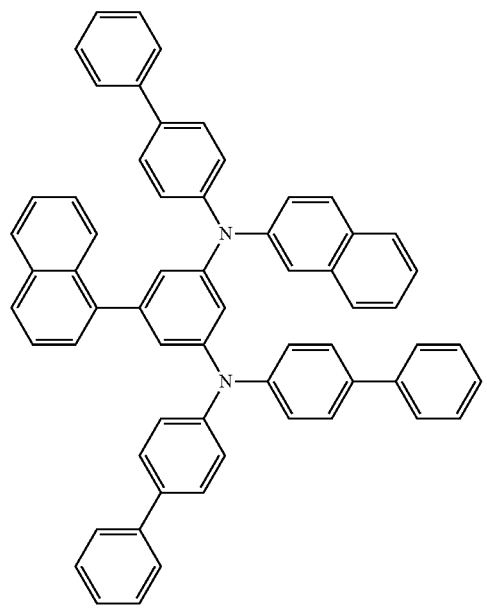
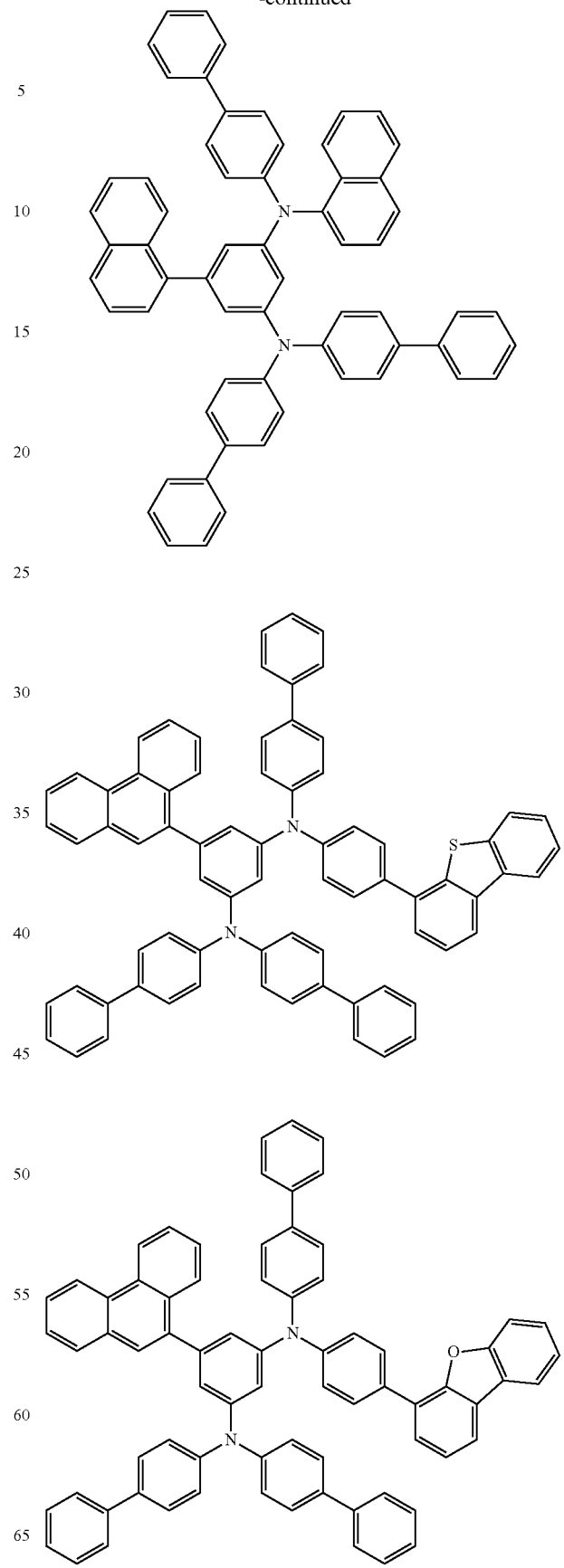

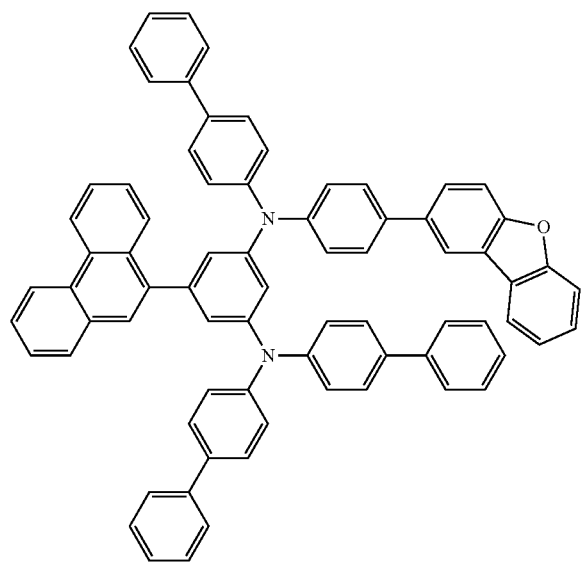
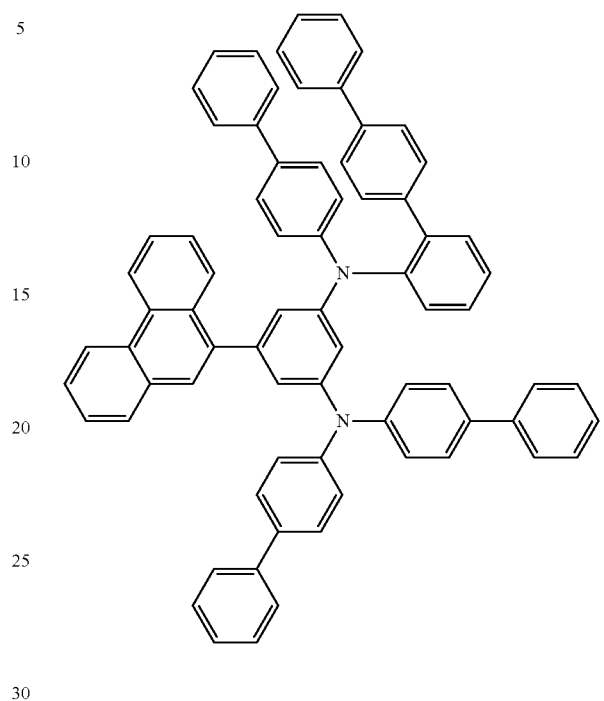
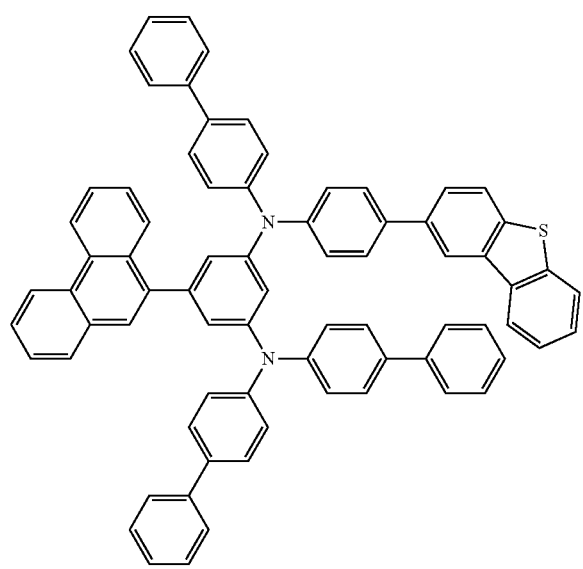
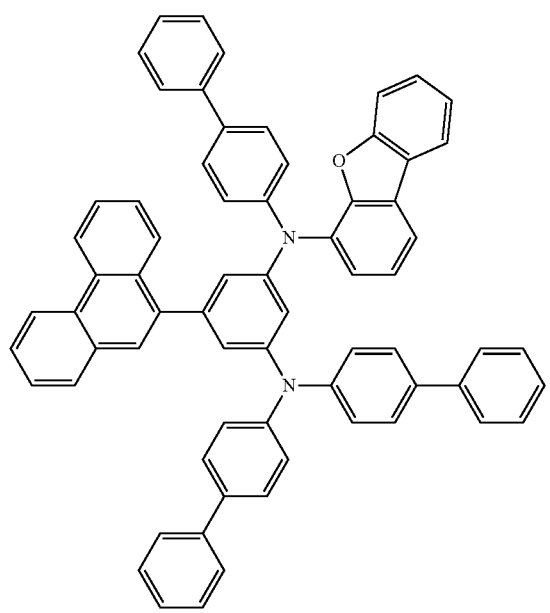

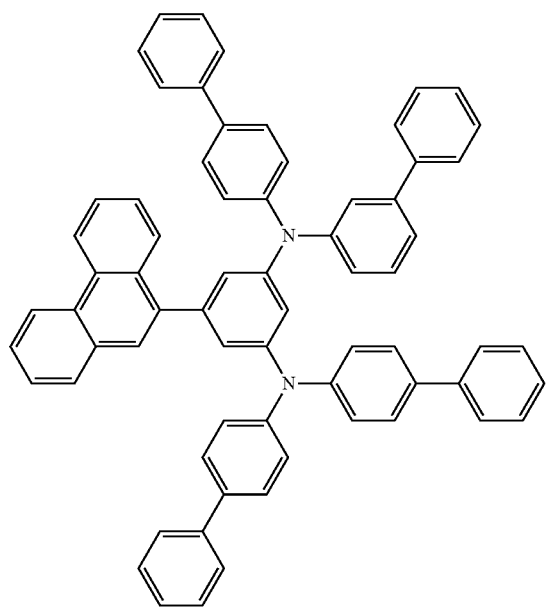
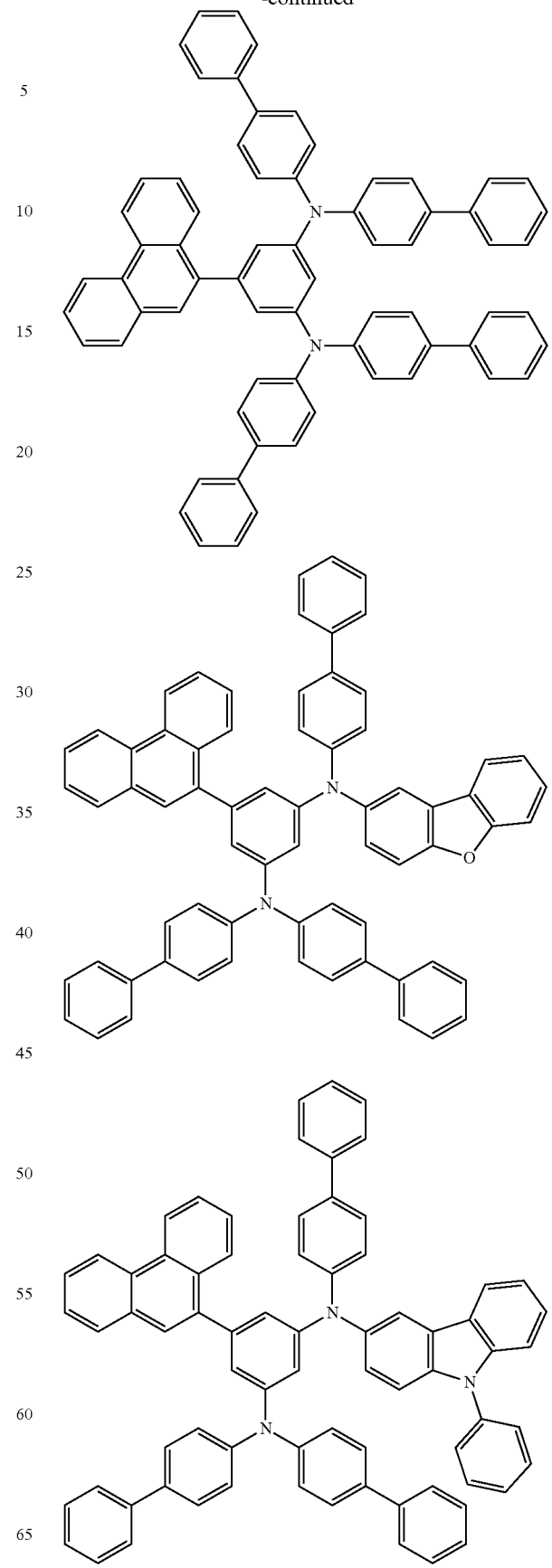

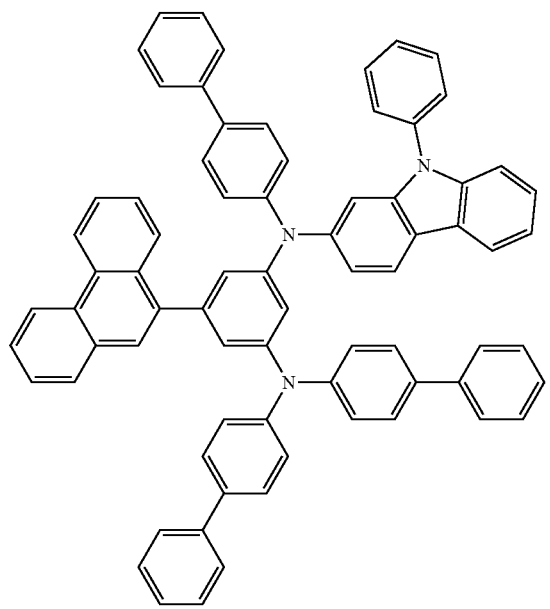
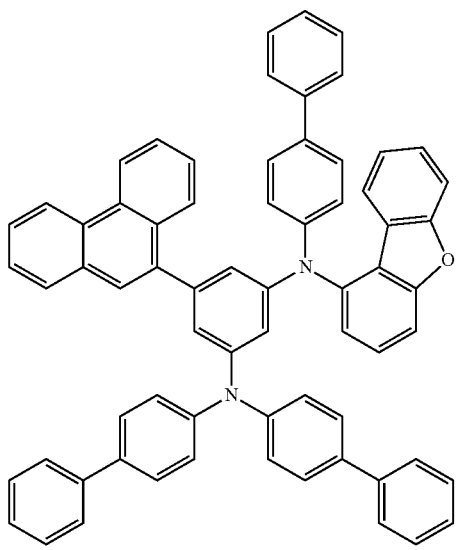
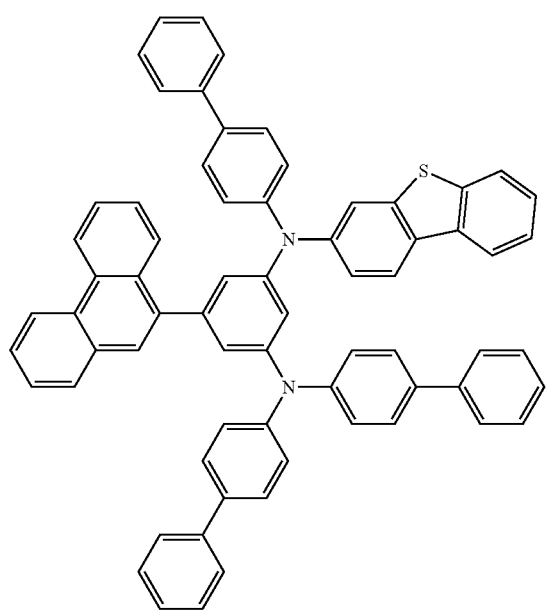
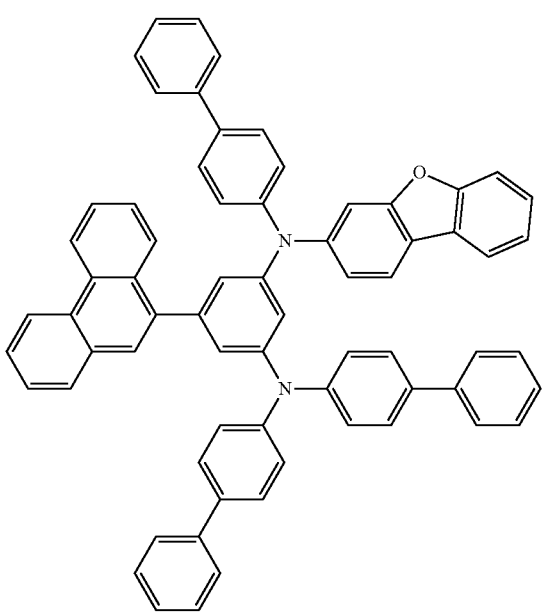

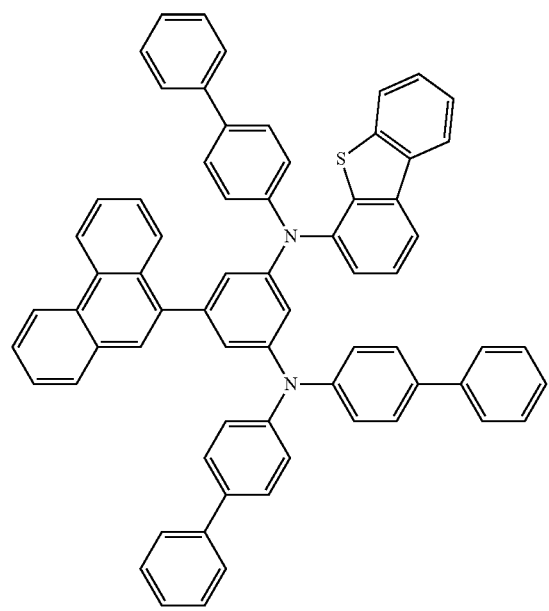
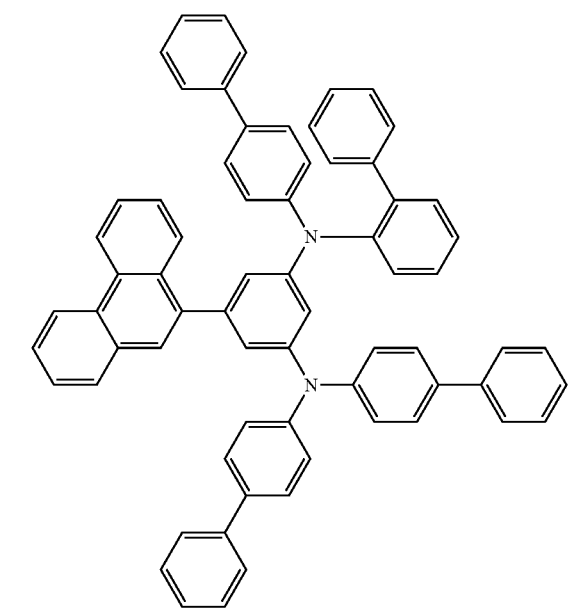
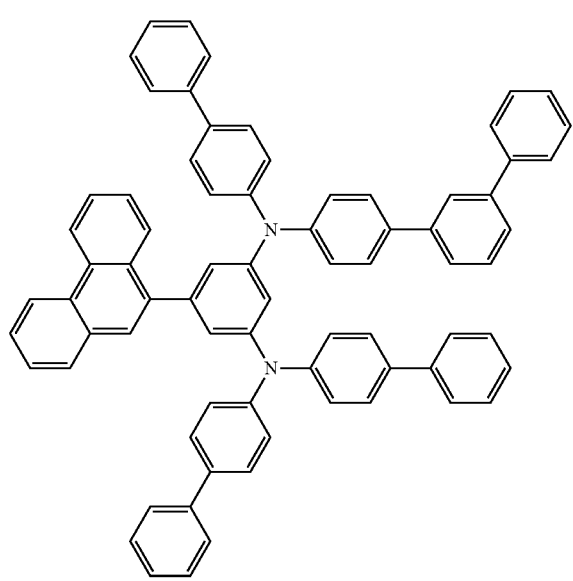
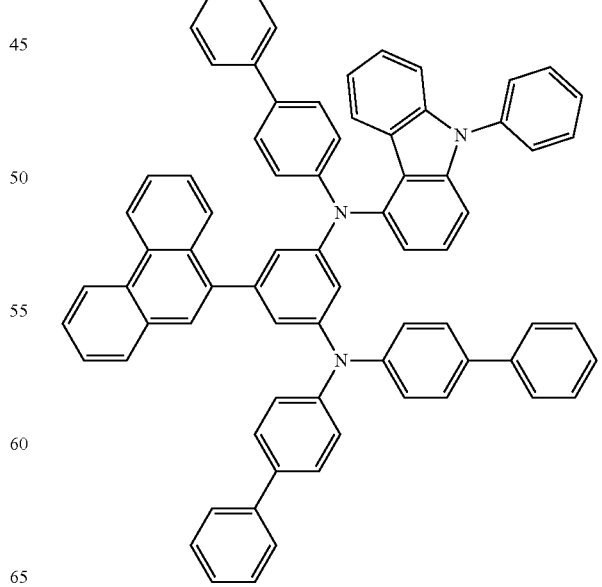

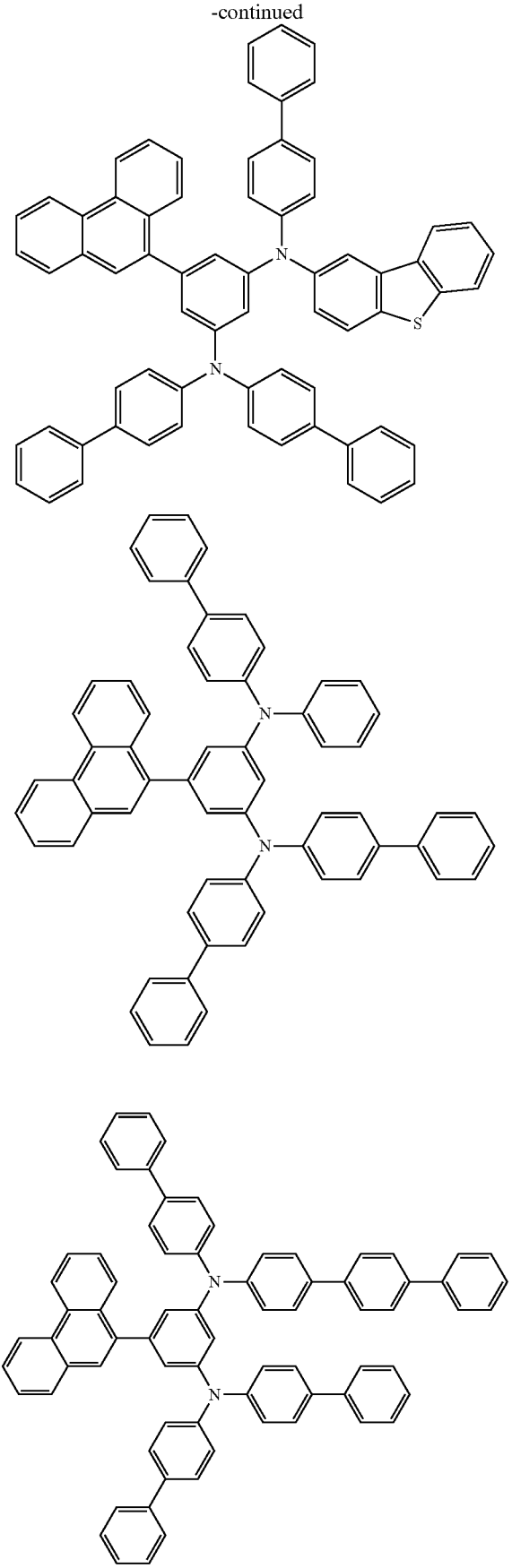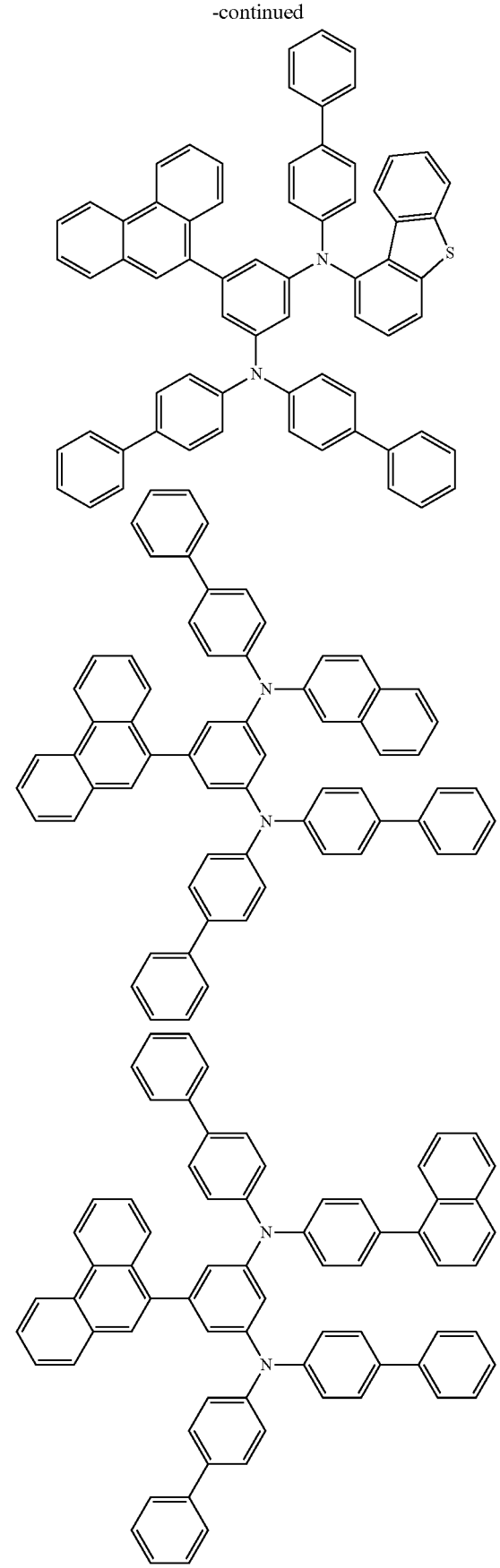

49
-continued
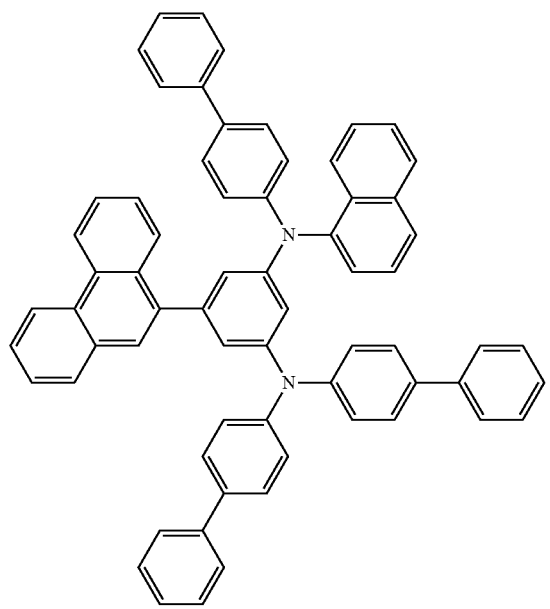
50
-continued
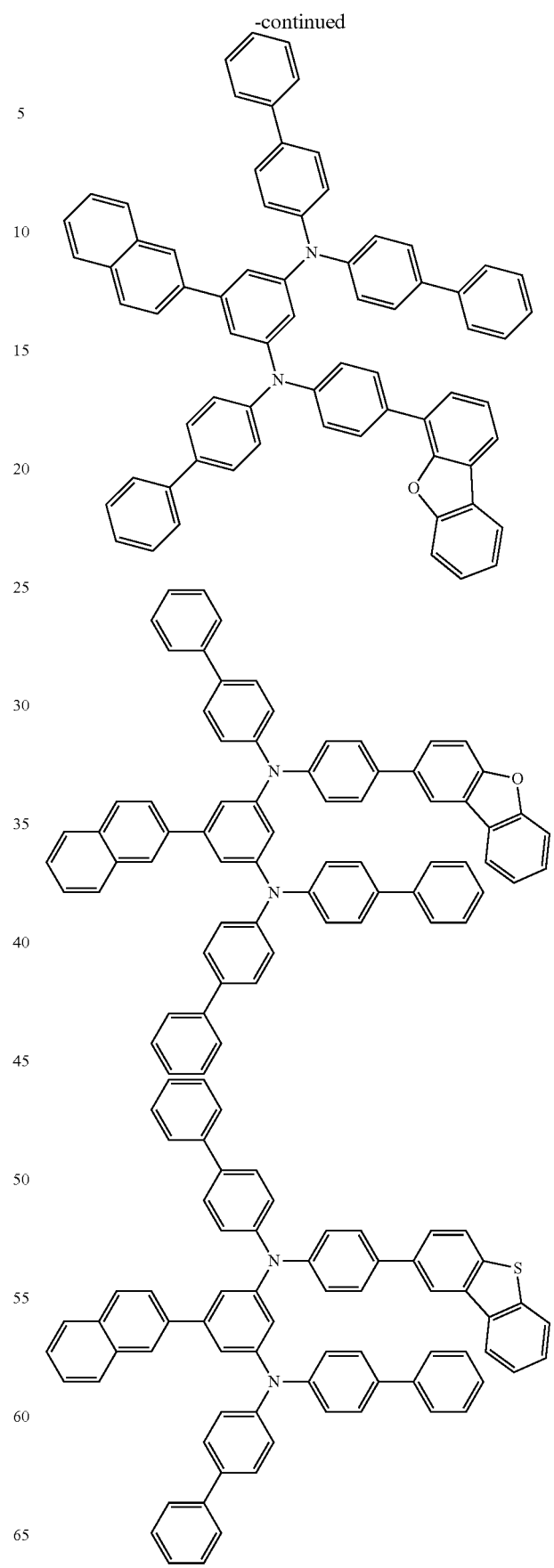
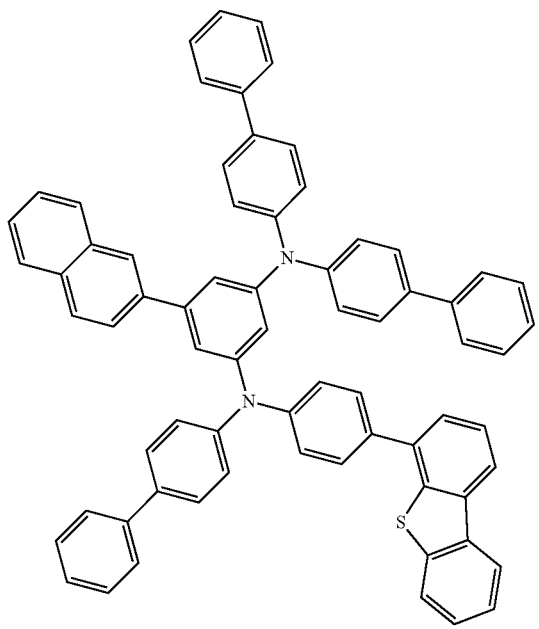

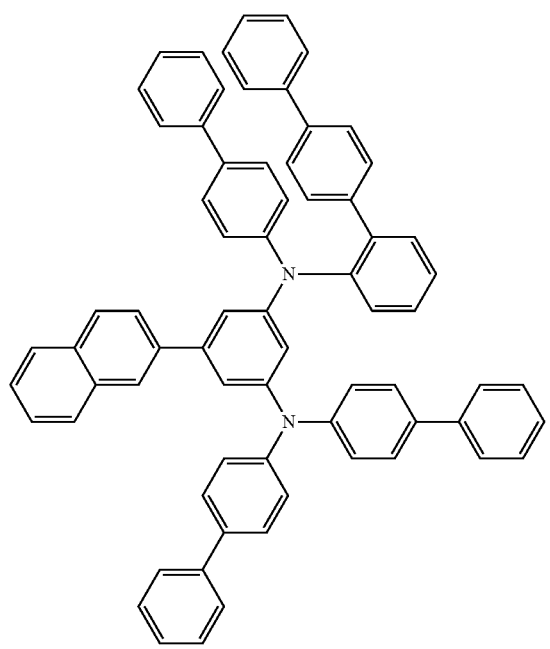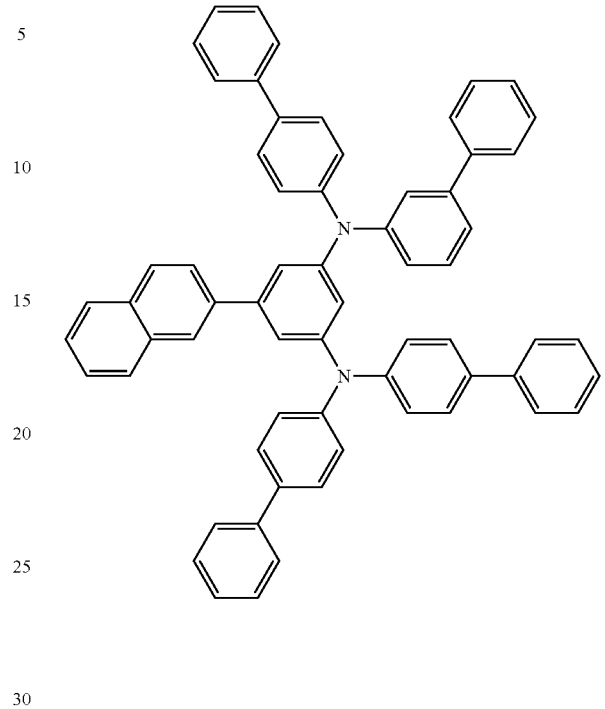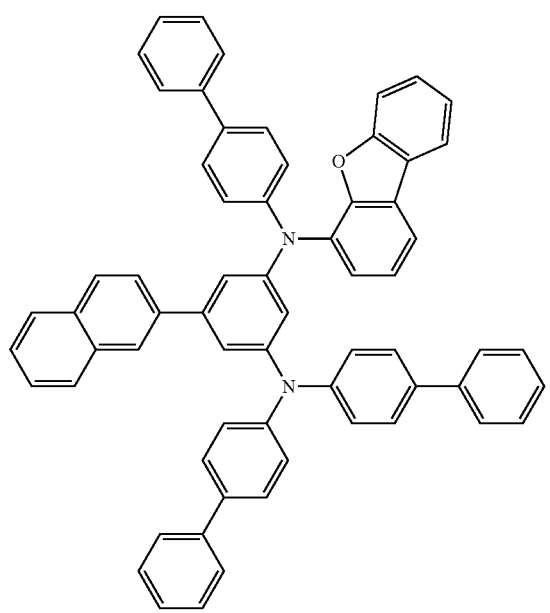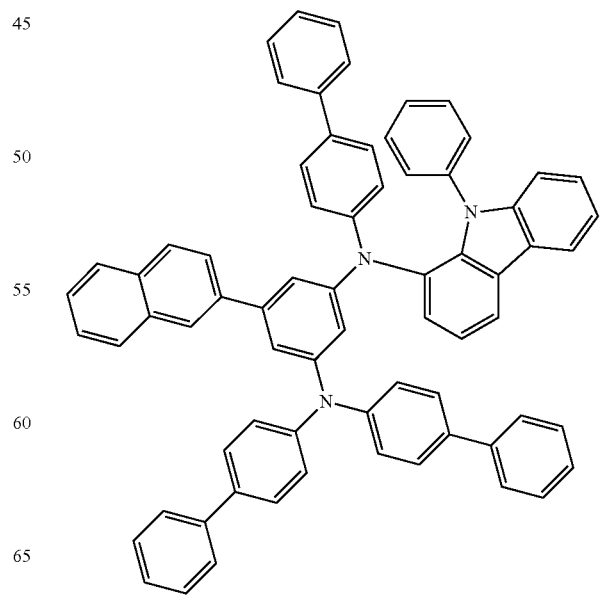

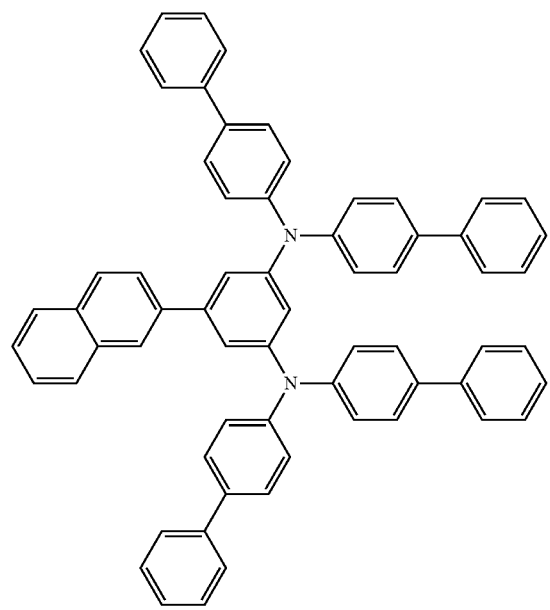
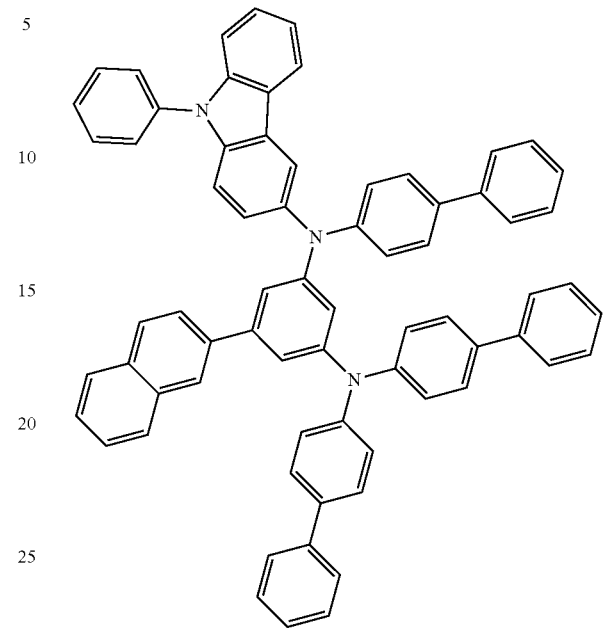
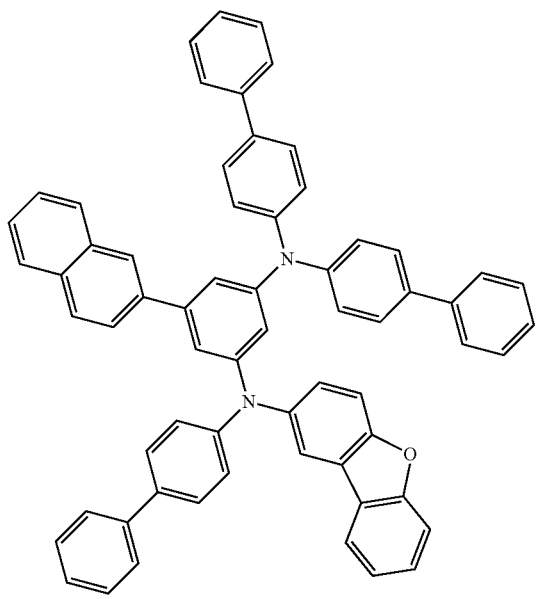
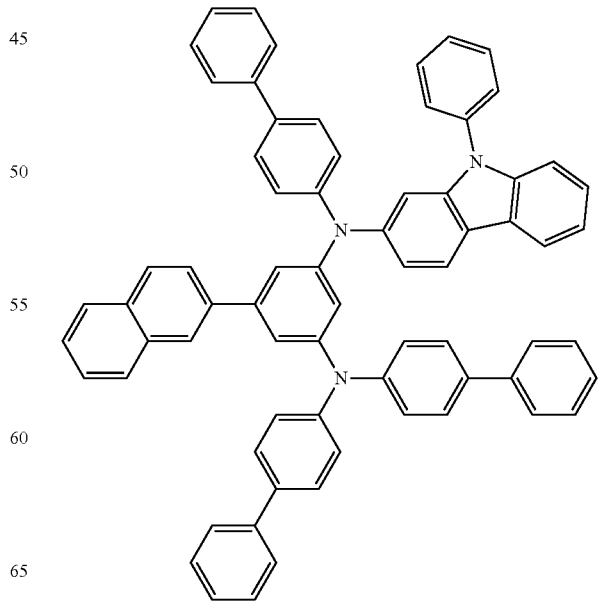

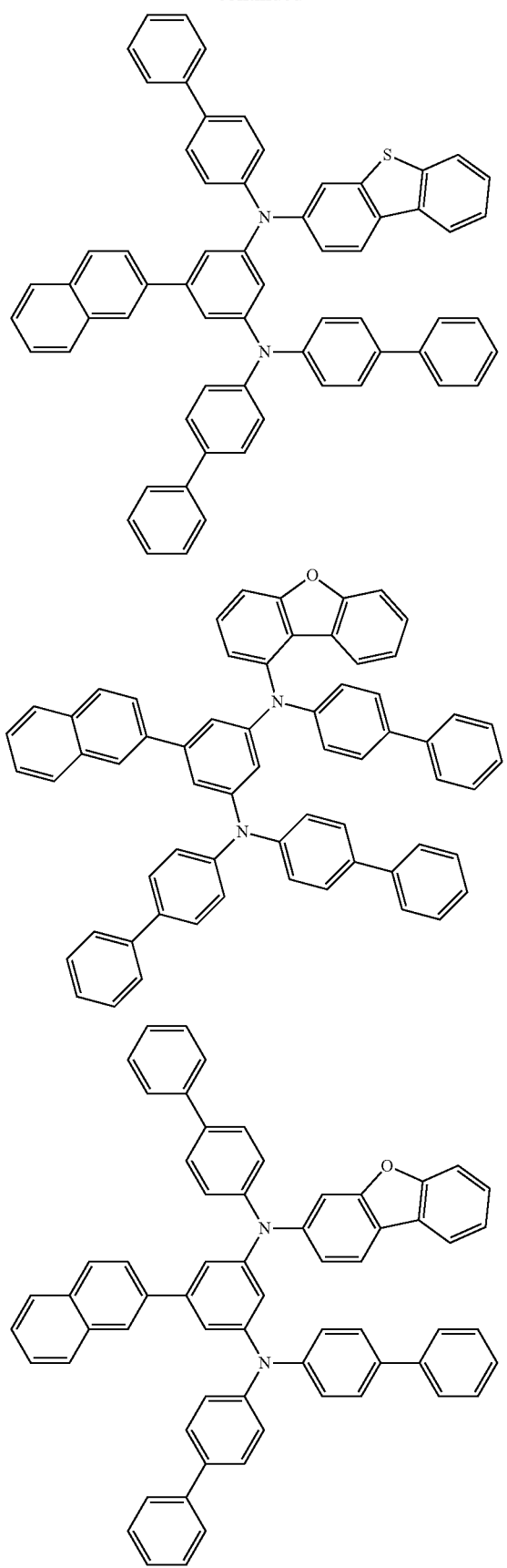
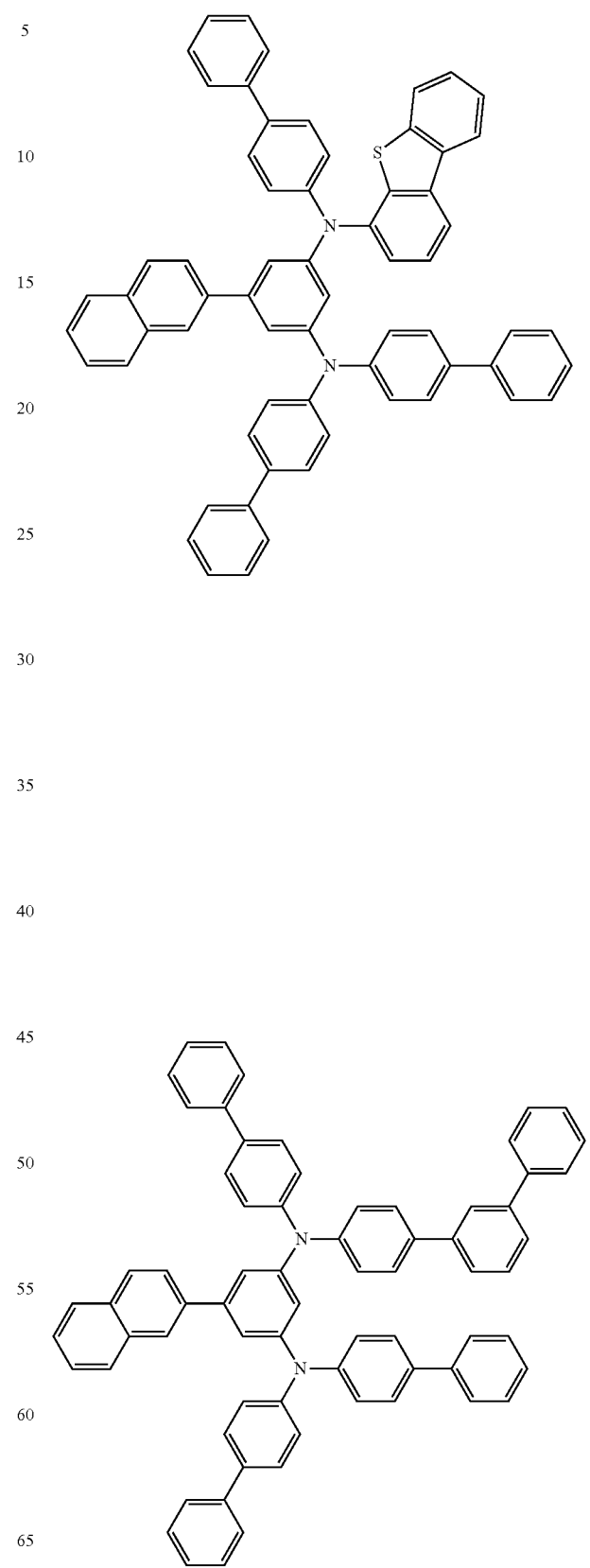

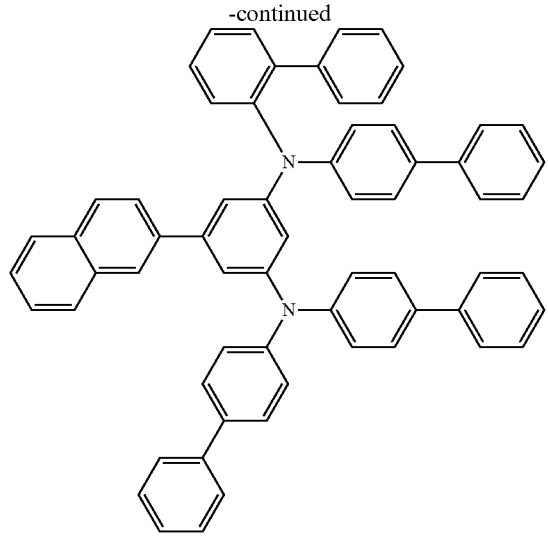
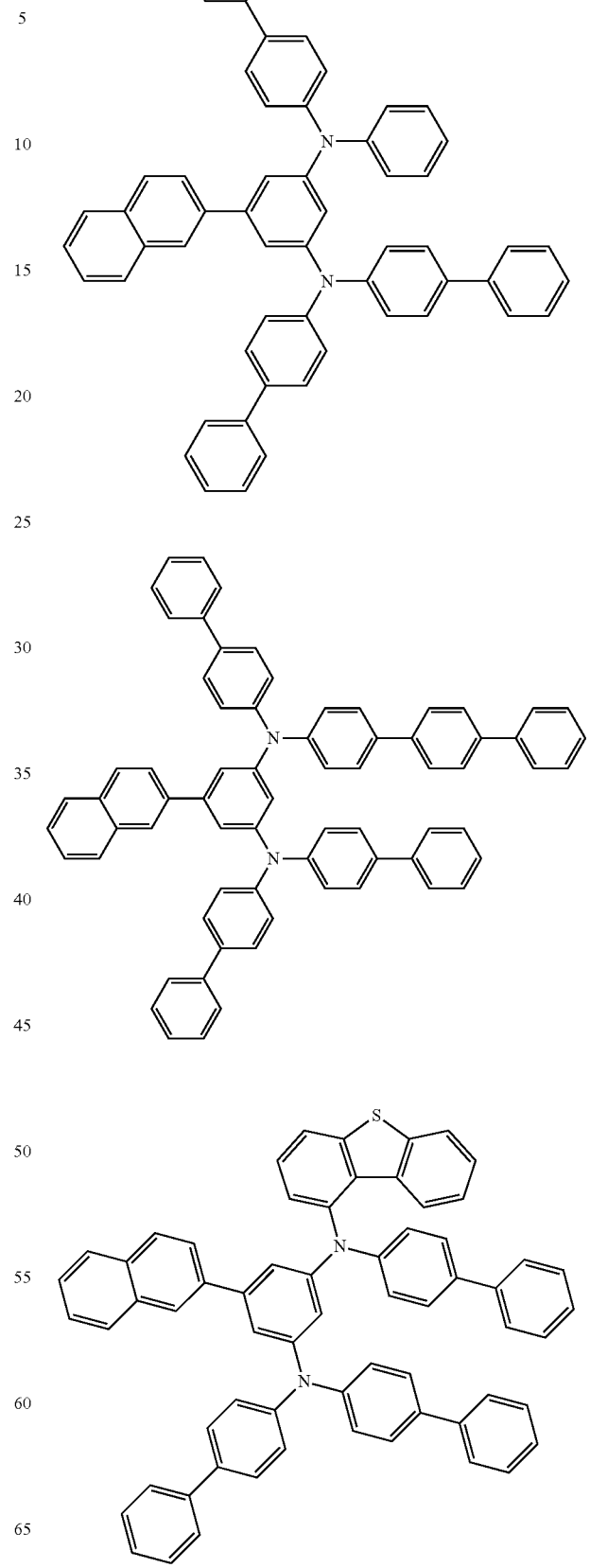

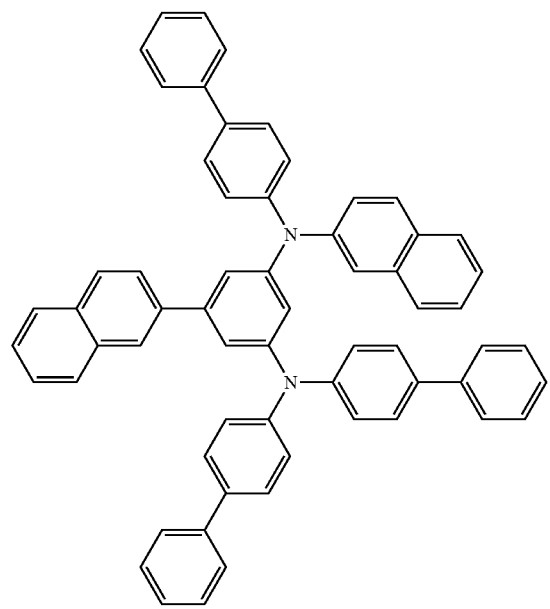
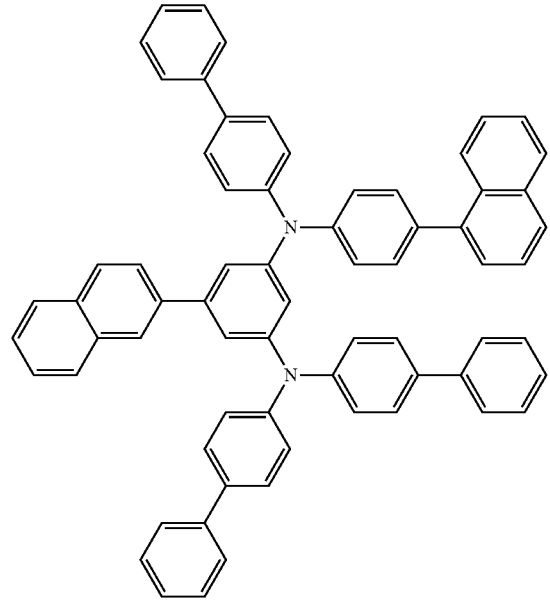
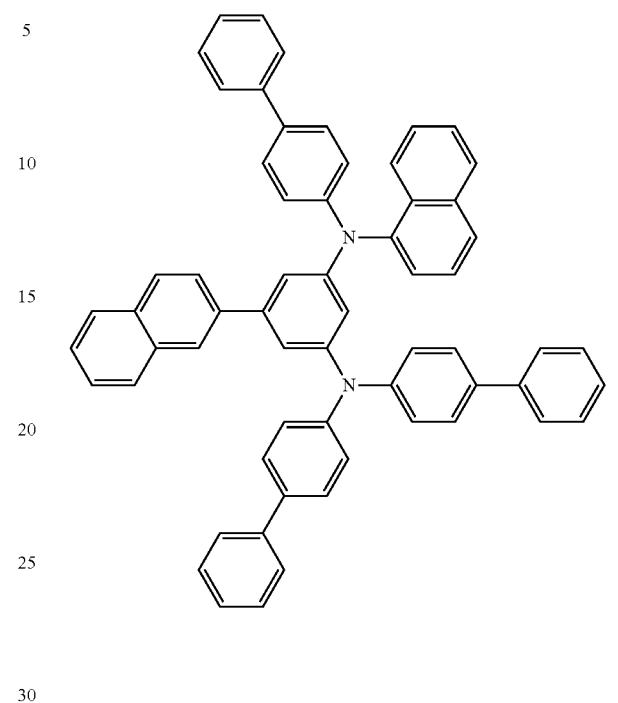
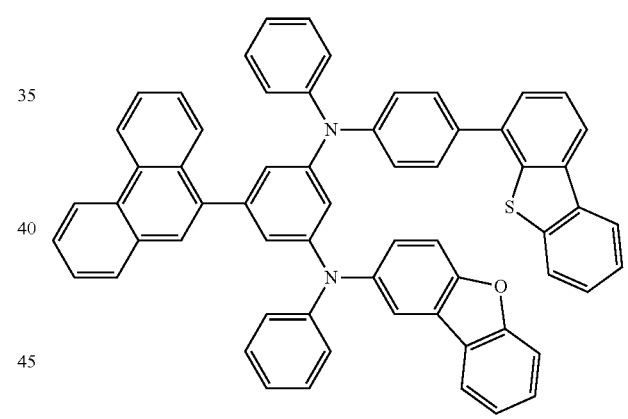
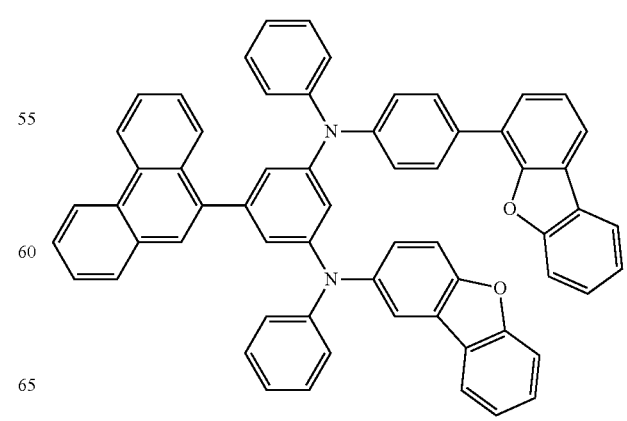

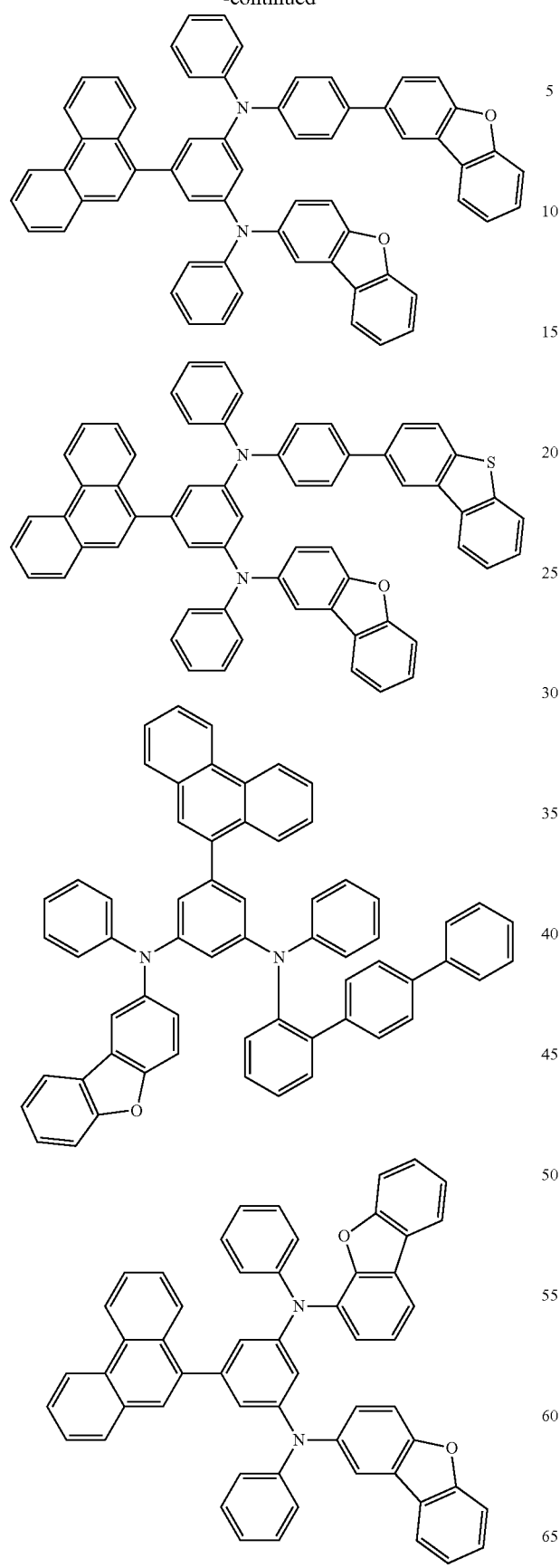
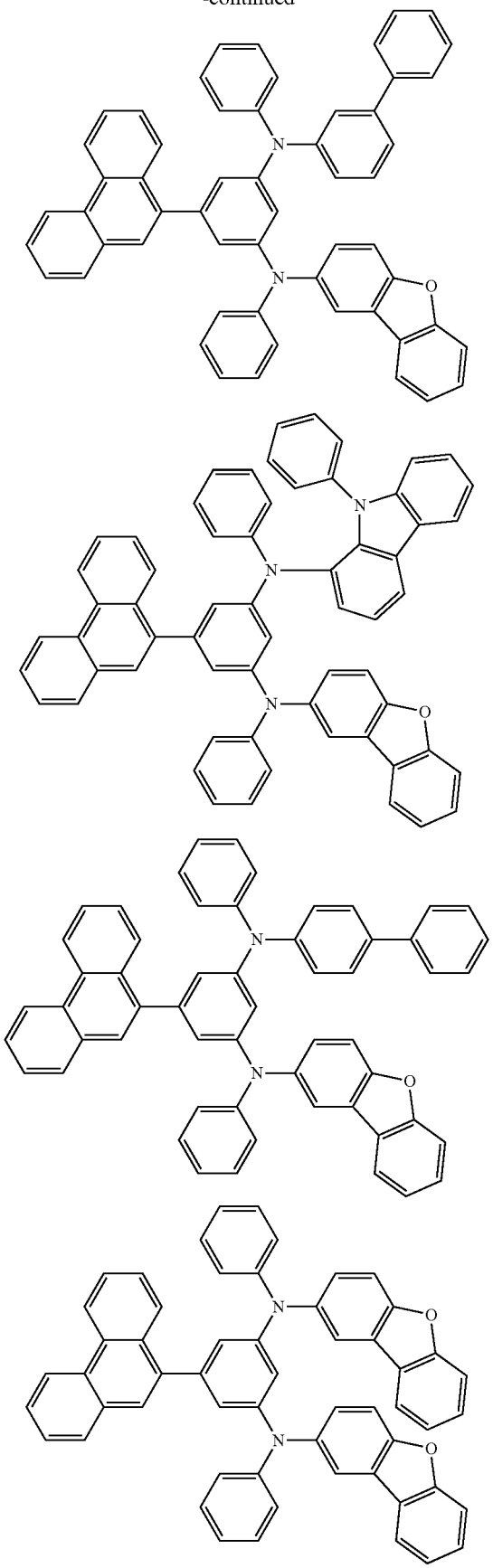

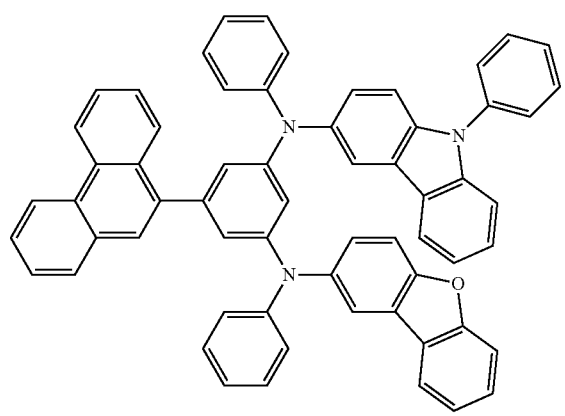
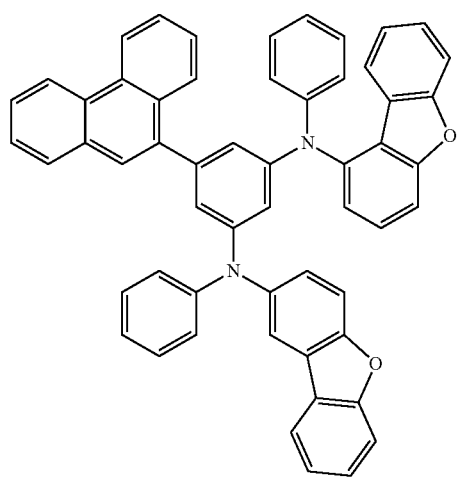
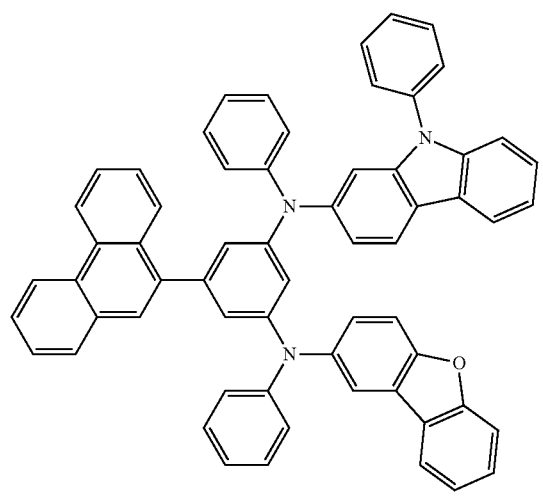
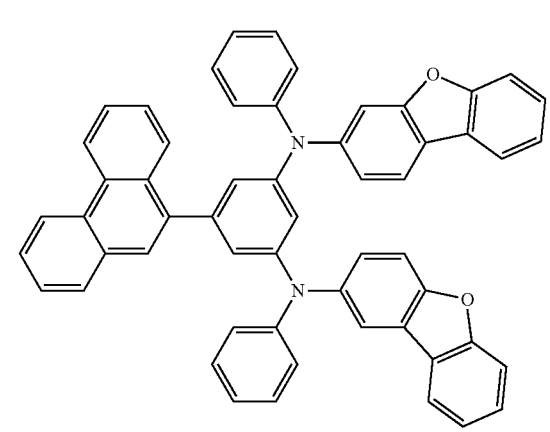
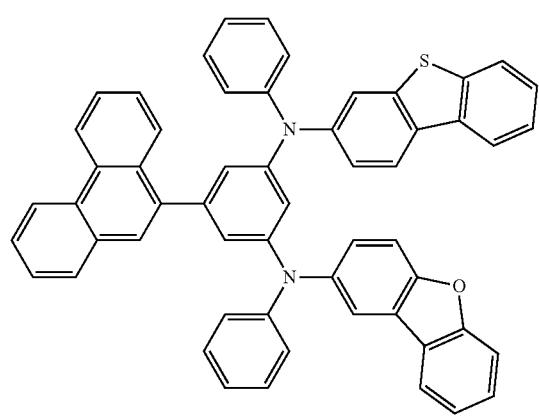
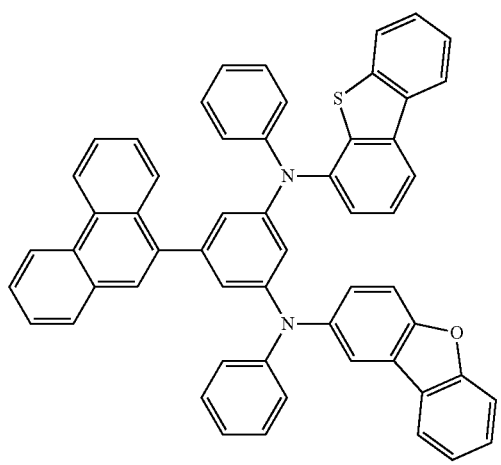

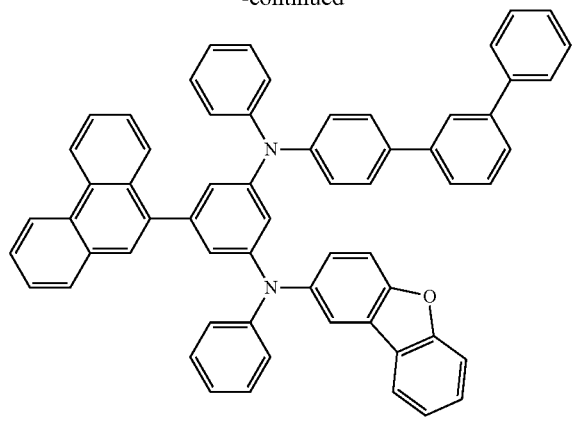
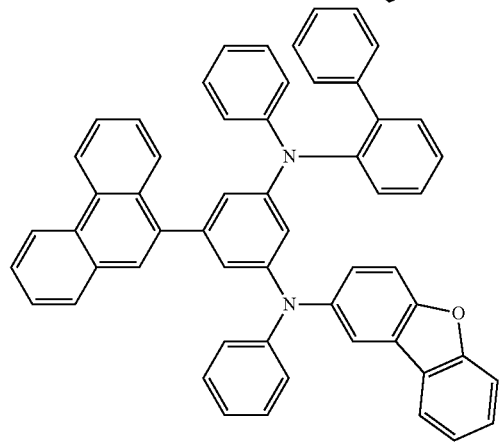
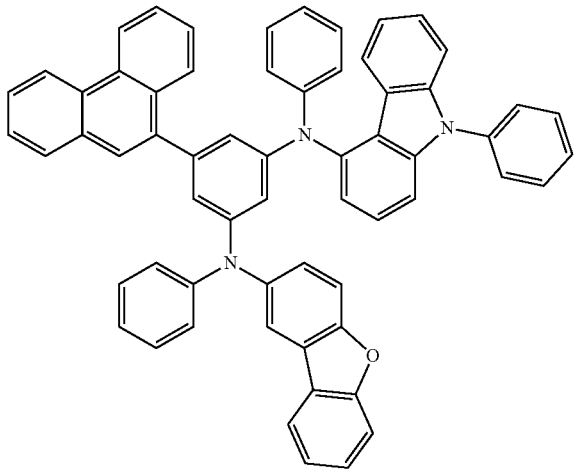
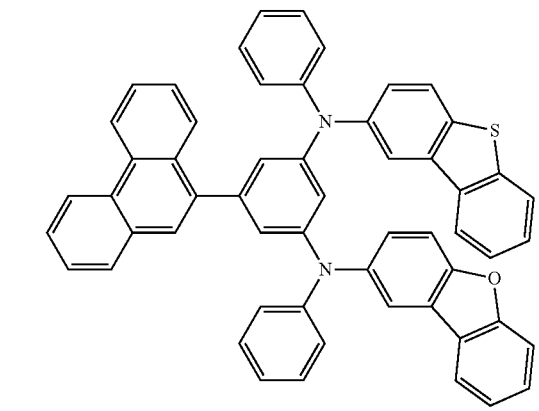
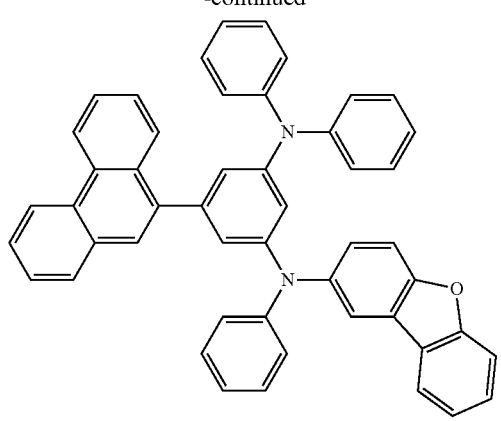
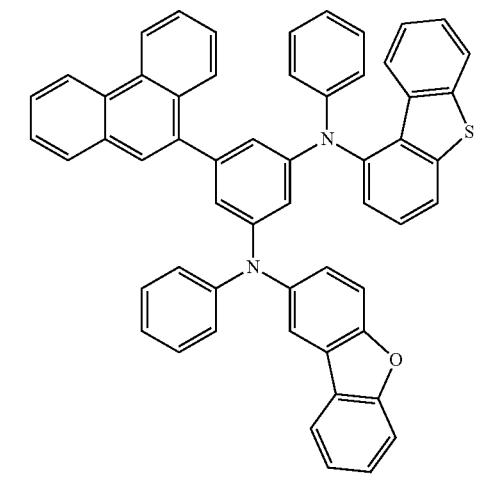
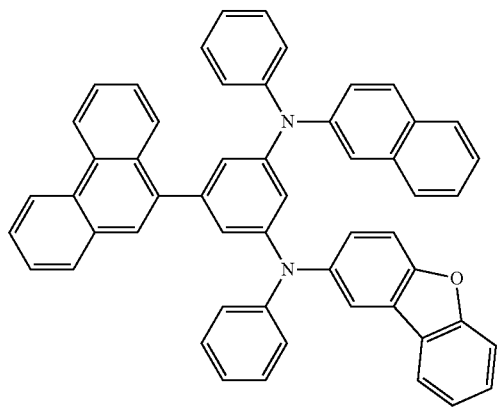

67
-continued
68
-continued
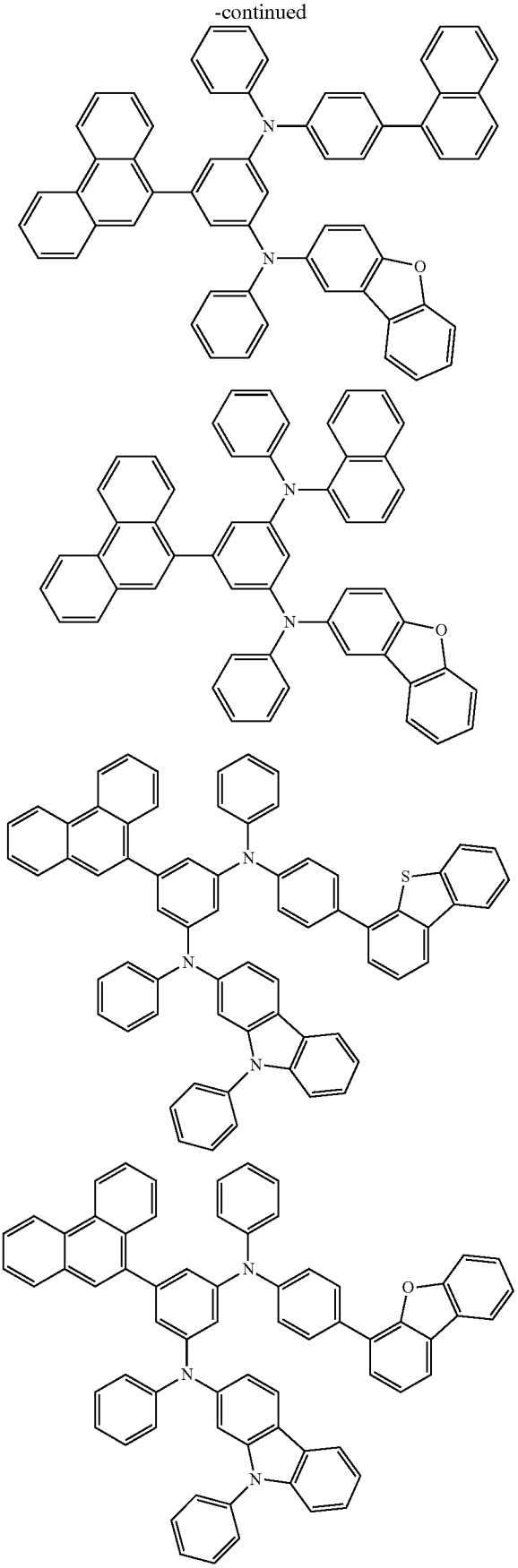
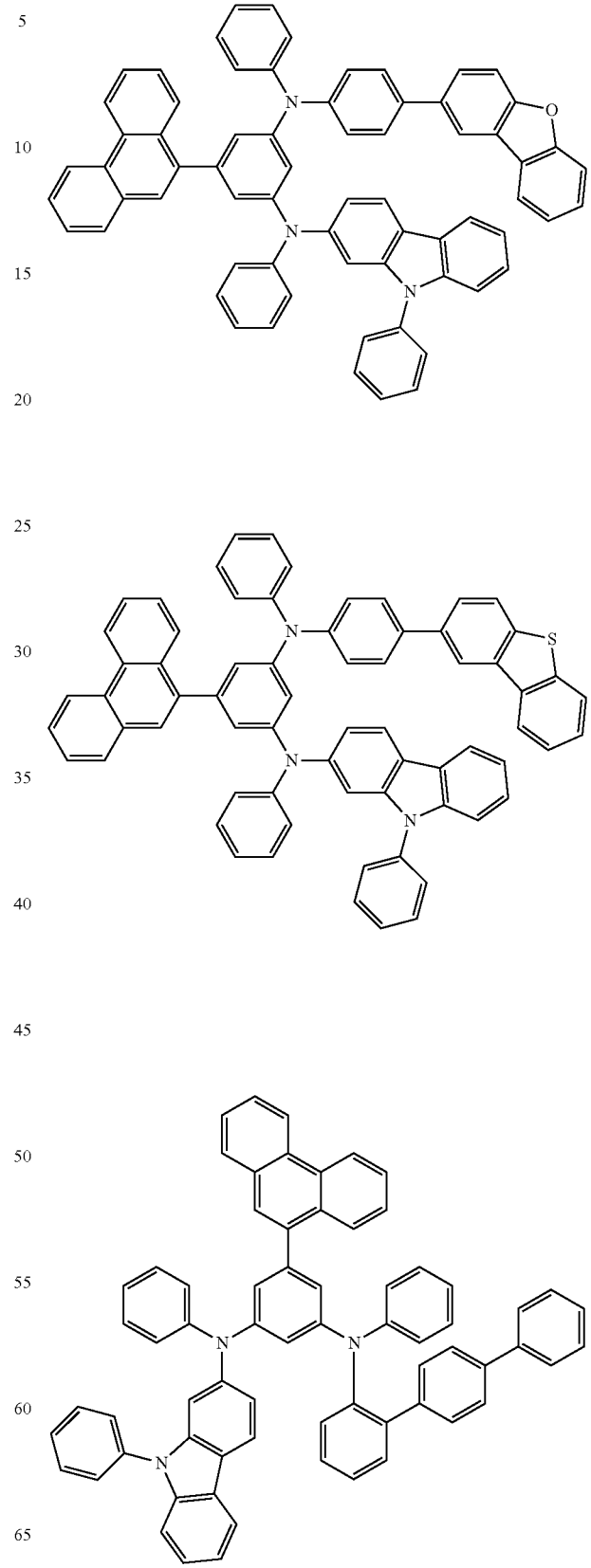

69
-continued
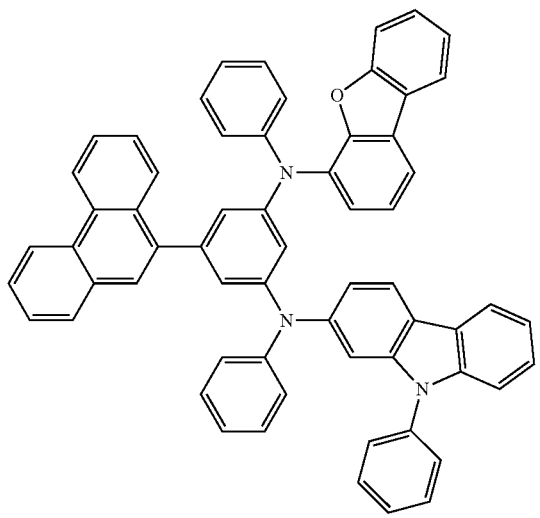
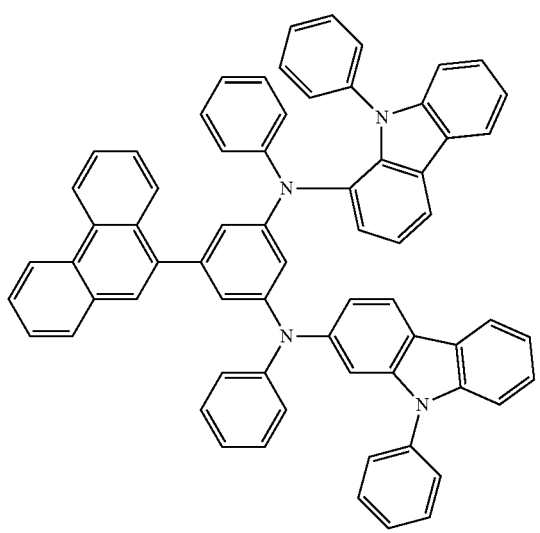
70
-continued
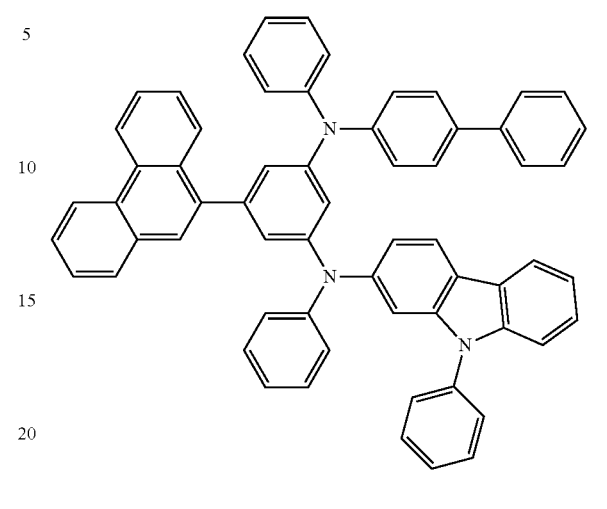
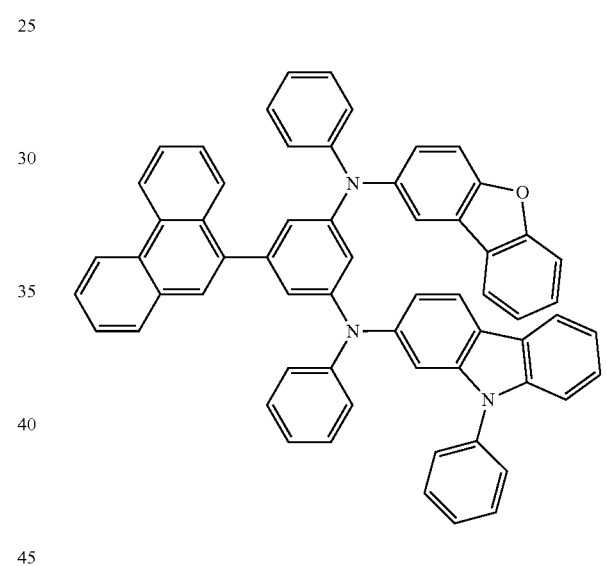
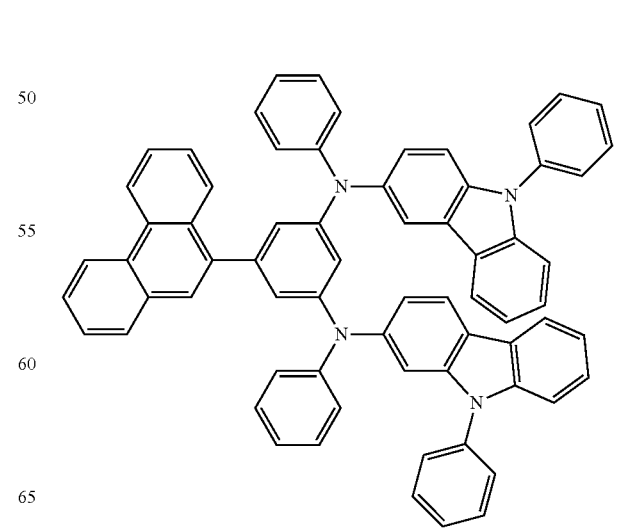

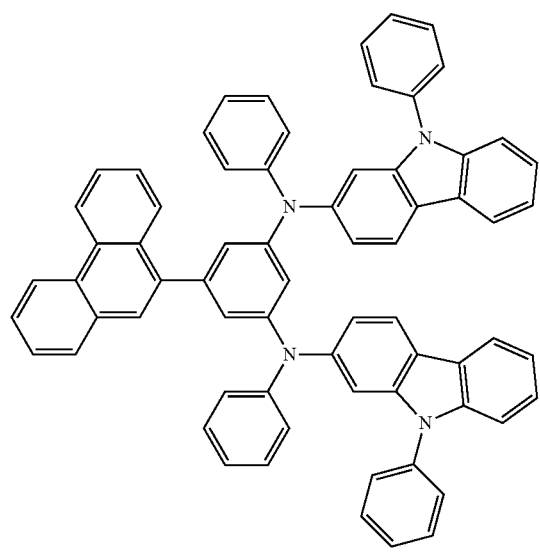
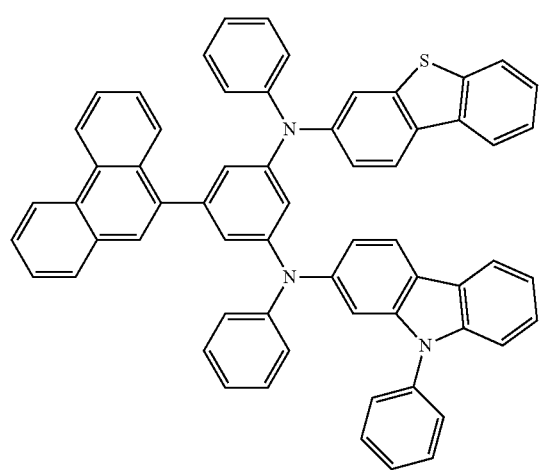
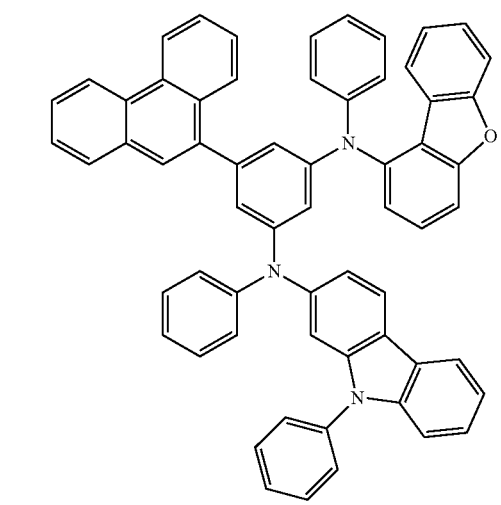
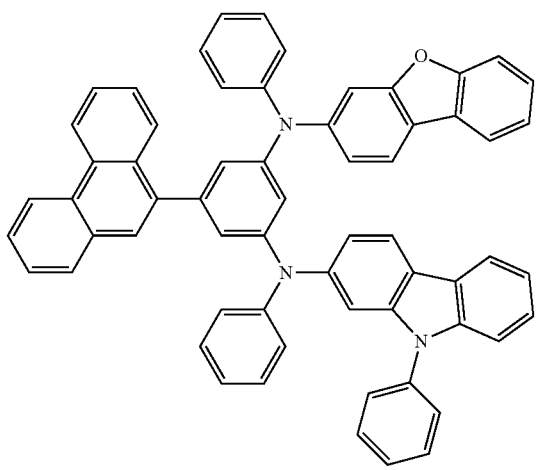
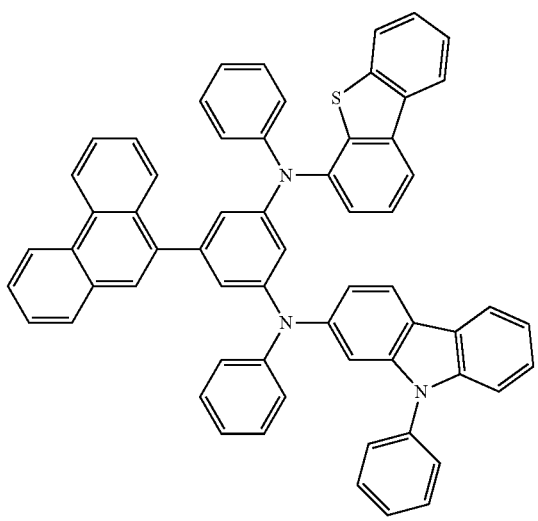
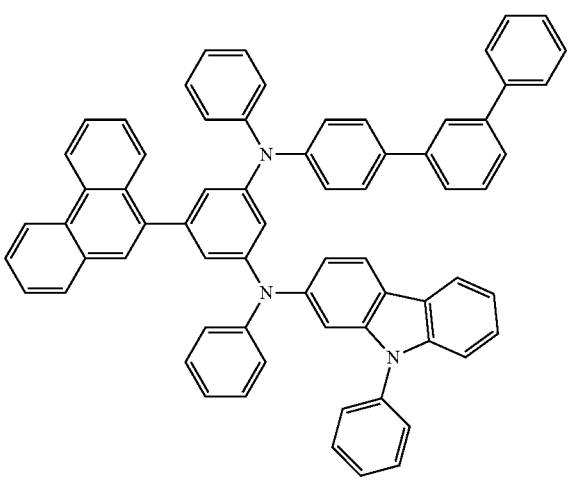

73
-continued
74
-continued
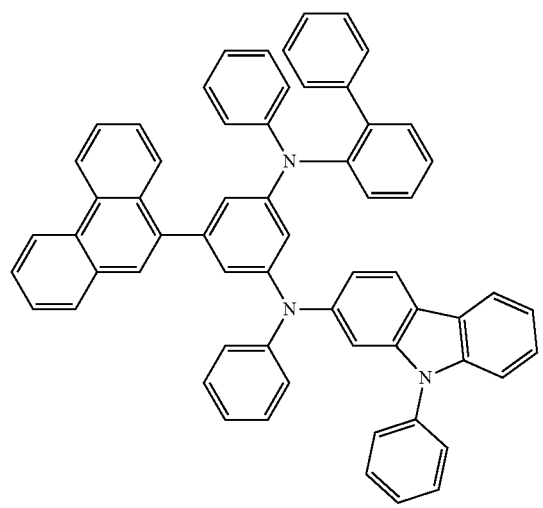
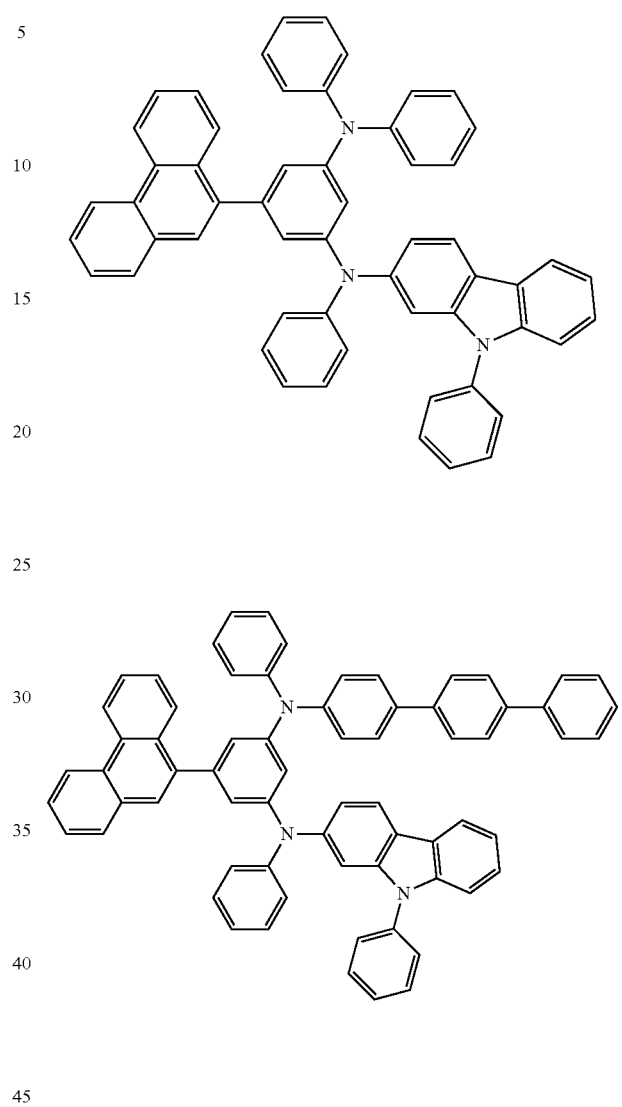
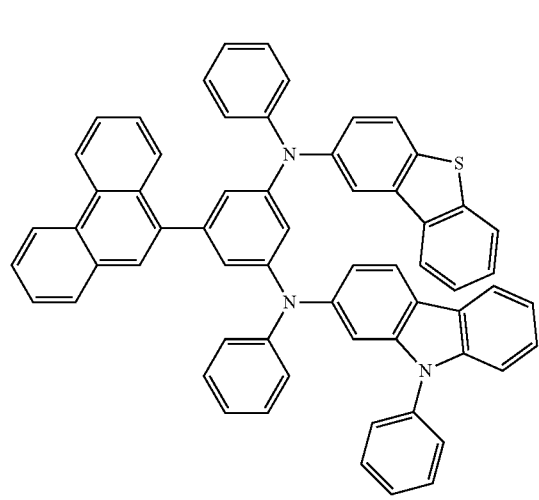
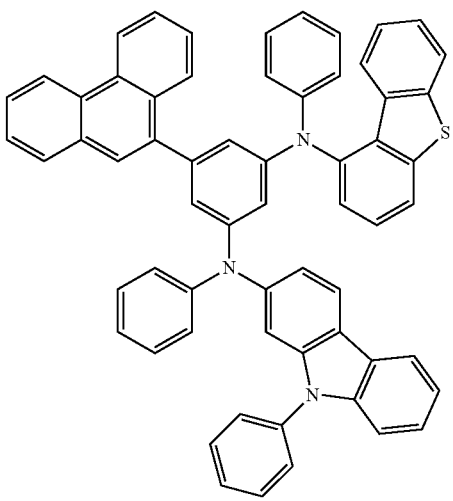

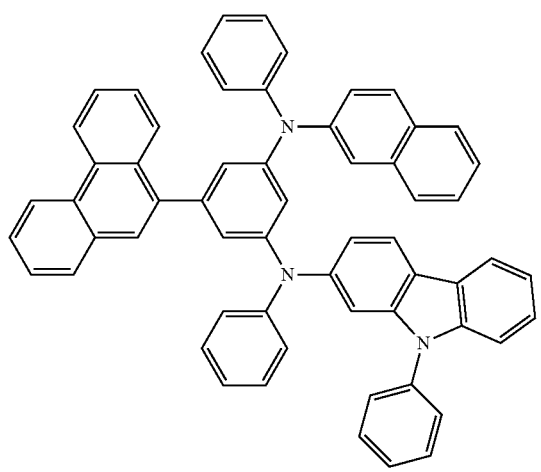
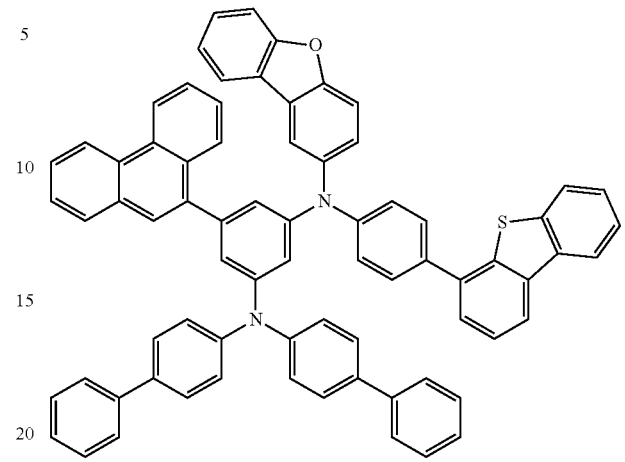
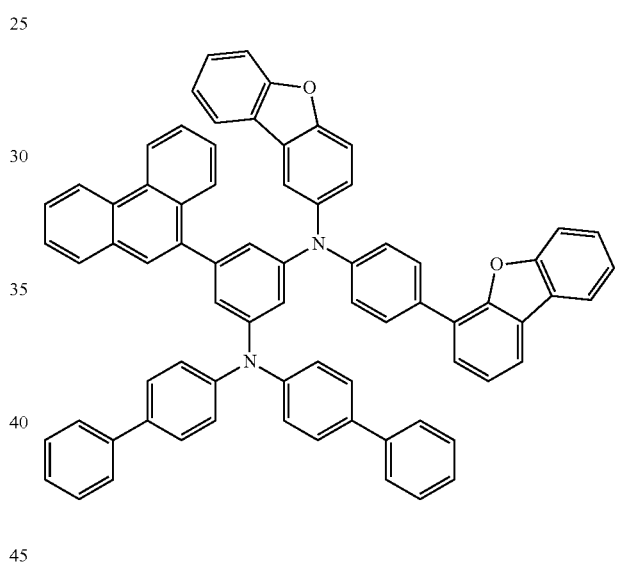
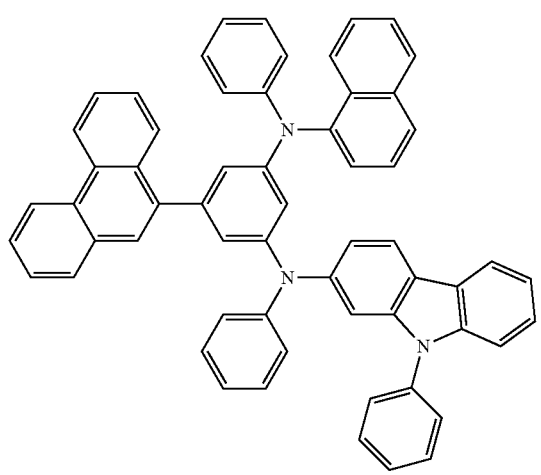
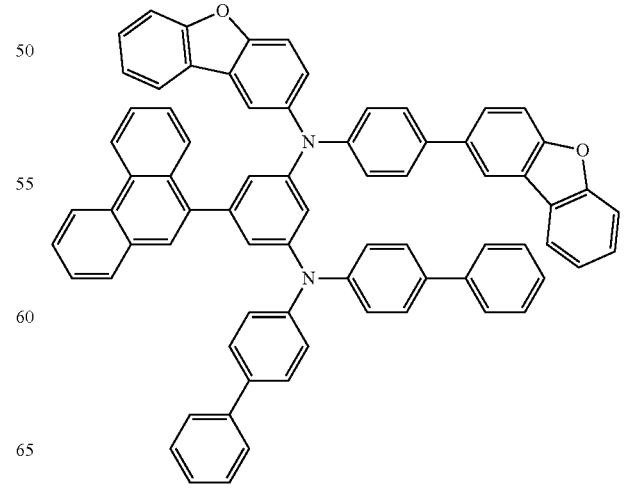

77
-continued
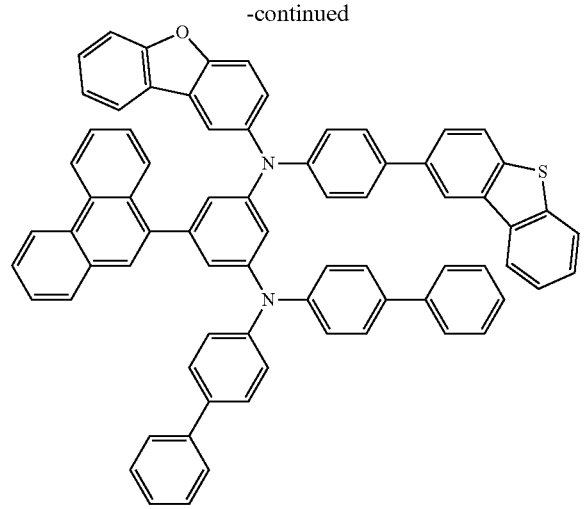
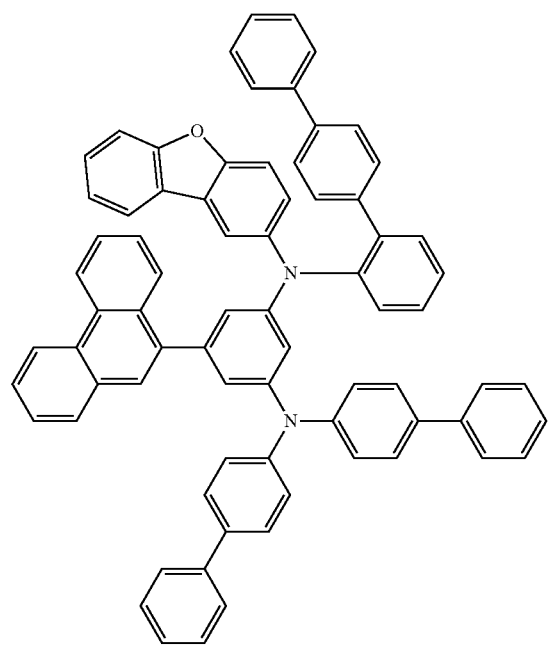
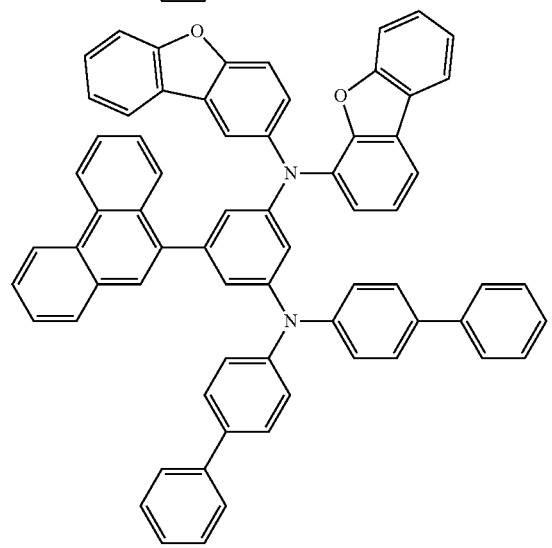
78
-continued
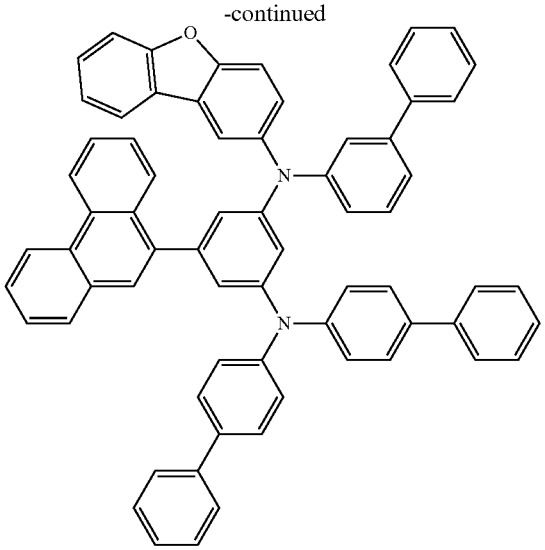
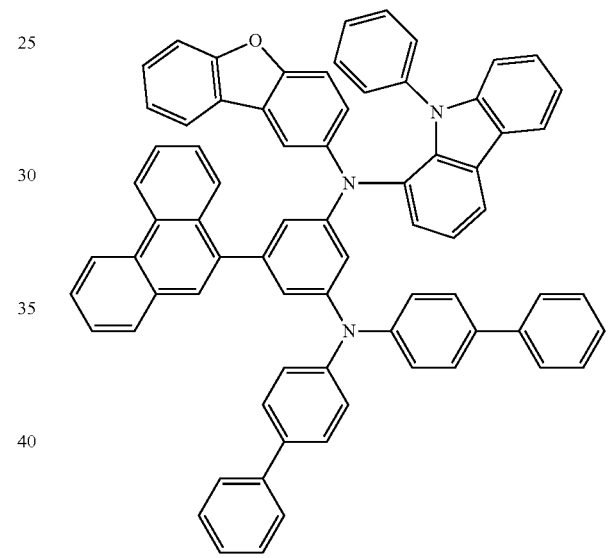
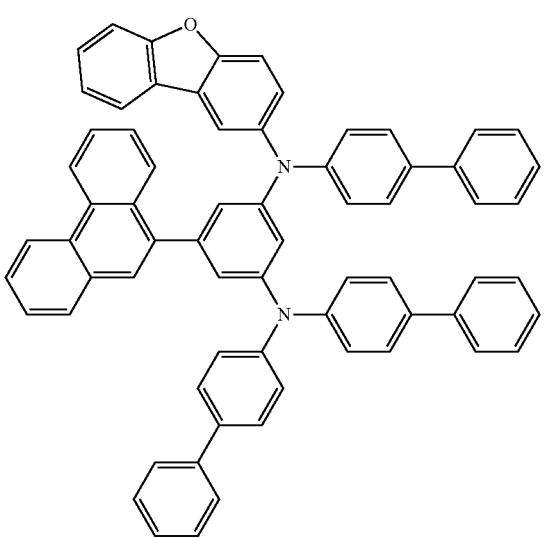

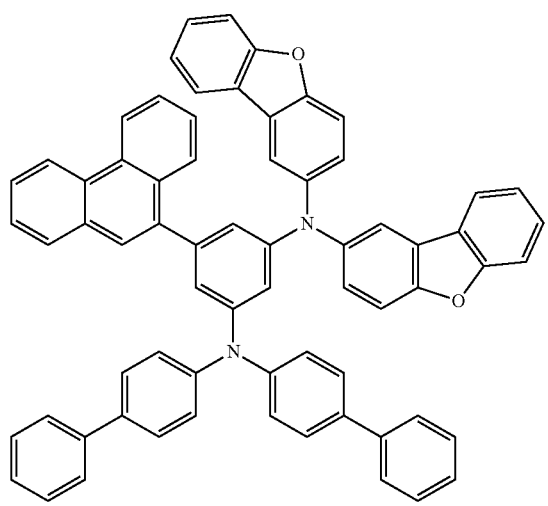
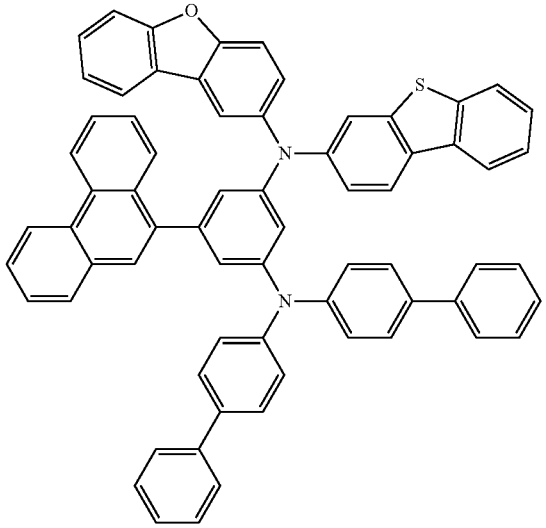
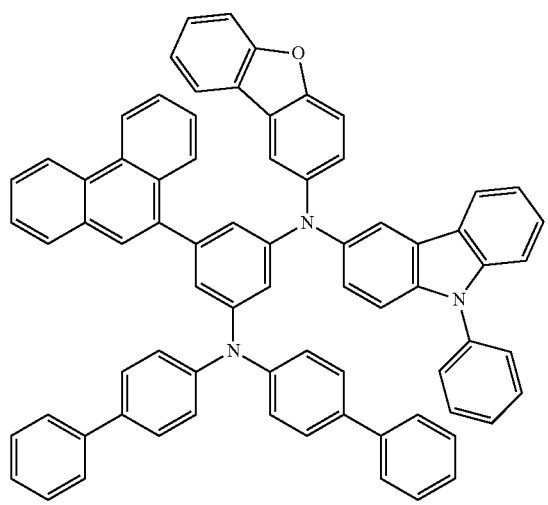
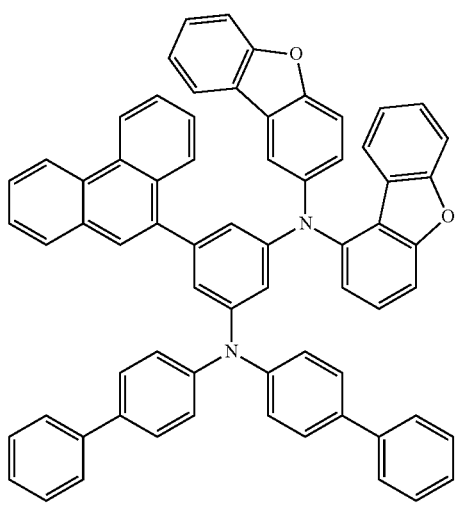
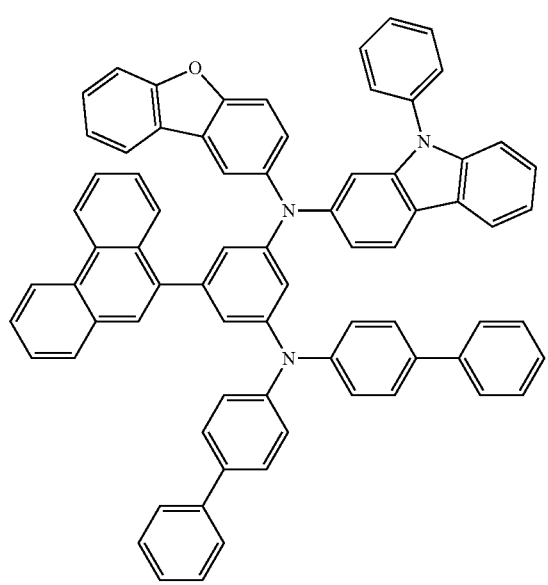

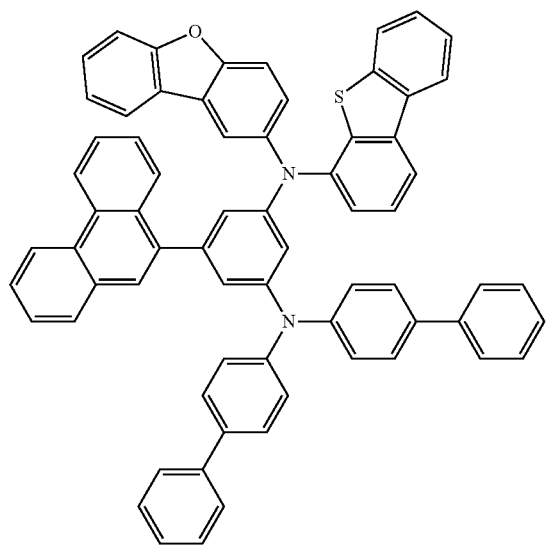
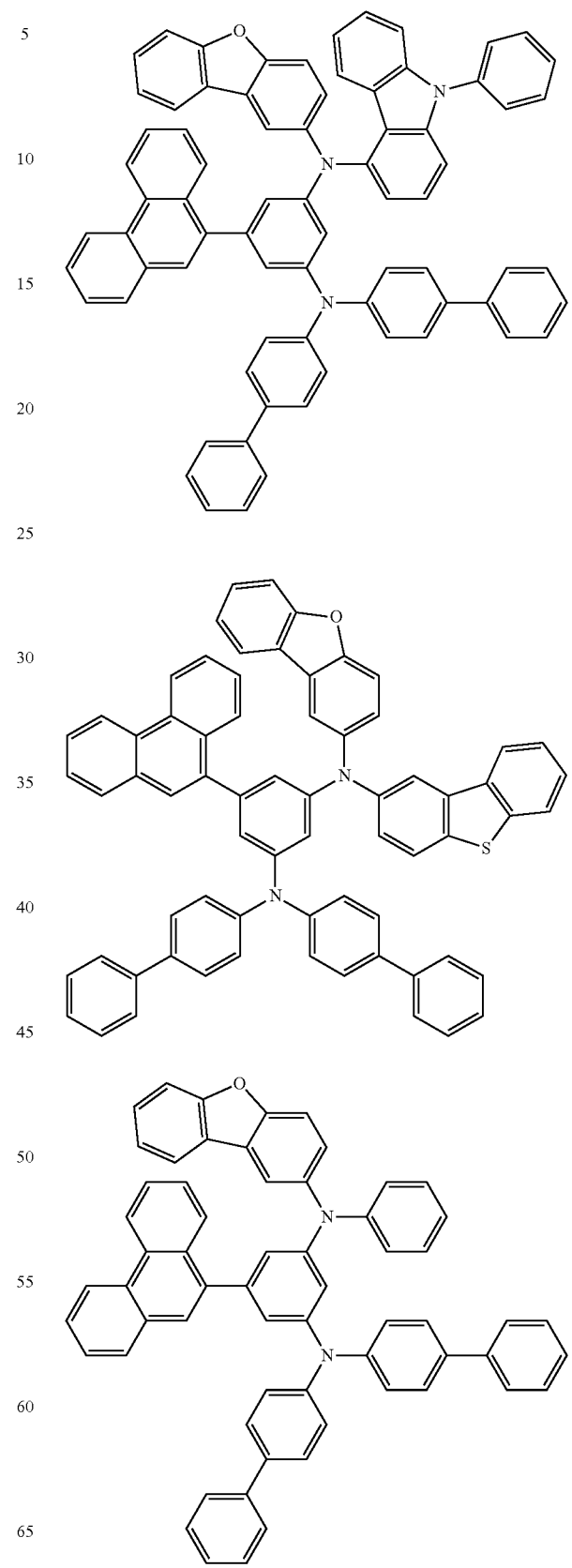

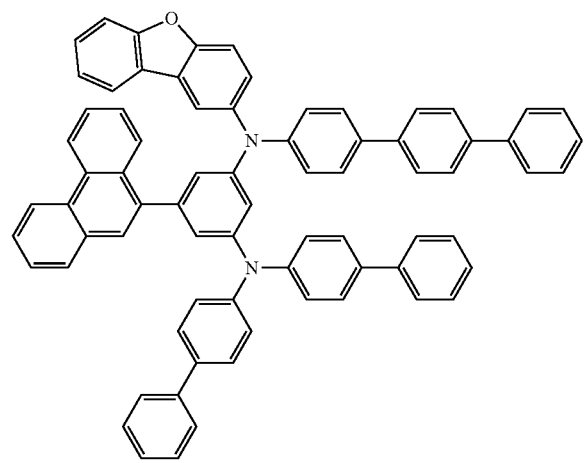
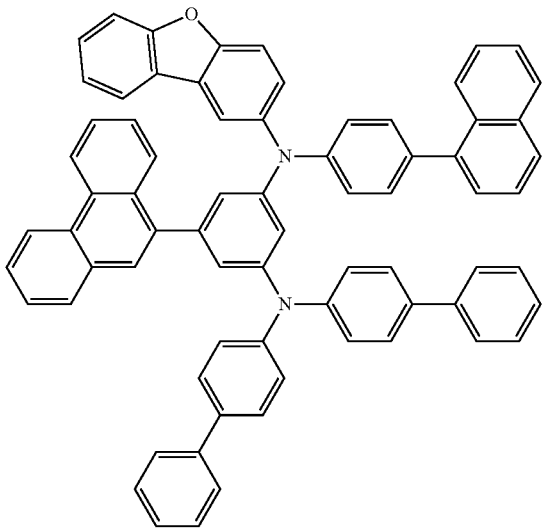
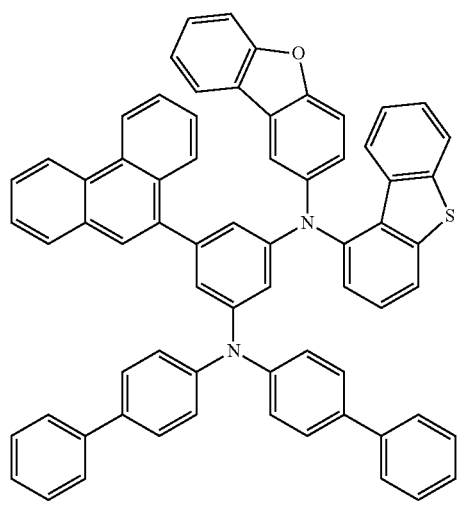
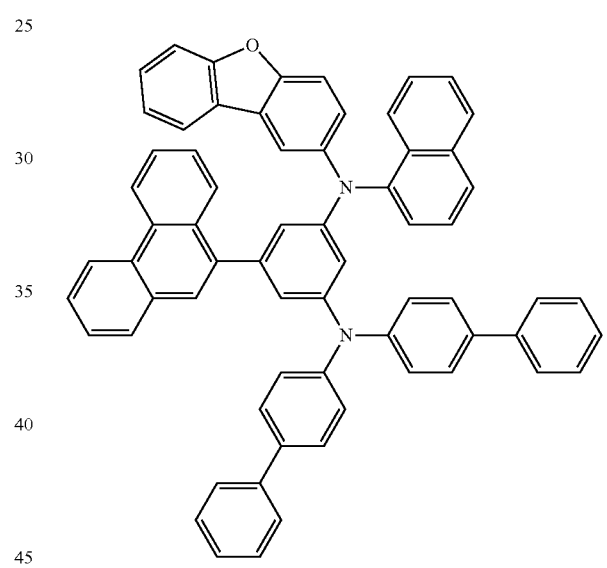
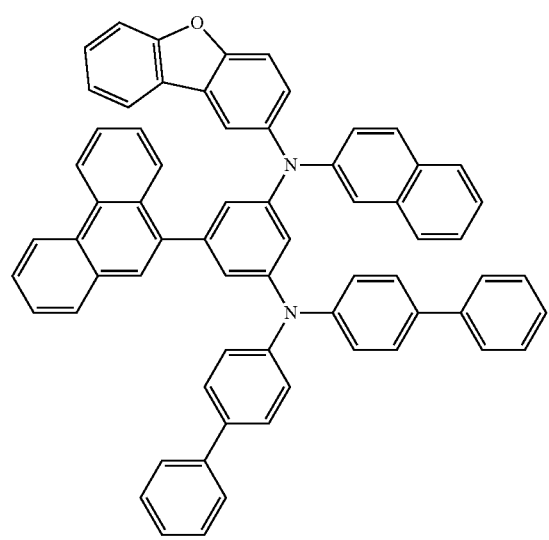
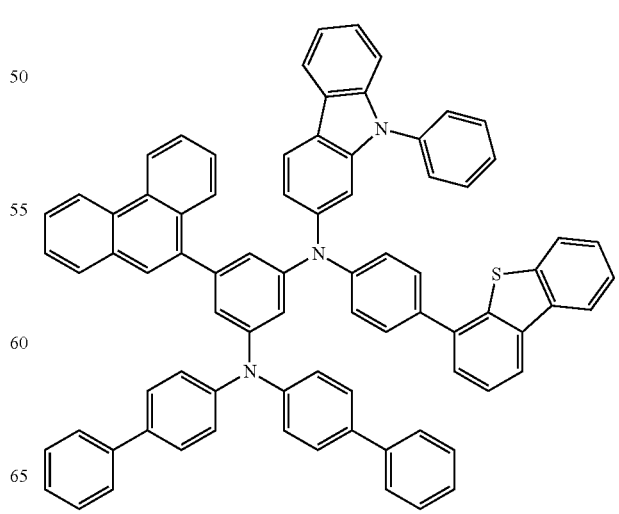

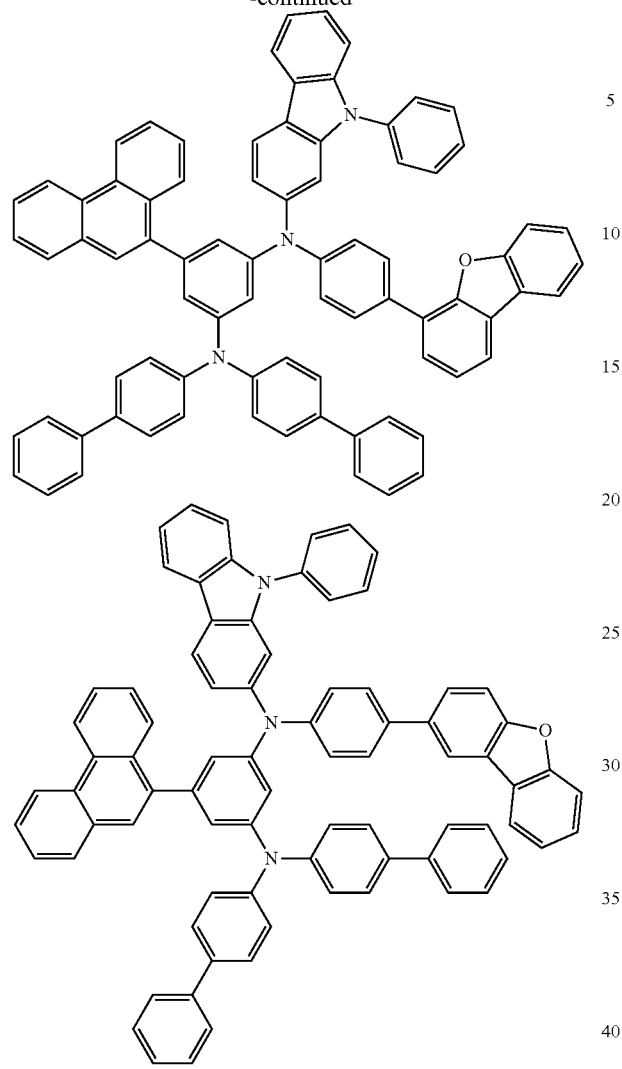
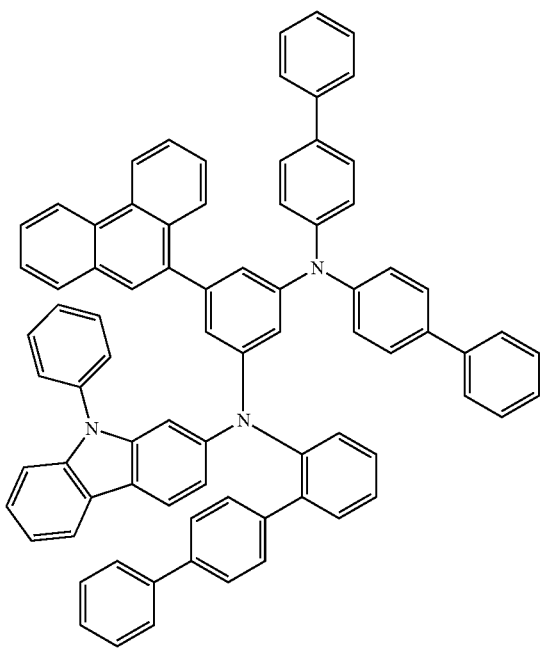
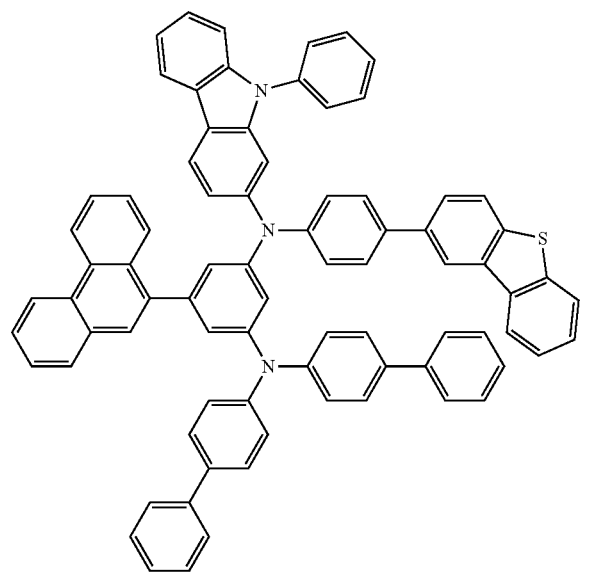
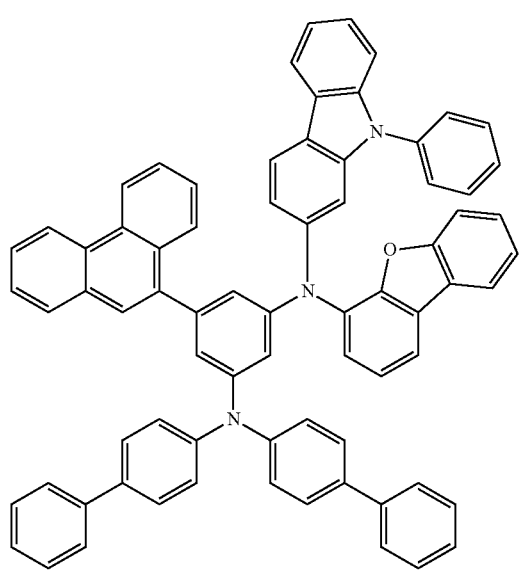

87
-continued
88
-continued
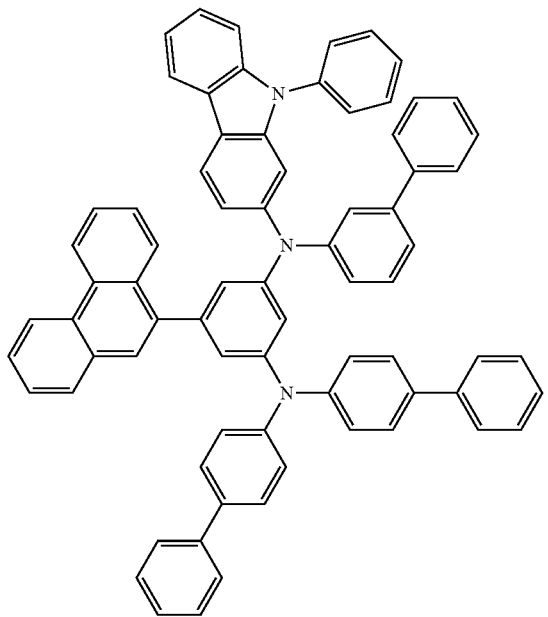
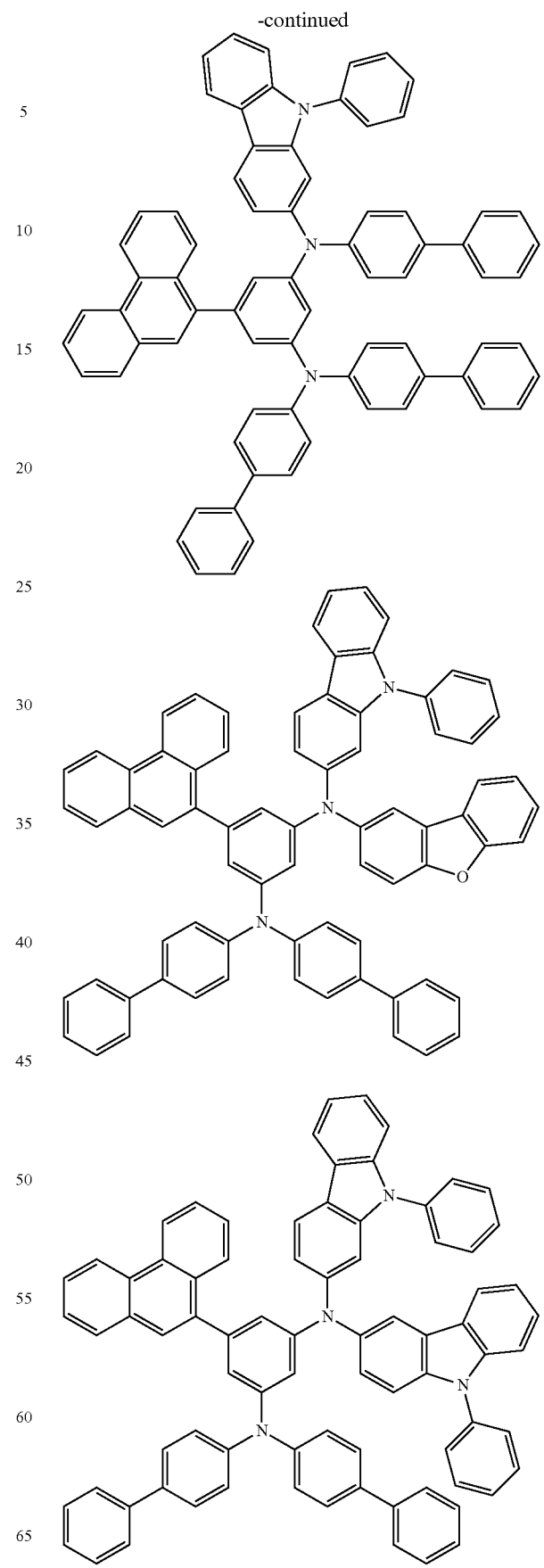

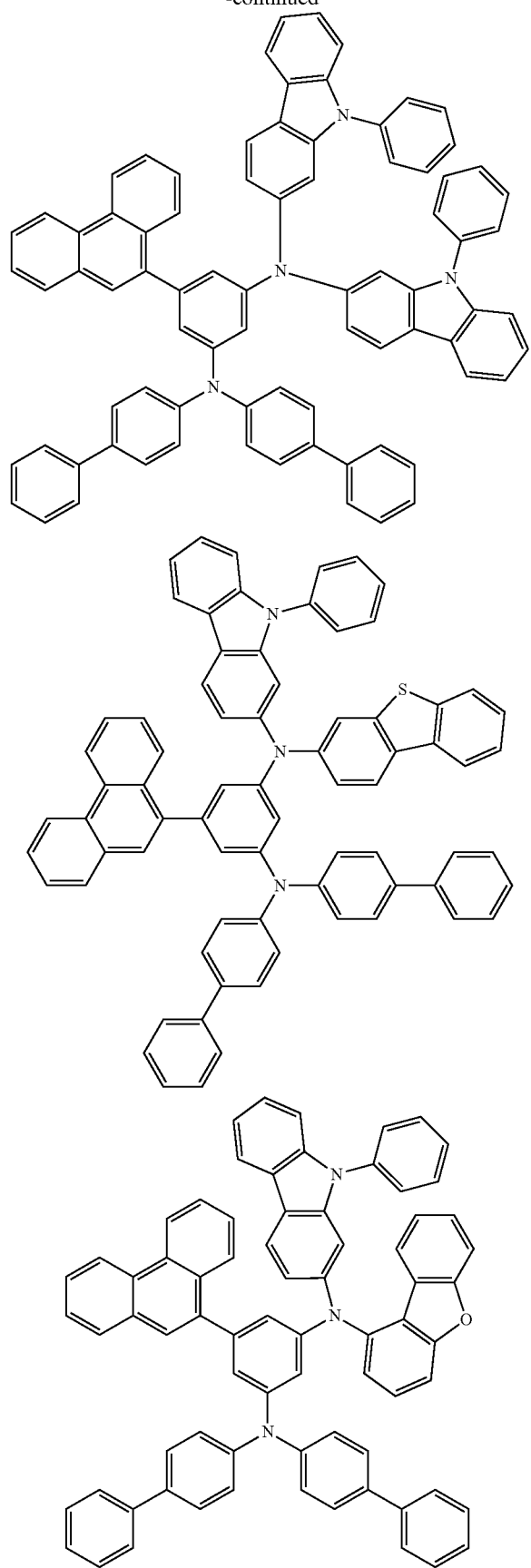
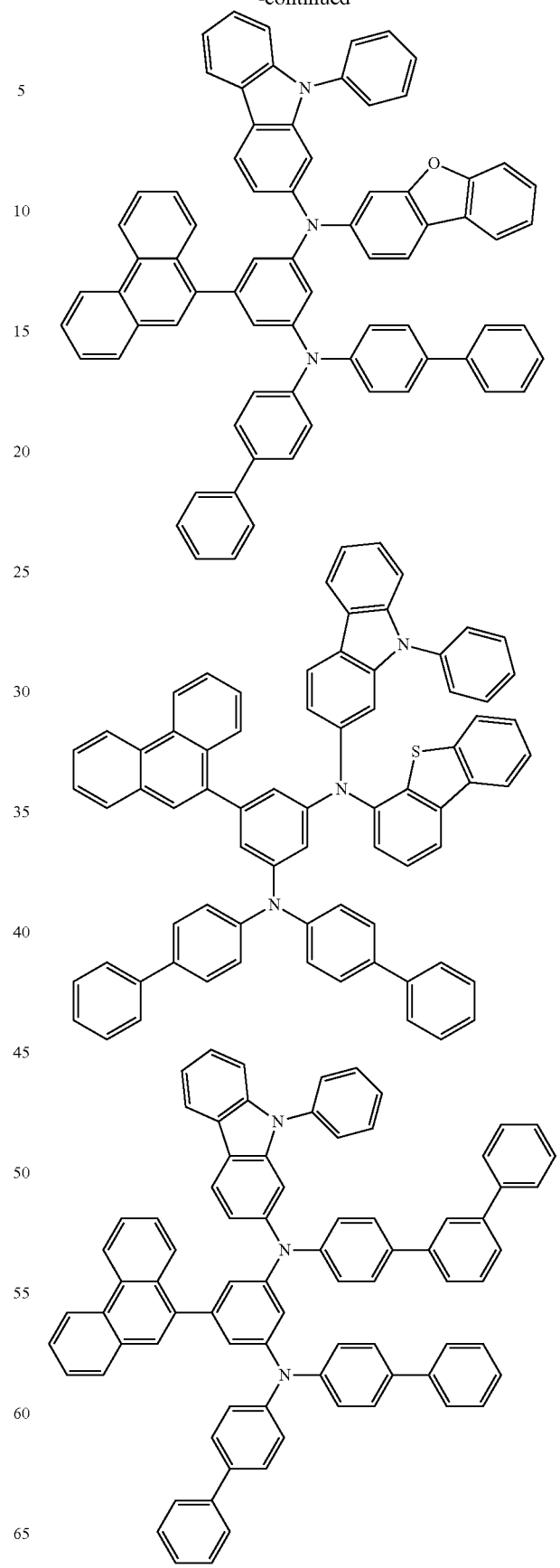

91
-continued
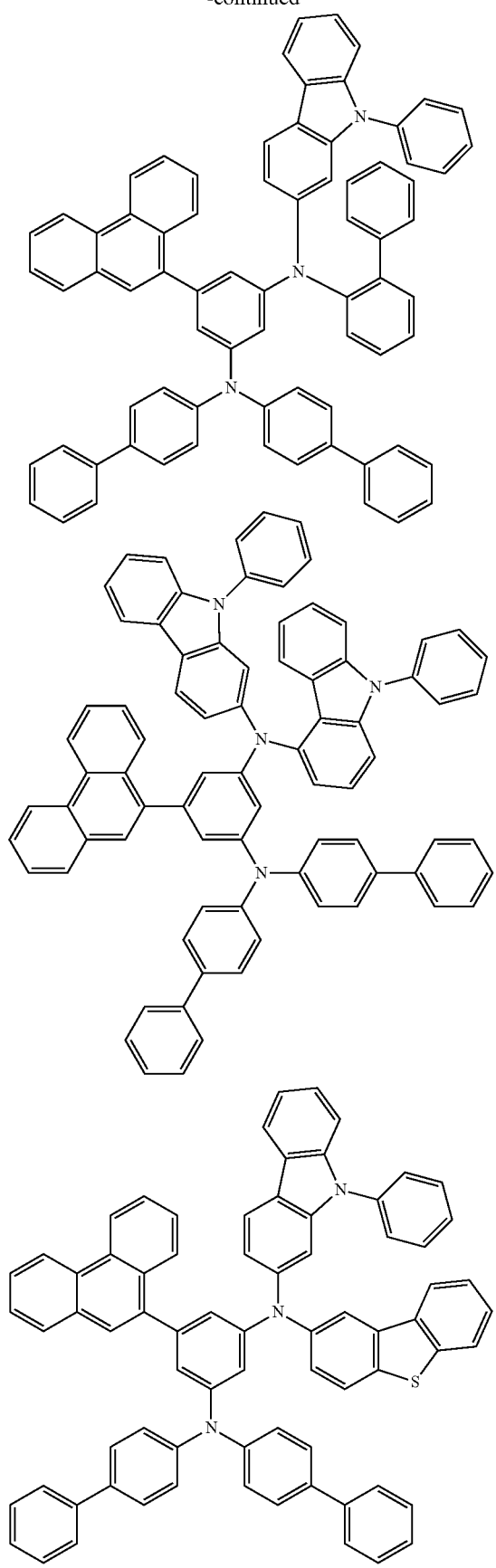
92
-continued
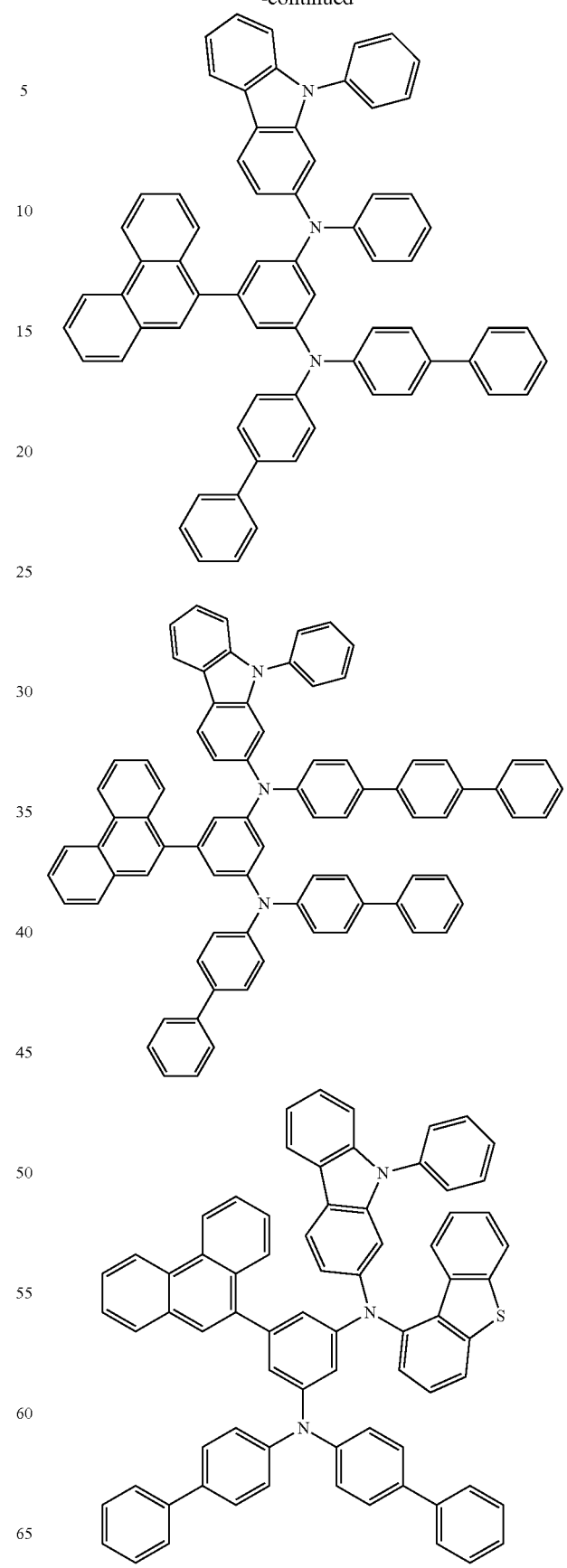

93
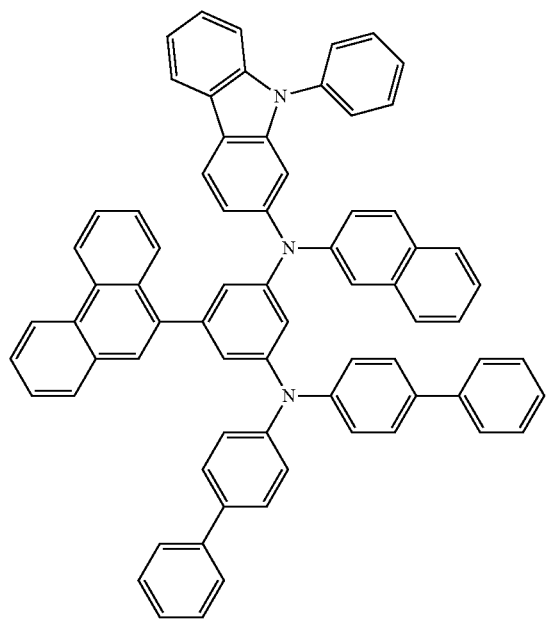
94
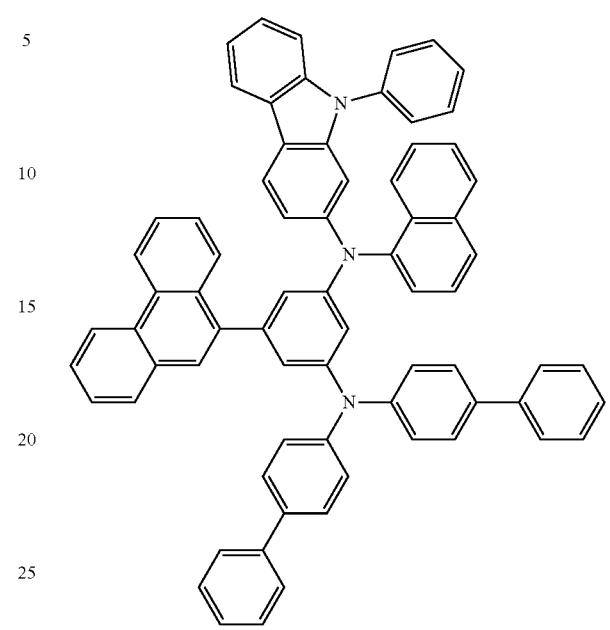
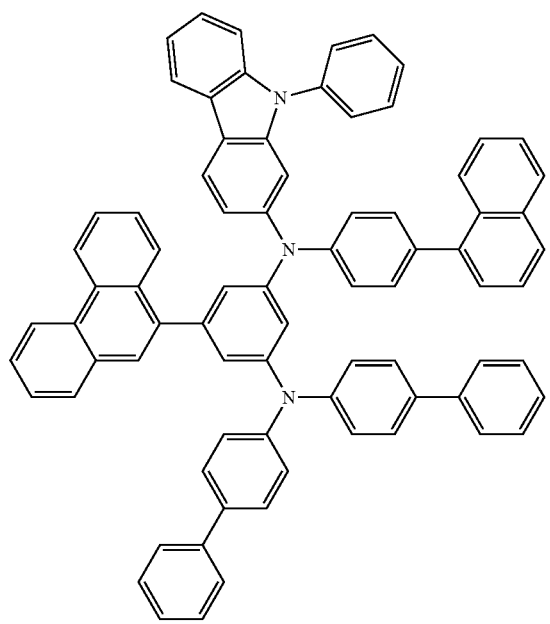
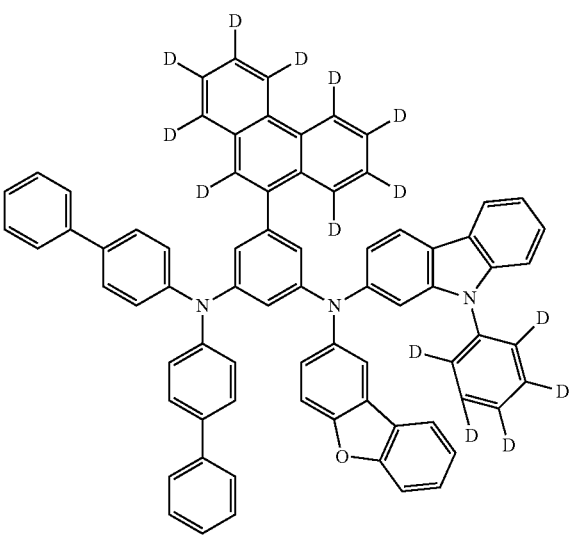

95
-continued
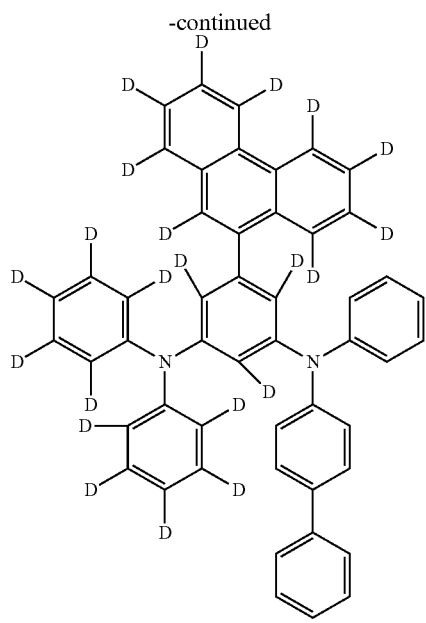
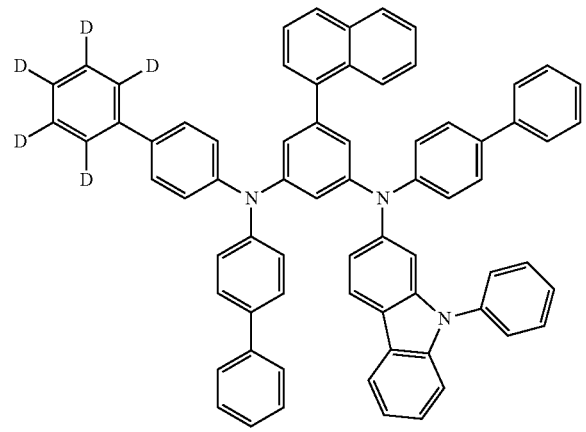
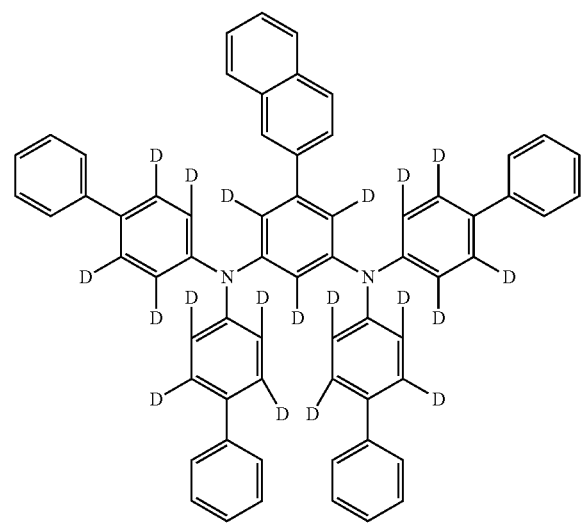
96
-continued
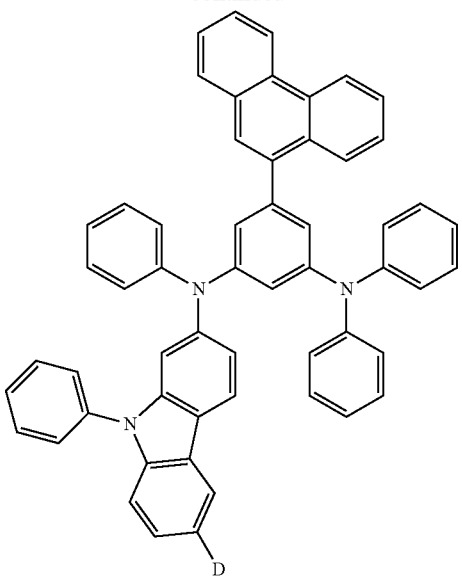
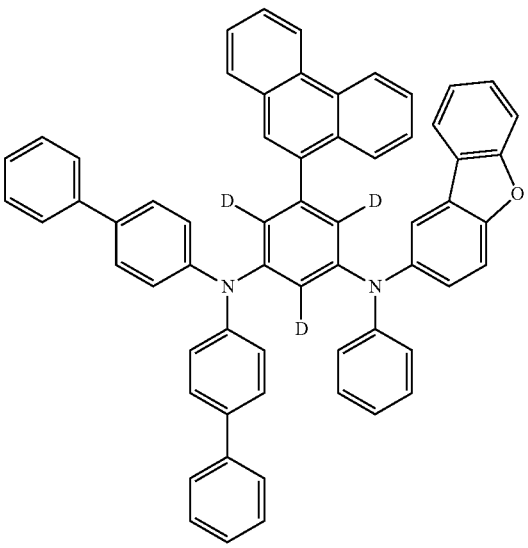

-continued

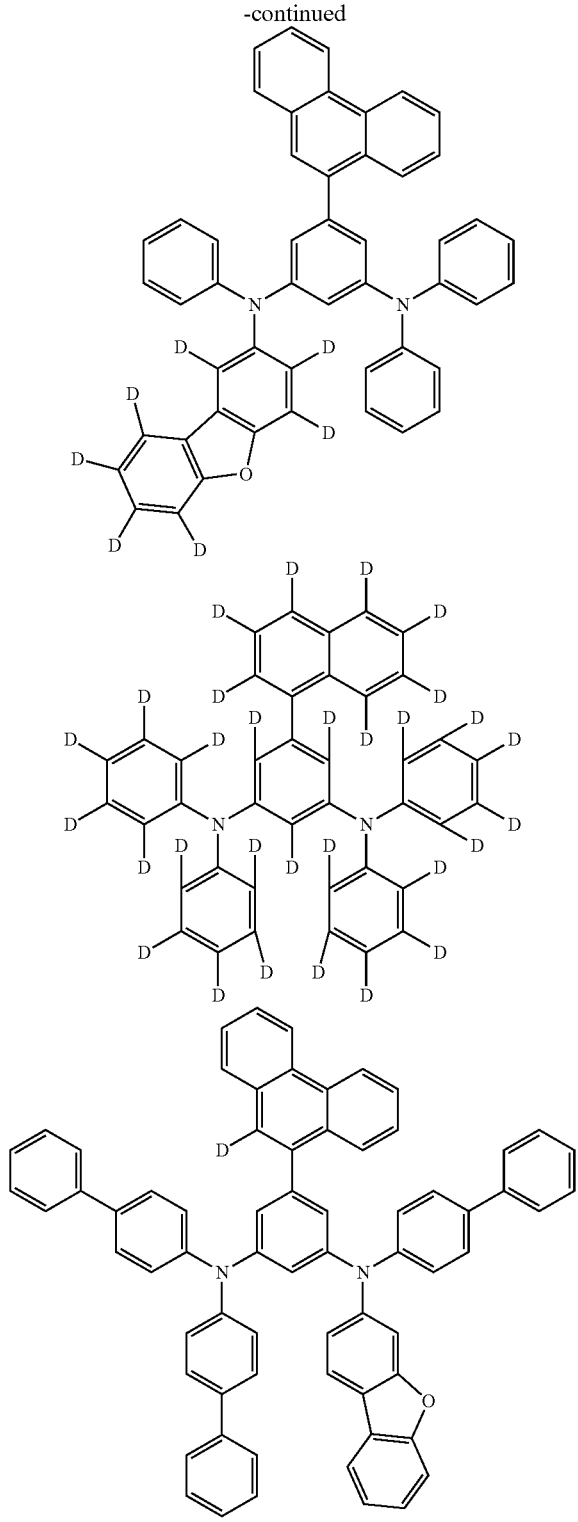

Material for Organic EL Device

The material for the organic EL device of the present invention contains the compound (1). The content of the compound (1) in the material for the organic EL device of the present invention is not particularly limited, and is, for example, 1% by mass or more (including 100%), preferably 10% by mass or more (including 100%), more preferably 50% by mass or more (including 100%), still more prefer- ably 80% by mass or more (including 100%), and especially preferably 90% by mass or more (including 100%). The material for the organic EL device of the present invention is useful in producing the organic EL device.

Organic EL Device

Next, the organic EL device of the present invention is described.

The organic EL device includes an anode, a cathode, and organic layers between the anode and the cathode. The organic layers include a light emitting layer, and at least one layer among the organic layers contains the compound (1).

Examples of the organic layer containing the compound (1) may include a hole transporting zone (a hole injecting layer, a hole transporting layer, an electron blocking layer, an exciton blocking layer, etc.) provided between the anode and the light emitting layer, the light emitting layer, a space layer, an electron transporting zone (an electron injecting layer, an electron transporting layer, a hole blocking layer, etc.) provided between the cathode and the light emitting layer, but are not limited thereto. The compound (1) is preferably used as a material for the hole transporting zone or the light emitting layer in a fluorescent or phosphorescent EL device, more preferably as a material for the hole transporting zone, and still more preferably as a material for the hole transporting layer, the electron blocking layer, or the exciton blocking layer.

The organic EL devices of the present invention may be a fluorescent or phosphorescent light emission-type monochromatic light emitting device or a fluorescent/phosphorescent hybrid-type white light emitting device, and may be a simple type having a single light emitting unit or a tandem type having a plurality of light emitting units. Above all, the fluorescent light emission-type device is preferred. The "light emitting unit" referred to herein refers to a minimum unit that emits light by recombination of injected holes and electrons, which includes organic layers among which at least one layer is a light emitting layer.

For example, as a representative device configuration of the simple type organic EL device, the following device configuration may be exemplified.

(1) Anode/Light Emitting Unit/Cathode

The light emitting unit may be a stacked-type having a plurality of phosphorescent light emitting layers or fluorescent light emitting layers. In this case, a space layer may be provided between the light emitting layers for the purpose of preventing excitons generated in the phosphorescent light emitting layer from diffusing into the fluorescent light emitting layer. Representative layer configurations of the simple type light emitting unit are described below. Layers in parentheses are optional.

(a) (hole injecting layer/) hole transporting layer/fluorescent light emitting layer (/electron transporting layer/ electron injecting layer)

(b) (hole injecting layer/) hole transporting layer/phosphorescent light emitting layer (/electron transporting layer/electron injecting layer)

(c) (hole injecting layer/) hole transporting layer/first fluorescent light emitting layer/second fluorescent light emitting layer (/electron transporting layer/electron injecting layer)

(d) (hole injecting layer/) hole transporting layer/first phosphorescent light emitting layer/second phosphorescent light emitting layer (/electron transporting layer/electron injecting layer)

(e) (hole injecting layer/) hole transporting layer/phosphorescent light emitting layer/space layer/fluorescent light emitting layer (/electron transporting layer/electron injecting layer)
(f) (hole injecting layer/) hole transporting layer/first phosphorescent light emitting layer/second phosphorescent light emitting layer/space layer/fluorescent light emitting layer (/electron transporting layer/electron injecting layer)
(g) (hole injecting layer/) hole transporting layer/first phosphorescent light emitting layer/space layer/second phosphorescent light emitting layer/space layer/fluorescent light emitting layer (/electron transporting layer/electron injecting layer)
(h) (hole injecting layer/) hole transporting layer/phosphorescent light emitting layer/space layer/first fluorescent light emitting layer/second fluorescent light emitting layer (/electron transporting layer/electron injecting layer)
(i) (hole injecting layer/) hole transporting layer/electron blocking layer/fluorescent light emitting layer (/electron transporting layer/electron injecting layer)
(j) (hole injecting layer/) hole transporting layer/electron blocking layer/phosphorescent light emitting layer (/electron transporting layer/electron injecting layer)
(k) (hole injecting layer/) hole transporting layer/exciton blocking layer/fluorescent light emitting layer (/electron transporting layer/electron injecting layer)
(l) (hole injecting layer/) hole transporting layer/exciton blocking layer/phosphorescent light emitting layer (/electron transporting layer/electron injecting layer)
(m) (hole injecting layer/) first hole transporting layer/second hole transporting layer/fluorescent light emitting layer (/electron transporting layer/electron injecting layer)
(n) (hole injecting layer/) first hole transporting layer/second hole transporting layer/phosphorescent light emitting layer (/electron transporting layer/electron injecting layer)
(o) (hole injecting layer/) first hole transporting layer/second hole transporting layer/fluorescent light emitting layer/first electron transporting layer/second electron transporting layer (/electron injecting layer)
(p) (hole injecting layer/) first hole transporting layer/second hole transporting layer/phosphorescent light emitting layer/first electron transporting layer/second electron transporting layer (/electron injecting layer)
(q) (hole injecting layer/) hole transporting layer/fluorescent light emitting layer/hole blocking layer (/electron transporting layer/electron injecting layer)
(r) (hole injecting layer/) hole transporting layer/phosphorescent light emitting layer/hole blocking layer (/electron transporting layer/electron injecting layer)
(s) (hole injecting layer/) hole transporting layer/fluorescent light emitting layer/exciton blocking layer (/electron transporting layer/electron injecting layer)
(t) (hole injecting layer/) hole transporting layer/phosphorescent light emitting layer/exciton blocking layer (/electron transporting layer/electron injecting layer)

The phosphorescent and fluorescent light emitting layers may emit emission colors different from each other, respectively. Specifically, in the stacked light emitting unit (f), a layer configuration, such as (hole injecting layer/) hole transporting layer/first phosphorescent light emitting layer (red light emission)/second phosphorescent light emitting layer (green light emission)/space layer/fluorescent light emitting layer (blue light emission)/electron transporting layer, may be exemplified.

An electron blocking layer may be properly provided between each light emitting layer and the hole transporting layer or the space layer. Also, a hole blocking layer may be properly provided between each light emitting layer and the electron transporting layer. The employment of the electron blocking layer or the hole blocking layer allows to improve the emission efficiency by trapping electrons or holes within the light emitting layer and increasing the probability of charge recombination in the light emitting layer.

As a representative device configuration of the tandem type organic EL device, the following device configuration may be exemplified.

(2) Anode/First Light Emitting Unit/Intermediate Layer/Second Light Emitting Unit/Cathode Here, for example, each of the first light emitting unit and second light emitting unit may be independently selected from the above-described light emitting units.

The intermediate layer is also generally referred to as an intermediate electrode, an intermediate conductive layer, a charge generation layer, an electron withdrawing layer, a connecting layer, or an intermediate insulating layer, and a known material configuration can be used, in which electrons are supplied to the first light emitting unit, and holes are supplied to the second light emitting unit.

FIG. 1 is a schematic view illustrating an example of a configuration of the organic EL device of the present invention. The organic EL device 1 of this example includes a substrate 2, an anode 3, a cathode 4, and a light emitting unit 10 disposed between the anode 3 and the cathode 4. The light emitting unit 10 includes a light emitting layer 5. A hole transporting zone 6 (a hole injecting layer, a hole transporting layer, etc.) is provided between the light emitting layer 5 and the anode 3, and an electron transporting zone 7 (an electron injecting layer, an electron transporting layer, etc.) is provided between the light emitting layer 5 and the cathode 4. In addition, an electron blocking layer (not shown) may be provided on the side of the anode 3 of the light emitting layer 5, and a hole blocking layer (not shown) may be provided on the side of the cathode 4 of the light emitting layer 5. According to this, electrons and holes are trapped in the light emitting layer 5, thereby enabling one to further increase the production efficiency of excitons in the light emitting layer 5.

Figure 2:
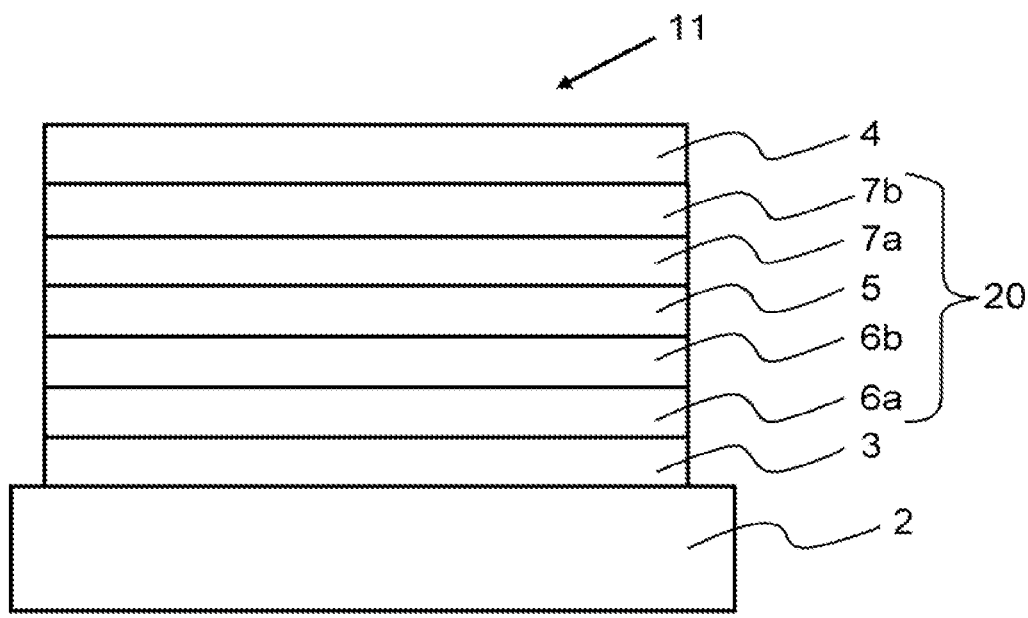
FIG. 2 is a schematic view illustrating another example of a layer configuration of an organic EL device according to an embodiment of the present invention.

FIG. 2 is a schematic view illustrating another configuration of the organic EL device of the present invention. An organic EL device 11 includes the substrate 2, the anode 3, the cathode 4, and a light emitting unit 20 disposed between the anode 3 and the cathode 4. The light emitting unit 20 includes the light emitting layer 5. A hole transporting zone disposed between the anode 3 and the light emitting layer 5 is formed of a first hole transporting layer 6a and a second hole transporting layer 6b. In addition, an electron transporting zone disposed between the light emitting layer 5 and the cathode 4 is formed of a first electron transporting layer 7a and a second electron transporting layer 7b.

In the present invention, a host combined with a fluorescent dopant (a fluorescent emitting material) is called a fluorescent host, and a host combined with a phosphorescent dopant is called a phosphorescent host. The fluorescent host and the phosphorescent host are not distinguished from each other merely by their molecular structures. That is, the phosphorescent host means a material that forms a phosphorescent light emitting layer containing a phosphorescent dopant, but does not mean unavailability as a material that forms a fluorescent light emitting layer. The same also applies to the fluorescent host.

Substrate

The substrate is used as a support of the organic EL device. Examples of the substrate include a plate of glass, quartz, and plastic. In addition, a flexible substrate may be used. Examples of the flexible substrate include a plastic substrate made of polycarbonate, polyarylate, polyether sulfone, polypropylene, polyester, polyvinyl fluoride, or polyvinyl chloride. In addition, an inorganic vapor deposition film can be used.

Anode

It is preferred that a metal, an alloy, an electrically conductive compound, or a mixture thereof which has a high work function (specifically 4.0 eV or more) is used for the anode formed on the substrate. Specific examples thereof include indium oxide-tin oxide (ITO: Indium Tin Oxide), indium oxide-tin oxide containing silicon or silicon oxide, indium oxide-zinc oxide, indium oxide containing tungsten oxide and zinc oxide, and graphene. Besides, examples there include gold (Au), platinum (Pt), nickel (Ni), tungsten (W), chromium (Cr), molybdenum (Mo), iron (Fe), cobalt (Co), copper (Cu), palladium (Pd), titanium (Ti), or nitrides of the metals (for example, titanium nitride).

These materials are usually deposited by a sputtering method. For example, through a sputtering method, it is possible to form indium oxide-zinc oxide by using a target in which 1 to 10 wt % of zinc oxide is added to indium oxide, and to form indium oxide containing tungsten oxide and zinc oxide by using a target containing 0.5 to 5 wt % of tungsten oxide and 0.1 to 1 wt % of zinc oxide with respect to indium oxide. Besides, the manufacturing may be performed by a vacuum vapor deposition method, a coating method, an inkjet method, a spin coating method, etc.

The hole injecting layer formed in contact with the anode is formed by using a material that facilitates hole injection regardless of a work function of the anode, and thus, it is possible to use materials generally used as an electrode material (for example, metals, alloys, electrically conductive compounds, or mixtures thereof, elements belonging to Group 1 or 2 of the periodic table of the elements).

It is also possible to use elements belonging to Group 1 or 2 of the periodic table of the elements, which are materials having low work functions, that is, alkali metals, such as lithium (Li) and cesium (Cs), alkaline earth metals, such as magnesium (Mg), calcium (Ca), and strontium (Sr), and alloys containing these (for example, MgAg, AlLi), and rare earth metals, such as europium (Eu), and ytterbium (Yb) and alloys containing these. When the anode is formed by using the alkali metals, the alkaline earth metals, and alloys containing these, a vacuum vapor deposition method or a sputtering method can be used. Further, when a silver paste or the like is used, a coating method, an inkjet method, etc. can be used.

Hole Injecting Layer

The hole injecting layer is a layer containing a material having a high hole injection ability (a hole injecting material). The compound (1) may be used alone or in combination with the following material for the hole injection layer.

As other hole injecting material than the compound (1), molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, and the like can be used.

Examples of the hole injecting layer material also include aromatic amine compounds as low-molecular weight organic compounds, such as 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

High-molecular weight compounds (oligomers, dendrimers, polymers, etc.) may also be used. Examples thereof include high-molecular weight compounds, such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). In addition, high-molecular weight compounds to which an acid is added, such as poly(3,4-ethylenedioxythiophene)/poly (styrene sulfonic acid) (PEDOT/PSS), and polyaniline/poly (styrenesulfonic acid) (PAni/PSS), can also be used.

Furthermore, it is also preferred to use an acceptor material, such as a hexaazatriphenylene (HAT) compound represented by formula (K), in combination with the compound (1).

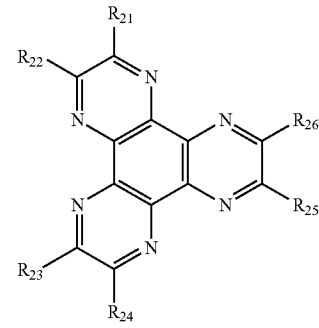

(K)

In the aforementioned formula, $R_{21}$ to $R_{26}$ each independently represent a cyano group, —$CONH_2$, a carboxy group, or —$COOR_{27}$ ($R_{27}$ represents an alkyl group having 1 to 20 carbon atoms or a cycloalkyl group having 3 to 20 carbon atoms). In addition, adjacent two selected from $R_{21}$ and $R_{22}$, $R_{23}$ and $R_{24}$, and $R_{25}$ and $R_{26}$ may be bonded to each other to form a group represented by —CO—O—CO—.

Examples of $R_{27}$ include a methyl group, an ethyl group, an n-propyl group, an isopropyl group, an n-butyl group, an isobutyl group, a t-butyl group, a cyclopentyl group, and a cyclohexyl group.

Hole Transporting Layer

The hole transporting layer is a layer containing a material having a high hole transporting ability (a hole transporting material) and is provided between the anode and the light emitting layer, or between the hole injecting layer and the light emitting layer. It is preferred to use the compound (1) alone or in combination with the following compound for the hole transporting layer.

As other hole transporting material than the compound (1), for example, an aromatic amine compound, a carbazole derivative, an anthracene derivative, and the like can be used.

Examples of the aromatic amine compound include 4,4'-bis[N-(1-naphthyl)-N-phenylamino]biphenyl (abbreviation: NPB) or N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). The aforementioned compounds have a hole mobility of $10^{-6}$ cm$^2$/Vs or more.

Examples of the carbazole derivative include 4,4'-di(9-carbazolyl)biphenyl (abbreviation: CBP), 9-[4-(9-carbazolyl)phenyl]-10-phenylanthracene (abbreviation: CzPA), and 9-phenyl-3-[4-(10-phenyl-9-anthryl)phenyl]-9H-carbazole (abbreviation: PCzPA).

Examples of the anthracene derivative include 2-t-butyl-9,10-di(2-naphthyl)anthracene (abbreviation: t-BuDNA), 9,10-di(2-naphthyl)anthracene (abbreviation: DNA), and 9,10-diphenylanthracene (abbreviation: DPAnth).

High-molecular weight compounds, such as poly(N-vinylcarbazole) (abbreviation: PVK) and poly(4-vinyltriphenylamine) (abbreviation: PVTPA), can also be used.

However, compounds other than those as mentioned above can also be used so long as they are compounds high in the hole transporting ability rather than in the electron transporting ability.

The hole transporting layer may have a single-layer structure, or a multi-layer structure including two or more layers. For example, the hole transporting layer may have a two-layer structure including a first hole transporting layer (anode side) and a second hole transporting layer (cathode side). In one embodiment of the present invention, the hole transporting layer having the aforementioned single-layer structure is preferably adjacent to the light emitting layer, and in the multi-layer structure, the closest hole transporting layer to the light emitting layer, for example, the second hole transporting layer of the aforementioned two-layer structure, is preferably adjacent to the light emitting layer. In another embodiment of the present invention, a blocking layer as mentioned later or the like may be made to intervene between the hole transporting layer and the light emitting layer in the aforementioned single-layer structure, or between the closest hole transporting layer to the light emitting layer and the light emitting layer in the aforementioned multi-layer structure.

In the hole transporting layer of the two-layer structure, the compound (1) may be contained in either one of the first hole transporting layer and the second hole transporting layer or may be contained in both of them. However, the compound (1) contained in the first hole transporting layer differs from the compound (1) contained in the second hole transporting layer.

In one embodiment of the present invention, it is preferred that the compound (1) is contained only in the first hole transporting layer; in another embodiment, it is preferred that the compound (1) is contained only in the second hole transporting layer; and in a further embodiment, it is preferred that the compound (1) is contained in the first hole transporting layer and the second hole transporting layer.

In one embodiment of the present invention, the compound (1) contained in the first hole transporting layer and the second hole transporting layer is preferably a protium body (1) from the viewpoint of production cost.

The protium body (1) as referred to herein means the compound (1) in which all hydrogen atoms in the formula (1) are a protium atom.

In consequence, the present invention includes an organic EL device in which one or both of the first hole transporting layer and the second hole transporting layer contain the compound (1) substantially composed of only the protium compound (1). The wording "compound (1) substantially composed of only the protium compound (1)" means that a content proportion of the protium body (1) relative to the whole amount of the compounds represented by the formula (1) is 90 mol % or more, preferably 95 mol % or more, and more preferably 99 mol % or more (each including 100%).

Dopant Material of Light Emitting Layer

The light emitting layer is a layer containing a material having a high light emitting property (a dopant material), and various materials can be used. For example, a fluorescent emitting material or a phosphorescent emitting material can be used as the dopant material. The fluorescent emitting material is a compound that emits light from a singlet excited state, and the phosphorescent emitting material is a compound that emits from a light triplet excited state.

Examples of a blue-based fluorescent emitting material that can be used for the light emitting layer include a pyrene derivative, a styrylamine derivative, a chrysene derivative, a fluoranthene derivative, a fluorene derivative, a diamine derivative, and a triarylamine derivative. Specific examples thereof include N,N'-bis[4-(9H-carbazole-9-yl)phenyl]-N, N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenylamine (abbreviation: PCBAPA).

Examples of a green-based fluorescent emitting material that can be used for the light emitting layer include an aromatic amine derivative. Specific examples thereof include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthracene-2-amine (abbreviation: 2YGABPhA), and N,N,9-triphenylanthracene-9-amine (abbreviation: DPhAPhA).

Examples of a red-based fluorescent emitting material that can be used for the light emitting layer include a tetracene derivative and a diamine derivative. Specific examples thereof include N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

Examples of a blue-based phosphorescent emitting material that can be used for the light emitting layer include a metal complex, such as an iridium complex, an osmium complex, and a platinum complex. Specific examples thereof include bis[2-(4',6'-difluorophenyl)pyridinato-N,C2']iridium(III)tetrakis(1-pyrazolyl)borate (abbreviation: FIr6), bis[2-(4',6'-difluorophenyl)pyridinato-N,C2']iridium(III)picolinate (abbreviation: FIrpic), bis[2-(3',5'bistrifluoromethylphenyl)pyridinato-N,C2']iridium(III)picolinate (abbreviation: Ir(CF3ppy)2(pic)), and bis[2-(4',6'-difluorophenyl)pyridinato-N,C2']iridium(III)acetylacetonate (abbreviation: FIracac).

Examples of a green-based phosphorescent emitting material that can be used for the light emitting layer include an iridium complex. Examples thereof include tris(2-phenylpyridinato-N,C2')iridium(III) (abbreviation: Ir(ppy)3), bis(2-phenylpyridinato-N,C2')iridium(III)acetylacetonate (abbreviation: Ir(ppy)2(acac)), bis(1,2-diphenyl-1H-benzimidazolato)iridium(III)acetylacetonate (abbreviation: Ir(pbi)2(acac)), and bis(benzo[h]quinolinato)iridium(III) acetylacetonate (abbreviation: Ir(bzq)2(acac)).

Examples of a red-based phosphorescent emitting material that can be used for the light emitting layer include a metal complex, such as an iridium complex, a platinum complex, a terbium complex, and a europium complex. Specific examples thereof include organic metal complexes, such as bis[2-(2'-benzo[4,5-a]thienyl)pyridinato-N,C3'] iridium(III)acetylacetonate (abbreviation: Ir(btp)2(acac)), bis(1-phenylisoquinolinato-N,C2')iridium(III)acetylacetonate (abbreviation: Ir(piq)2(acac)), (acetylacetonate)bis[2,3-bis(4-fluorophenyl)quinoxalinato]iridium(III) (abbreviation: Ir(Fdpq)2(acac)), and 2,3,7,8,12,13,17,18-octaethyl-21H,23H-porphyrinplatinum(II) (abbreviation: PtOEP).

Rare earth metal complexes, such as tris(acetylacetonate) (monophenanthroline)terbium(III) (abbreviation: Tb(acac)3 (Phen)), tris(1,3-diphenyl-1,3-propandionato)(monophenanthroline)europium(III) (abbreviation: Eu(DBM)3 (Phen)), and tris[1-(2-thenoyl)-3,3,3-trifluoroacetonate] (monophenanthroline)europium(III) (abbreviation: Eu(TTA)3(Phen)), emit light from rare earth metal ions (electron transition between different multiplicities), and thus may be used as the phosphorescent emitting material.

Host Material of Light Emitting Layer

The light emitting layer may have a configuration in which the aforementioned dopant material is dispersed in another material (a host material). The compound (1) may be used as a host material or a cohost material of the fluorescent or phosphorescent light emitting layer, or other various compounds may be used. The host material is preferably a material that has a higher lowest unoccupied orbital level (LUMO level) and a lower highest occupied orbital level (HOMO level) than the dopant material.

In the organic EL device according to one embodiment of the present invention, the light emitting layer preferably contains at least any one of a compound represented by the following formula (X) and a compound represented by the following formula (Y).

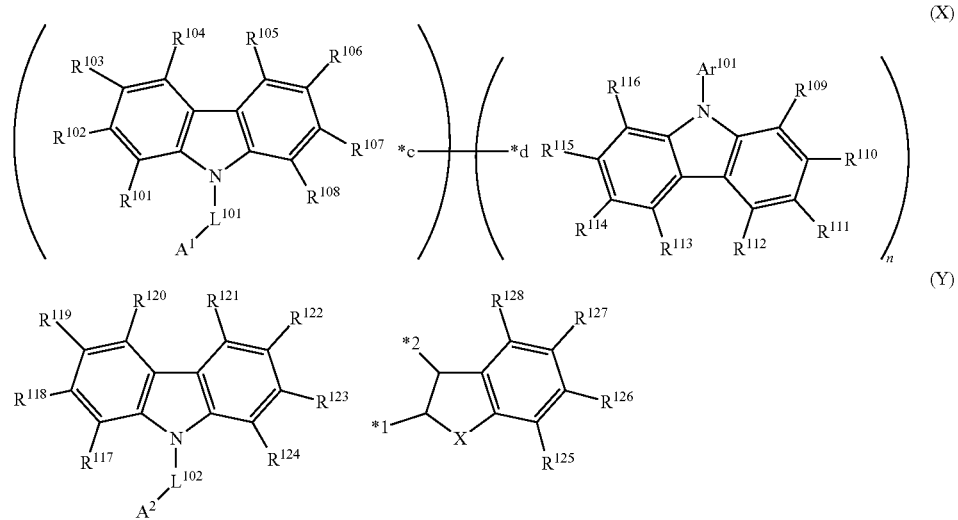

In the formula (X) and the formula (Y), $A^1$ and $A^2$ are each independently selected from the group consisting of a substituted or unsubstituted quinazoline ring, a substituted or unsubstituted triazine ring, a substituted or unsubstituted quinoxaline ring, a substituted or unsubstituted pyridine ring, a substituted or unsubstituted pyrimidine ring, a substituted or unsubstituted pyrazine ring, a substituted or unsubstituted pyridazine ring, and a substituted or unsubstituted fluoranthene ring.

Of these, a substituted or unsubstituted quinazoline ring, a substituted or unsubstituted triazine ring, a substituted or unsubstituted quinoxaline ring, and a substituted or unsubstituted pyrimidine ring are preferred, and a substituted or unsubstituted quinazoline ring and a substituted or unsubstituted quinoxaline ring are more preferred.

n is 0 or 1. When n is 0, it is meant that the carbazole structure in the right-side parenthesis of the formula (X) is not present.

$Ar^{101}$ is a substituted or unsubstituted aryl group having 6 to 30 ring carbon atoms.

In the substituted or unsubstituted aryl group having 6 to 30 ring carbon atoms, the aryl group having 6 to 30 ring carbon atoms is, for example, a phenyl group, a biphenylyl group, a terphenylyl group, a biphenylenyl group, a naphthyl group, an anthryl group, a benzoanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, or a triphenylenyl group, and preferably a phenyl group, a naphthyl group, or a phenanthryl group.

$L^{101}$ and $L^{102}$ are each independently selected from the group consisting of a single bond and a substituted or unsubstituted arylene group having 6 to 18 ring carbon atoms.

In the substituted or unsubstituted arylene group having 6 to 18 ring carbon atoms, the arylene group having 6 to 18 ring carbon atoms is, for example, a phenylene group, a biphenylene group, a terphenylene group, a biphenylenylene group, a naphthylene group, an anthrylene group, a benzoanthrylene group, a phenanthrylene group, a benzophenanthrylene group, a phenalenylene group, a pyrenylene group, a chrysenylene group, a fluorenylene group, a fluoranthenylene group, or a triphenylenylene group, and preferably a phenyl group or a naphthyl group.

In one embodiment of the present invention, $L^{101}$ and $L^{102}$ are preferably a single bond.

$R^{101}$ to $R^{127}$ are each independently a hydrogen atom or a substituent, and the substituent is selected from the group consisting of a halogen atom, a substituted or unsubstituted alkyl group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted aralkyl group having 7 to 36 carbon atoms, a substituted or unsubstituted alkoxy group having 1 to 30 carbon atoms, a substituted or unsubstituted aryloxy group having 6 to 30 ring carbon atoms, a mono-, di-, or tri-substituted silyl group having a substituent selected from a substituted or unsubstituted alkyl group having 1 to 30 carbon atoms and a substituted or unsubstituted aryl group having 6 to 30 ring carbon atoms, and a substituted or unsubstituted heteroaryl group having 5 to 30 ring atoms.

Specific examples and preferred groups of the substituent are the same as those for $R^{11}$ to $R^{18}$ and $R^{20}$ to $R^{29}$.

X represents $NR^{201}$, O, S, or $CR^{202}R^{203}$; $R^{201}$ is a substituted or unsubstituted phenyl group; $R^{202}$ and $R^{203}$ are each independently a hydrogen atom or a substituent; and the substituent is selected from the group consisting of a substituted or unsubstituted alkyl group having 1 to 30 carbon atoms and a substituted or unsubstituted aryl group having 6 to 30 ring carbon atoms.

In the substituted or unsubstituted alkyl group having 1 to 30 carbon atoms, the alkyl group having 1 to 30 carbon atoms is, for example, a methyl group, an ethyl group, an n-propyl group, an isopropyl group, an n-butyl group, an isobutyl group, an s-butyl group, a t-butyl group, a pentyl group, a hexyl group, a heptyl group, an octyl group, a nonyl group, a decyl group, an undecyl group, or a dodecyl group; preferably a methyl group, an ethyl group, an n-propyl group, an isopropyl group, an n-butyl group, an isobutyl group, an s-butyl group, a t-butyl group, or a pentyl group; more preferably a methyl group, an ethyl group, an n-propyl group, an isopropyl group, an n-butyl group, an isobutyl group, an s-butyl group, or a t-butyl group; and still more preferably a methyl group.

The substituted or unsubstituted alkyl group having 1 to 30 carbon atoms includes isomer groups if present.

In the substituted or unsubstituted aryl group having 6 to 30 ring carbon atoms, the aryl group having 6 to 30 ring carbon atoms is, for example, a phenyl group, a biphenylyl group, a terphenylyl group, a biphenylenyl group, a naphthyl group, an anthryl group, a benzoanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, or a triphenylenyl group; preferably a phenyl group, a biphenylyl group, a terphenylyl group, or a naphthyl group; and more preferably a phenyl group.

$R^{202}$ and $R^{203}$ may be mutually bonded to form a substituted or unsubstituted ring structure.

In the formula (X), one selected from $R^{105}$ to $R^{108}$, preferably $R^{106}$ is a single bond bonding to *c; and one selected from $R^{113}$ to $R^{116}$, preferably $R^{114}$ is a single bond bonding to *d.

Adjacent two selected from $R^{101}$ to $R^{108}$ other than the single bond bonding to *c, and $R^{109}$ to $R^{116}$ other than the single bond bonding to *d may be mutually bonded to form a substituted or unsubstituted ring structure.

In the formula (Y), in the adjacent pairs selected from $R^{121}$ to $R^{124}$, one of them is a single bond bonding to *1, and the other is a single bond bonding to *2.

Adjacent two selected from $R^{117}$ to $R^{128}$ other than the single bond bonding to *1 and the single bond bonding to *2 may be mutually bonded to form a substituted or unsubstituted ring structure.

Specific examples of the compound (A) and the compound (Y) and examples of other usable hosts are hereunder exemplified, but are not limited thereto.

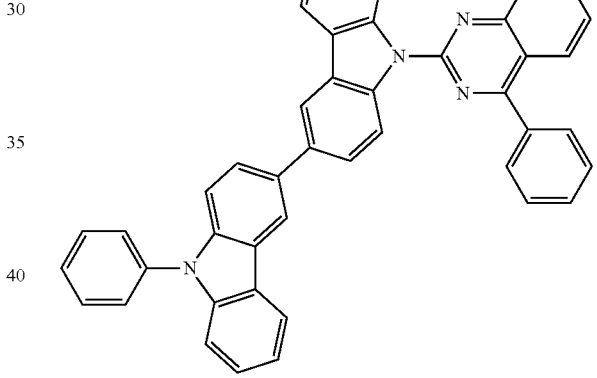

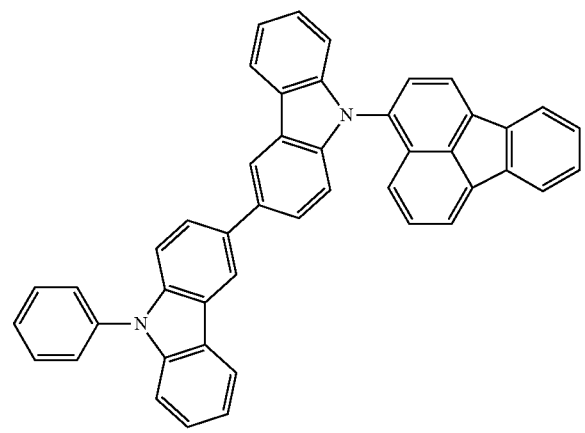

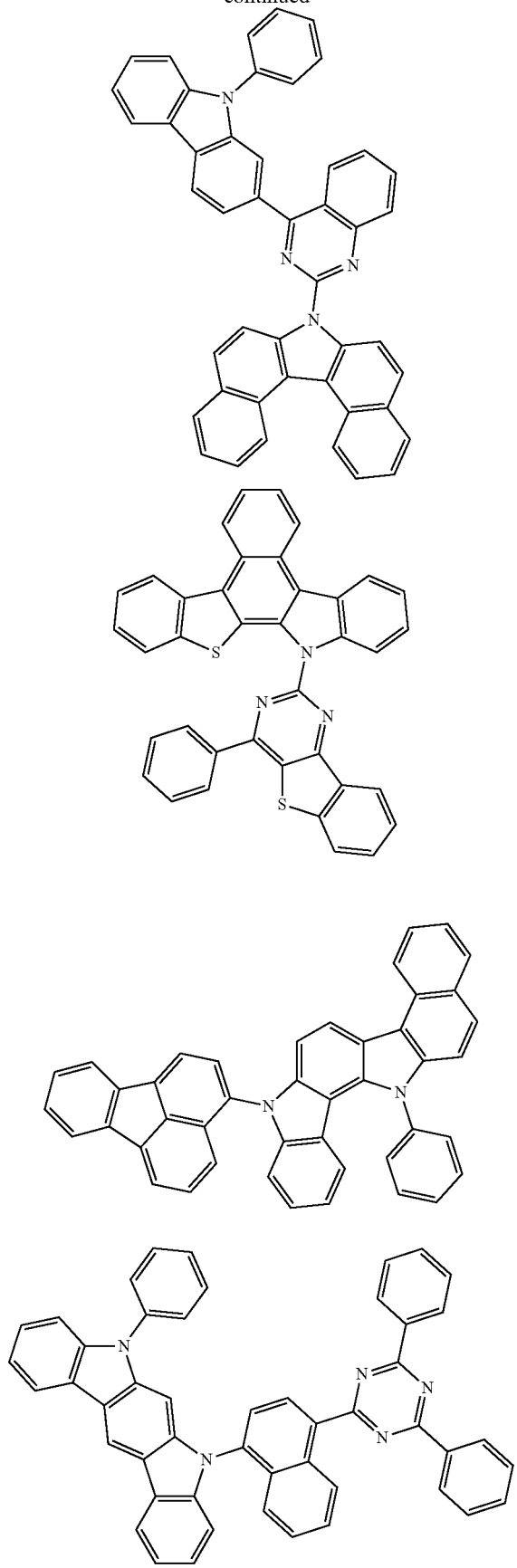
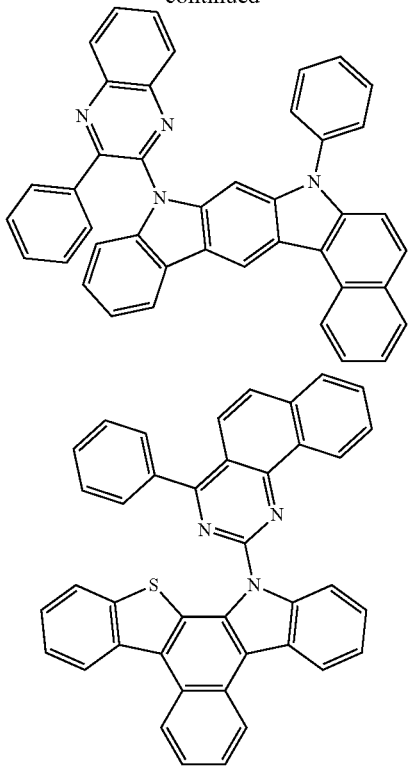

Examples of the host material other than the compound (1), the compound (X), and the compound (Y), which is used, include:

(1) a metal complex, such as an aluminum complex, a beryllium complex, and a zinc complex,
(2) a heterocyclic compound, such as an oxadiazole derivative, a benzimidazole derivative, and a phenanthroline derivative,
(3) a fused aromatic compound, such as a carbazole derivative, an anthracene derivative, a phenanthrene derivative, a pyrene derivative, and a chrysene derivative, or
(4) an aromatic amine compound, such as a triarylamine derivative and a fused polycyclic aromatic amine derivative.

For example,
metal complexes, such as tris(8-quinolinolato)aluminum (III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ);

heterocyclic compounds, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), and bathophenanthroline (abbreviation: BPhen), bathocuproine (abbreviation: BCP);

fused aromatic compounds, such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl(abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), 9,10-diphenylanthracene (abbreviation: DPAnth), and 6,12-dimethoxy-5,11-diphenylchrysene; and aromatic amine compounds, such as N,N-diphenyl-9-[4-(10-phenyl-9-anthryl)phenyl]-9H-carbazole-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl]phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluoren-2-yl)-N-phenylamino]biphenyl (abbreviation: DFLDPBi), and 4,4'-bis[N-(spiro-9,9'-bifluoren-2-yl)-N-phenylamino]biphenyl (abbreviation: BSPB) can be used. A plurality of host materials may be used.

In particular, in the case of a blue fluorescent device, it is preferred to use the following anthracene compounds as the host material.

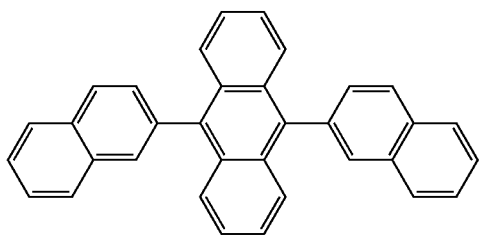
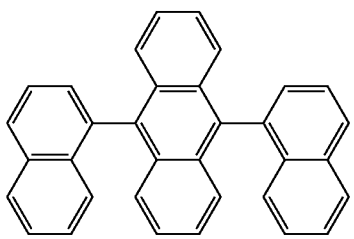
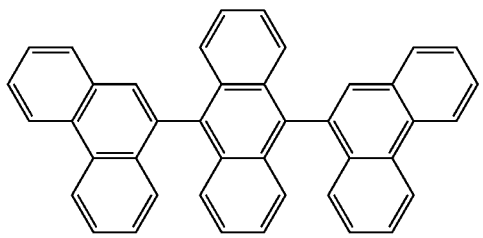
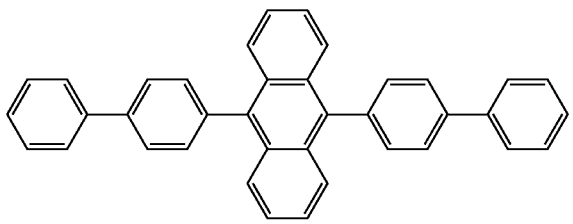
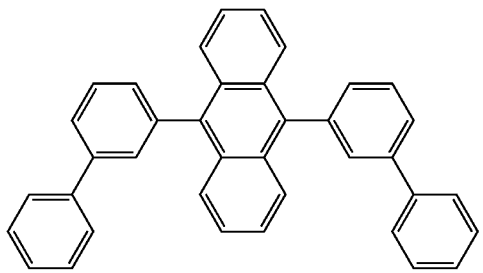
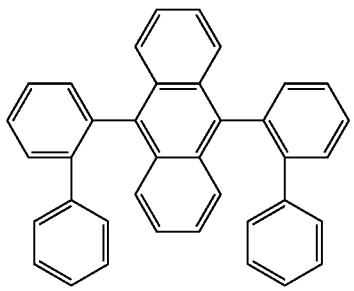
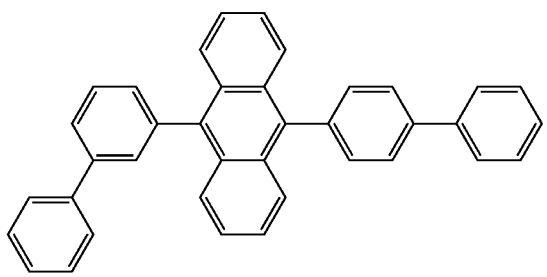

-continued
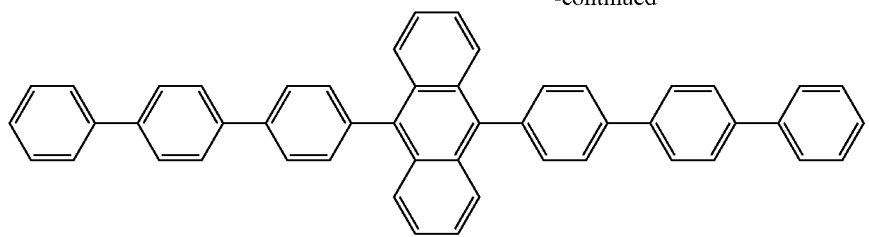
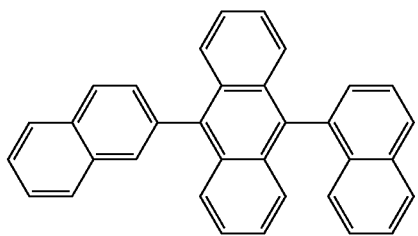 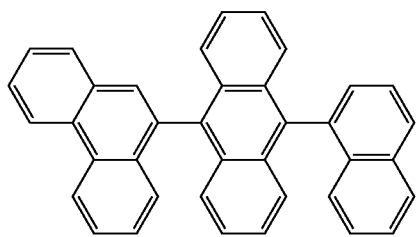
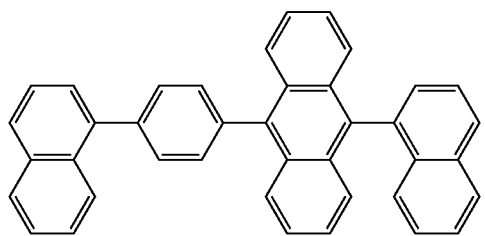 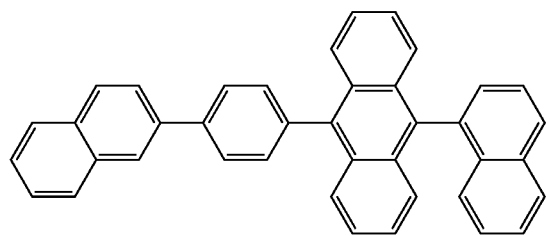
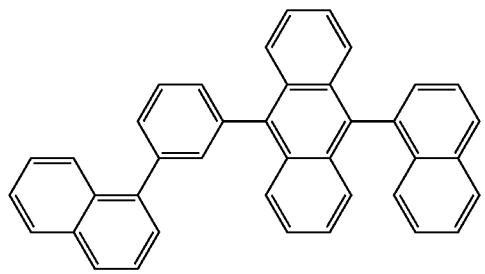 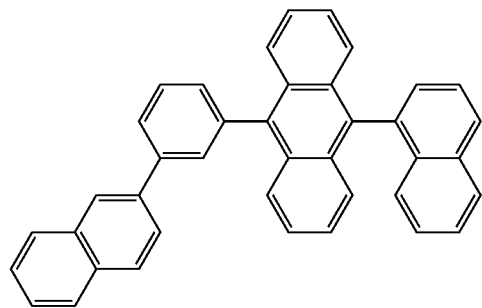
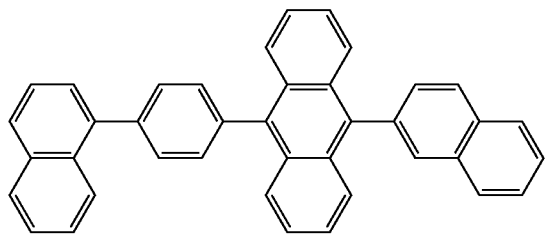 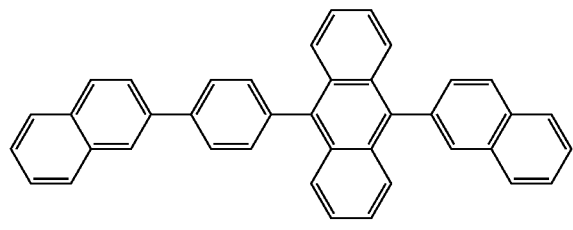
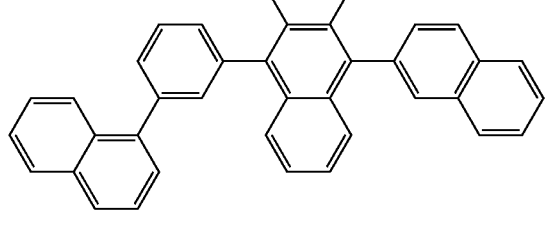 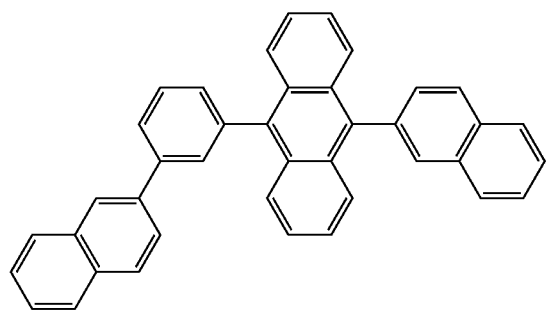

-continued

117
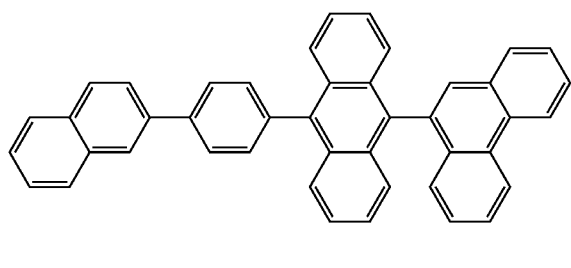
118
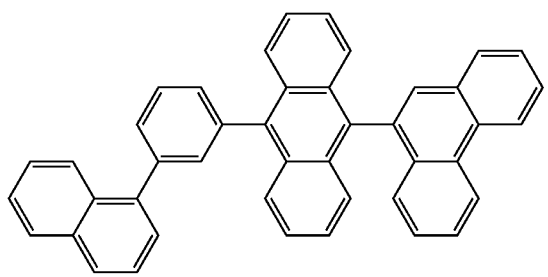
-continued
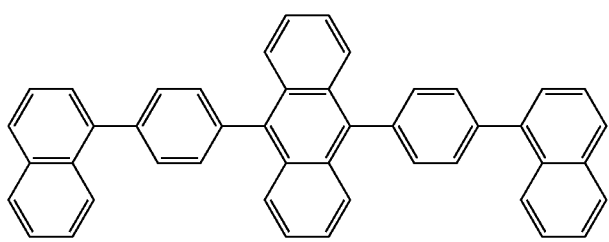
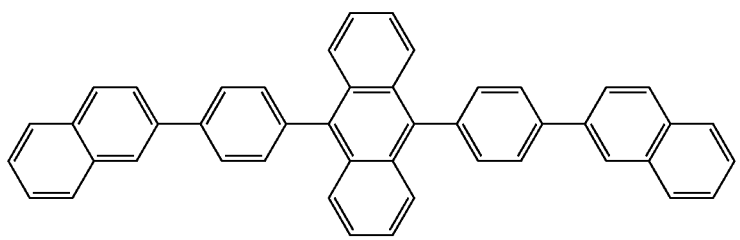
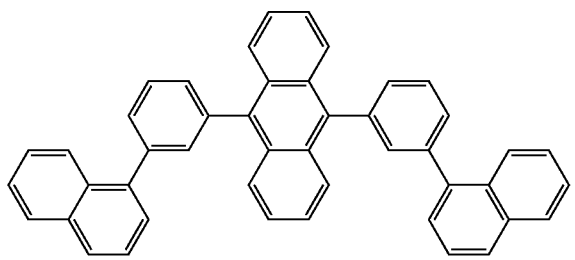
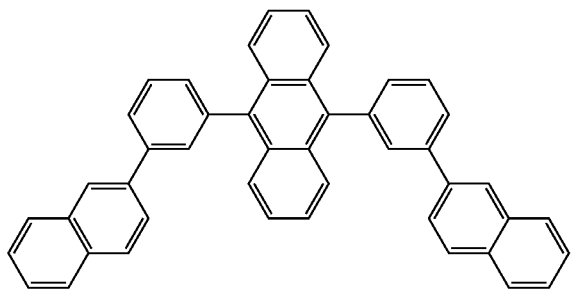
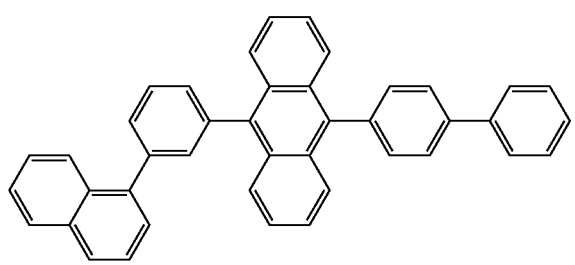
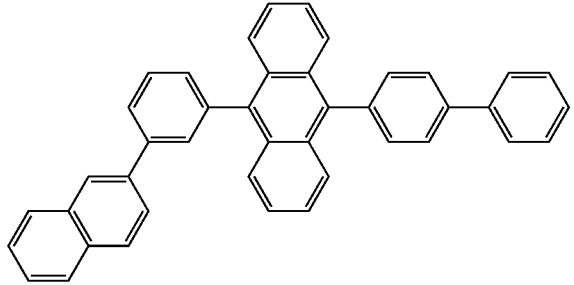
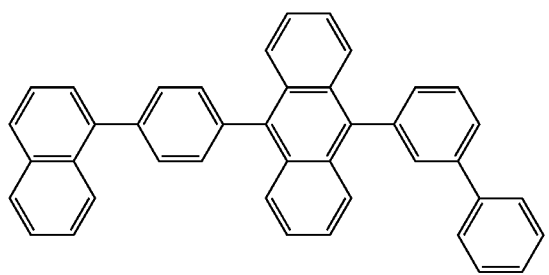
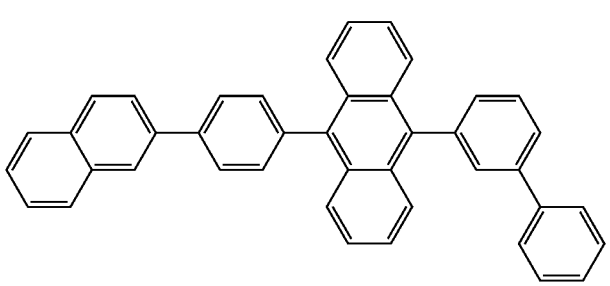

-continued
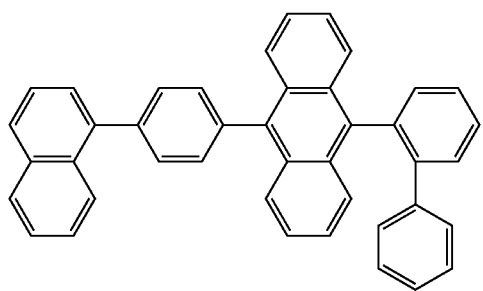
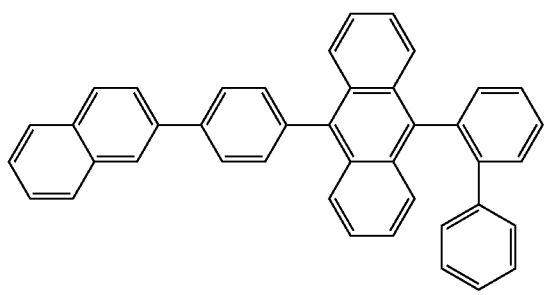
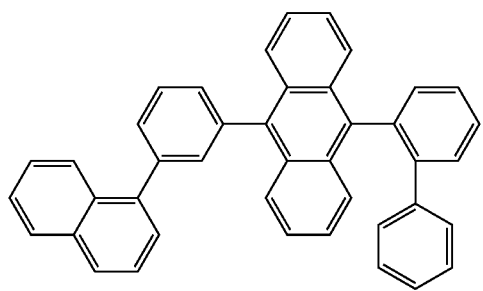
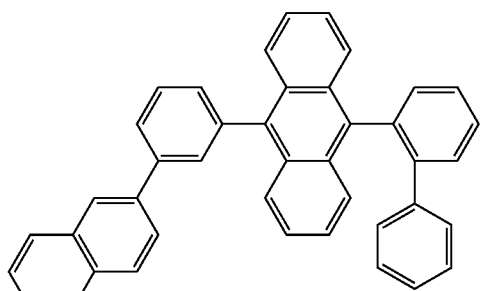
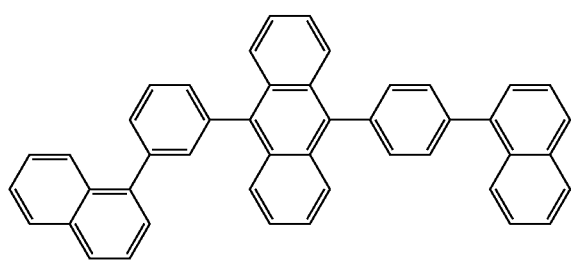
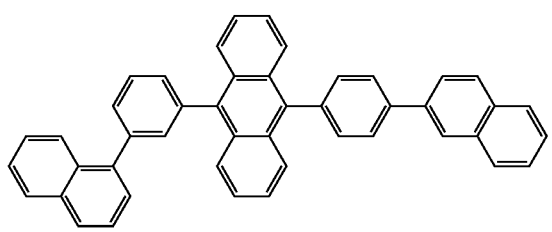
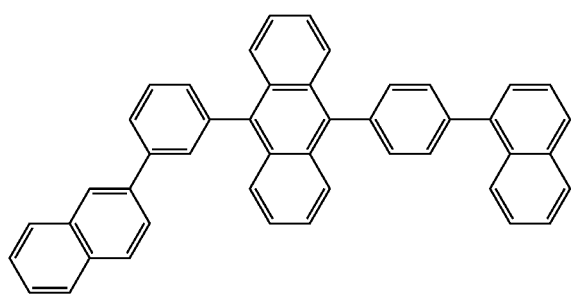
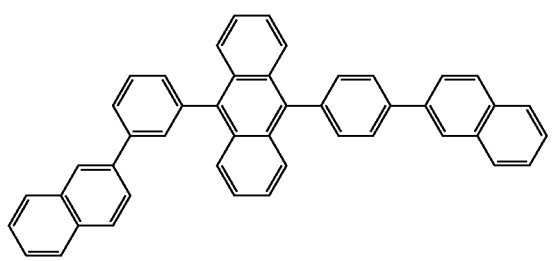
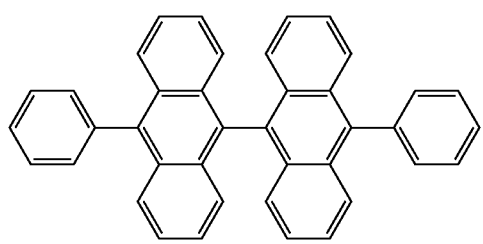
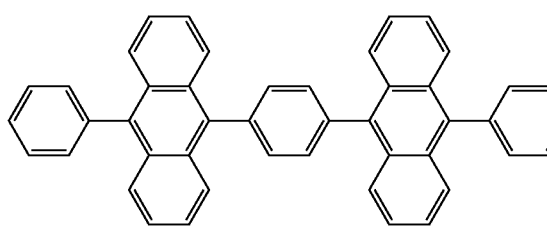
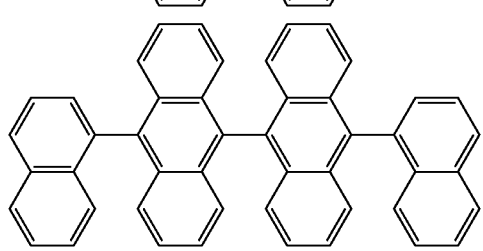
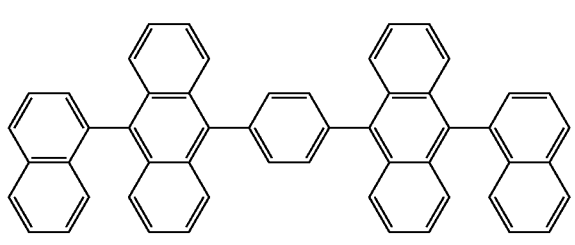

121
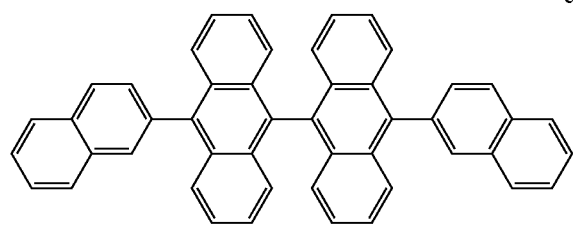
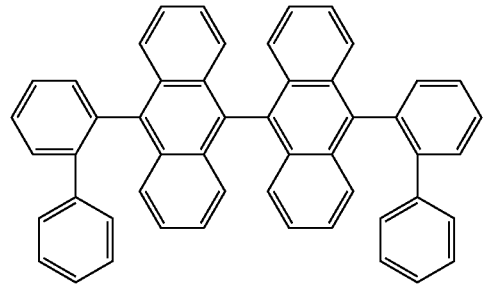
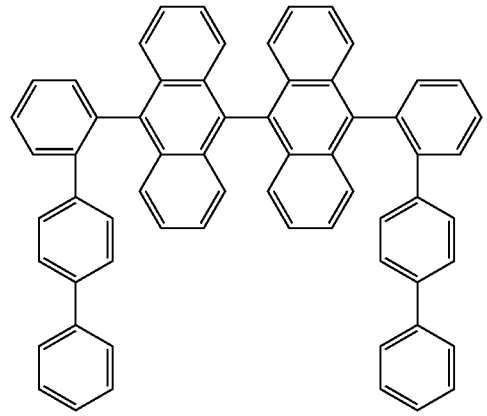
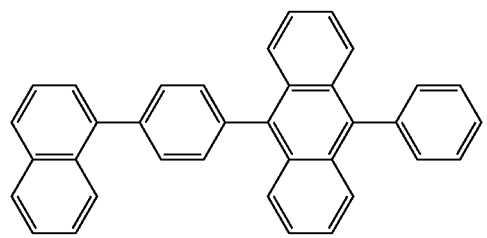
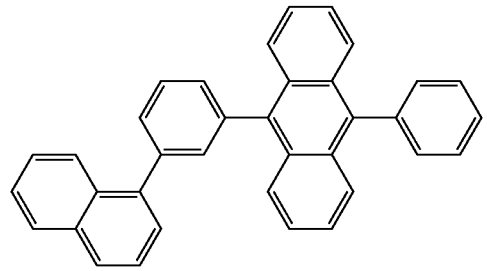
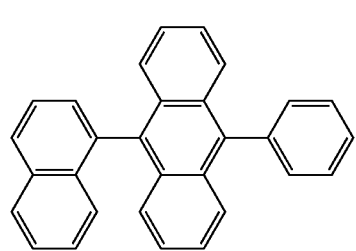
122
-continued
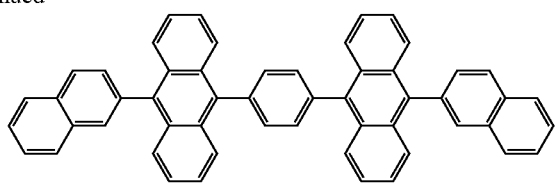
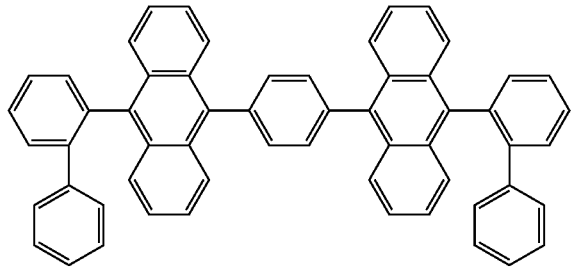
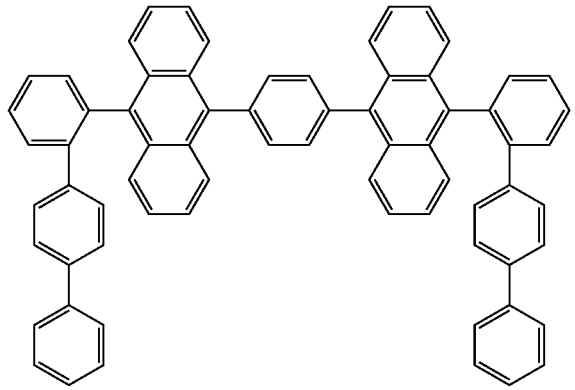
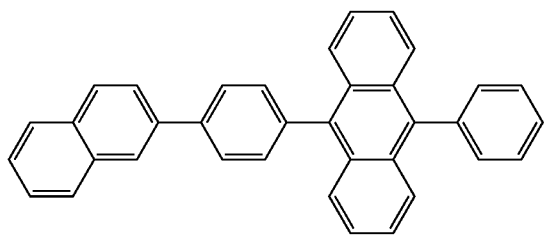
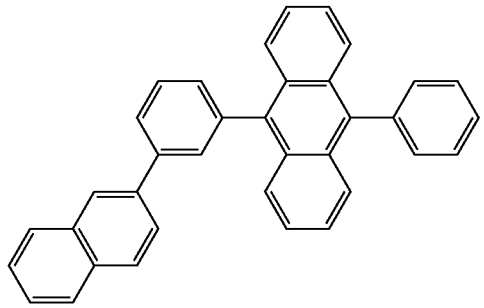
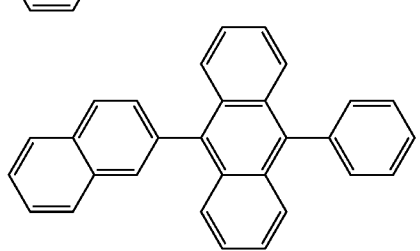

123
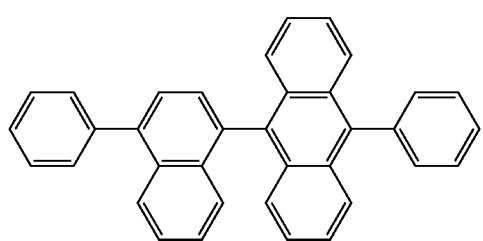
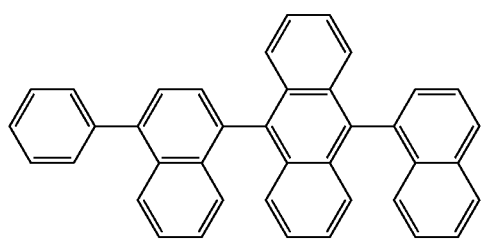
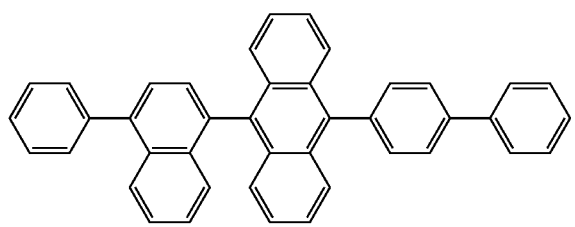
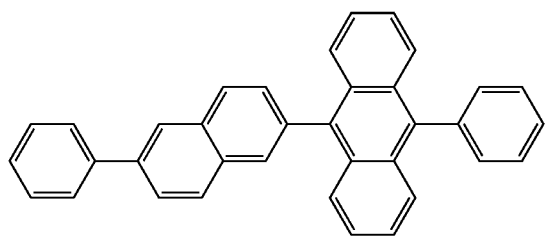
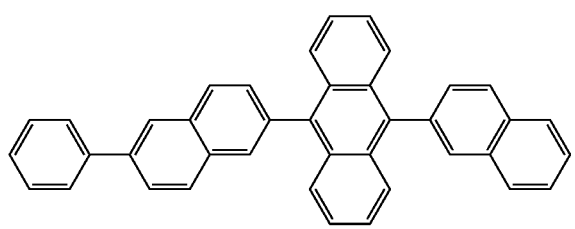
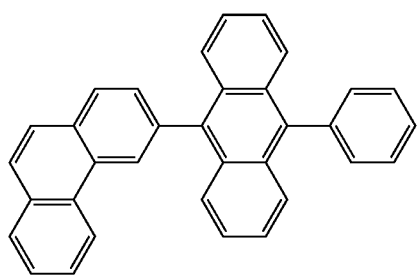
124
-continued
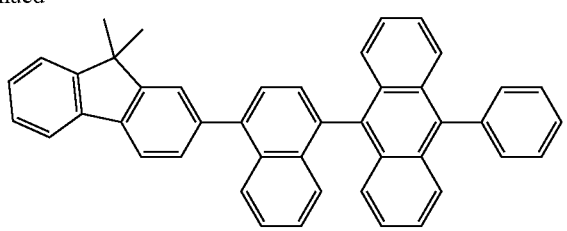
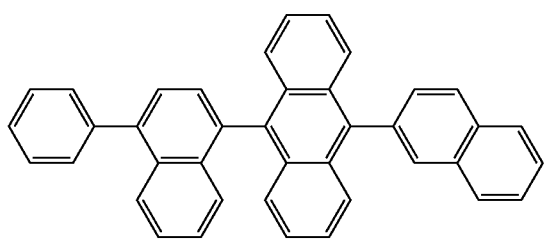
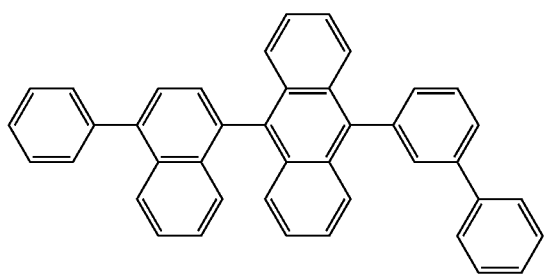
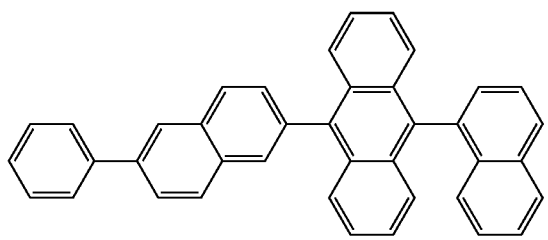
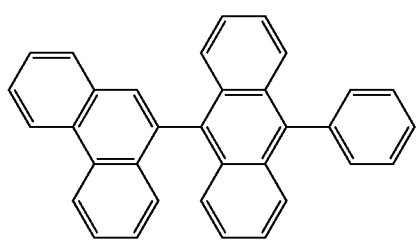
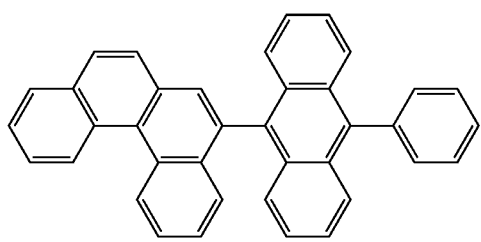

125
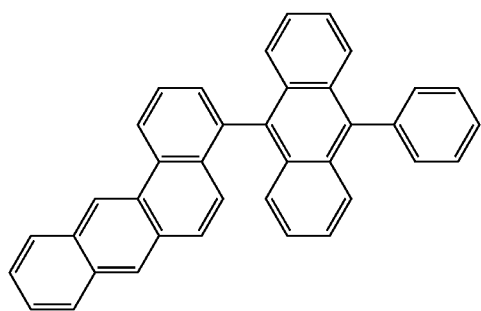
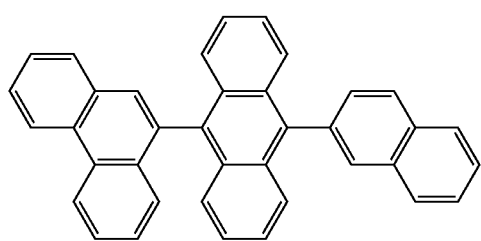
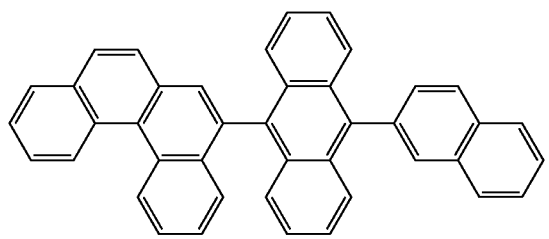
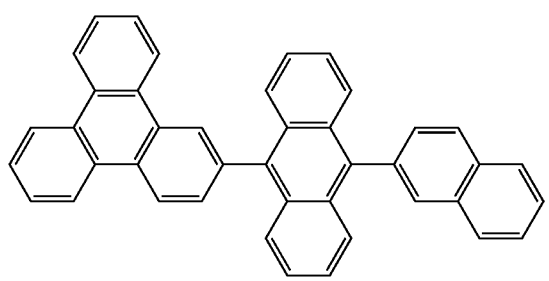
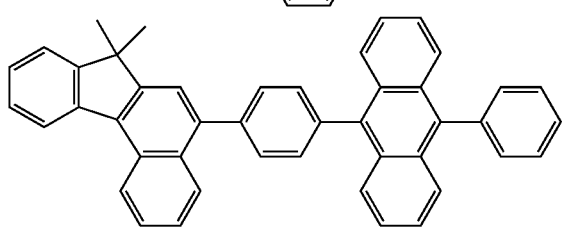
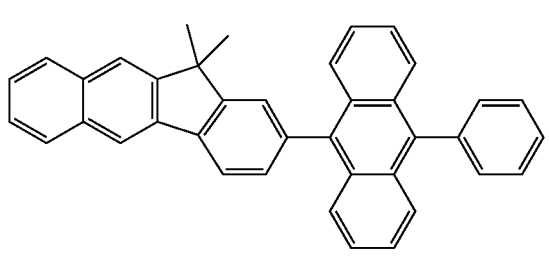
126
-continued
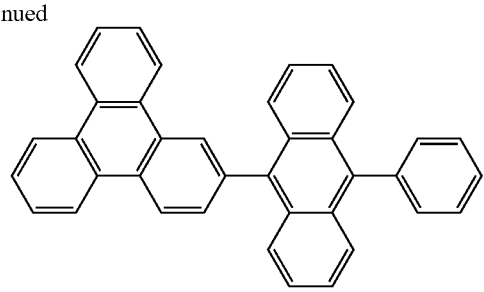
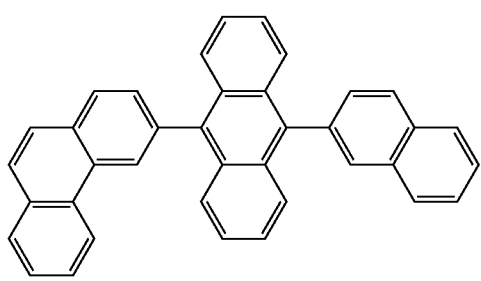
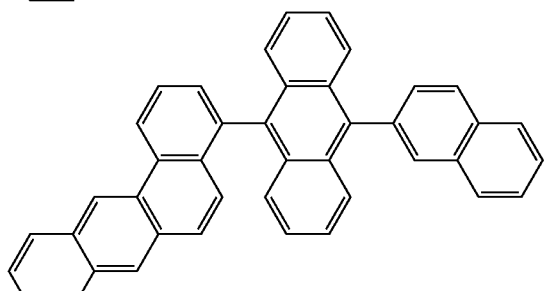
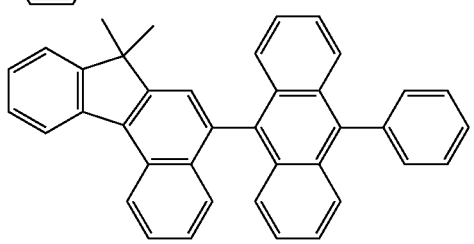
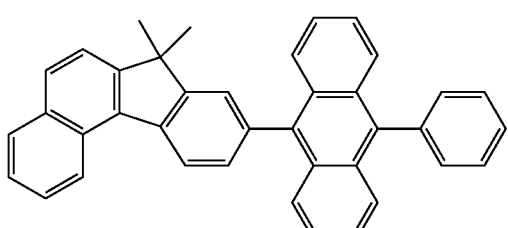
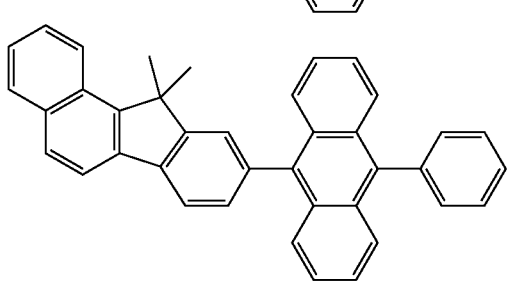

127
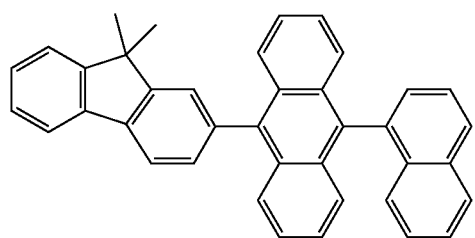
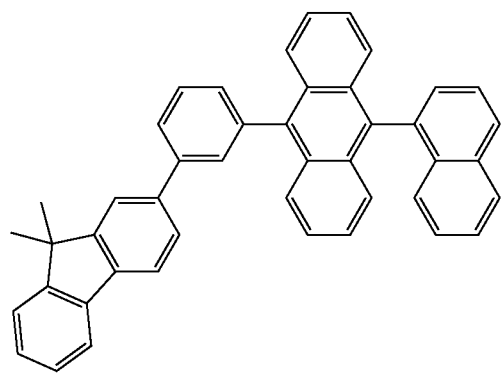
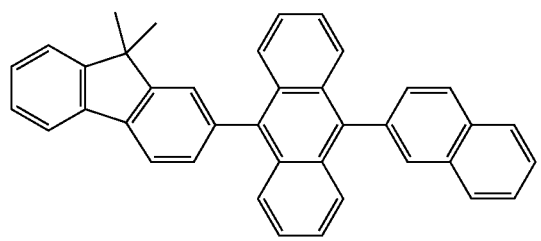
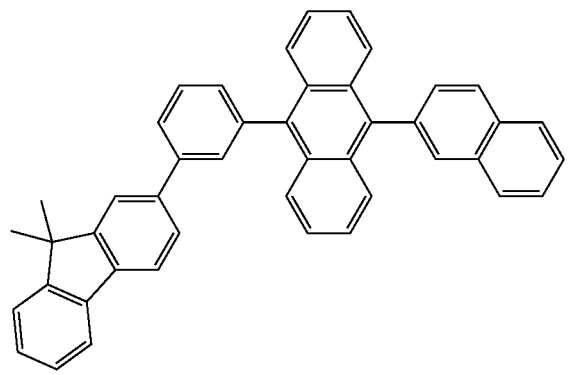
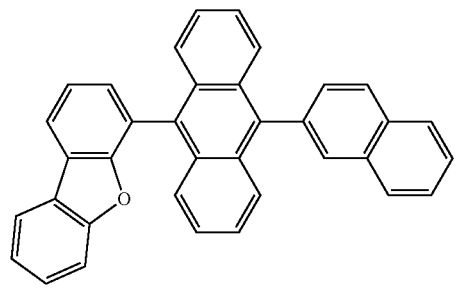
128
-continued
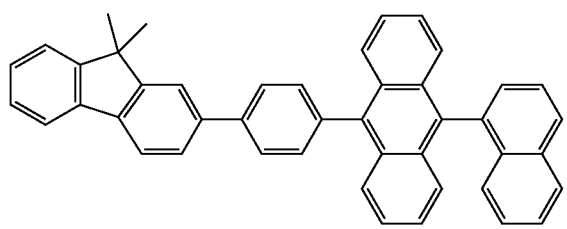
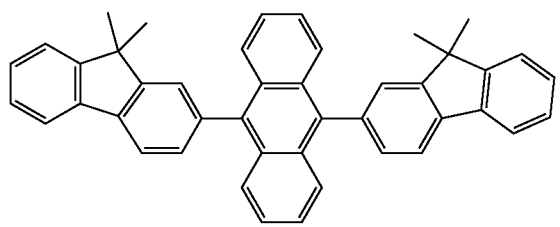
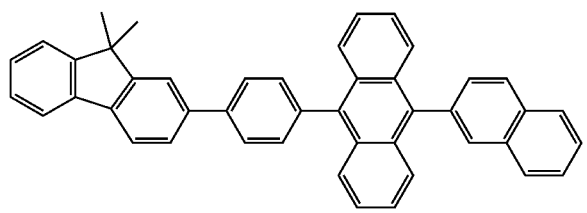
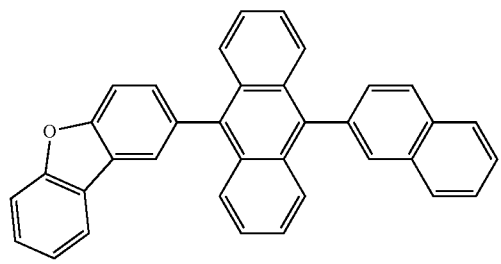
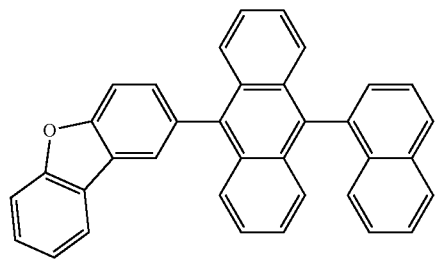

129 130
-continued
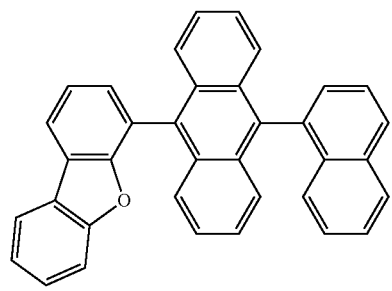 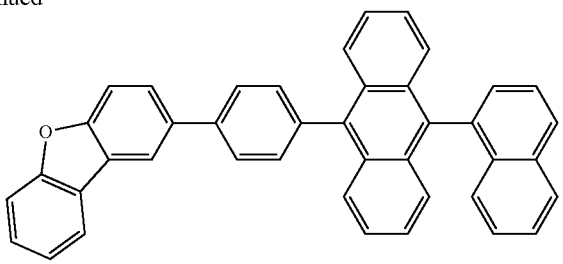
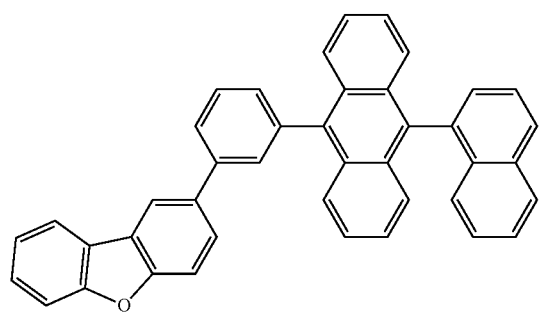 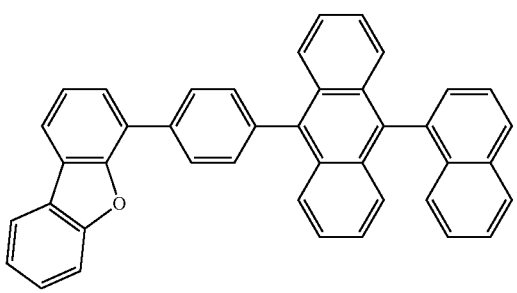
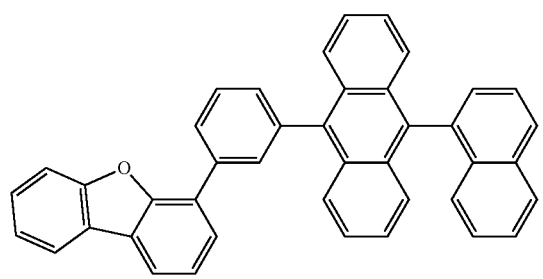 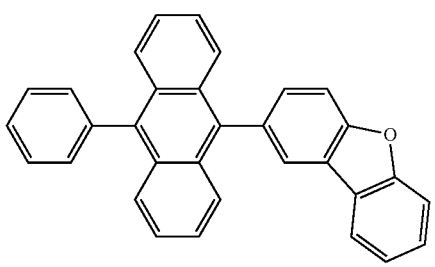
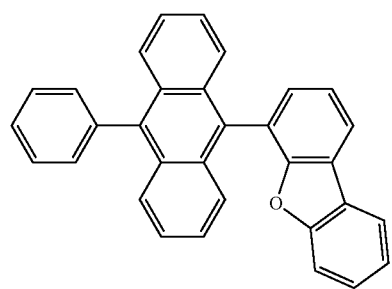 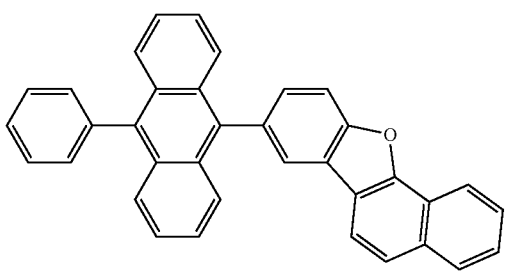
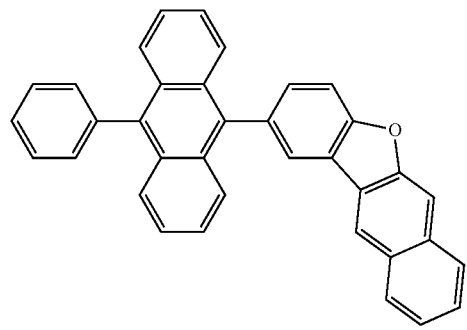 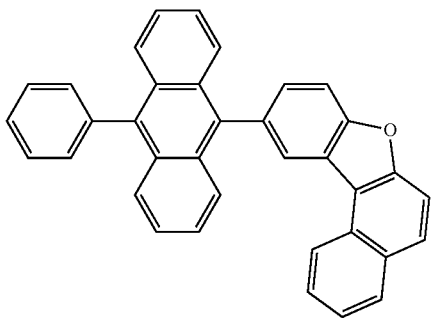

131
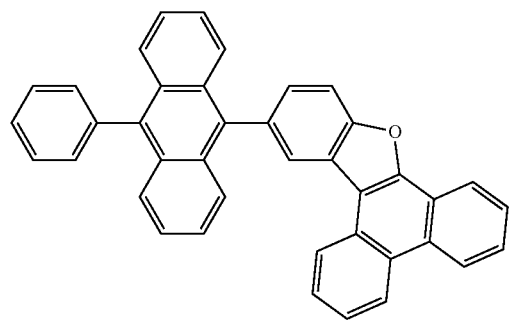
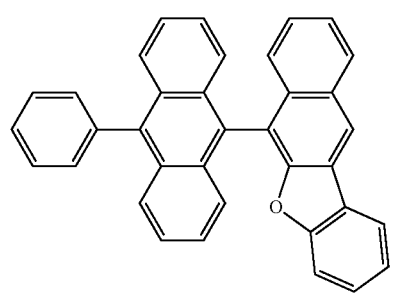
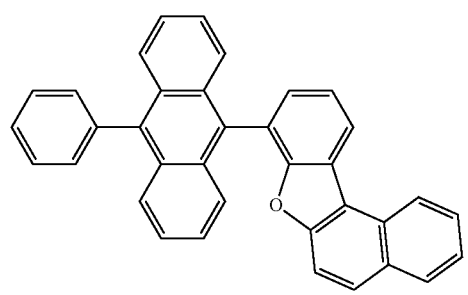
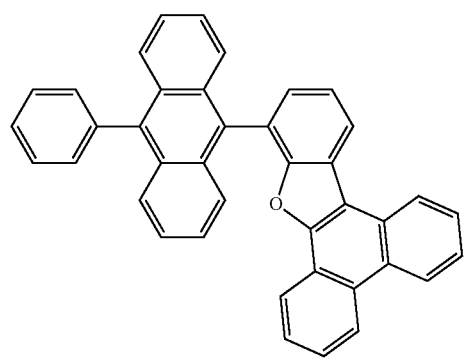
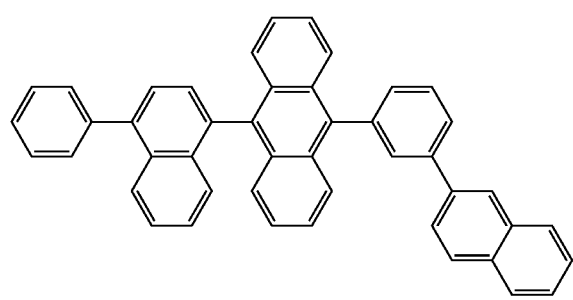
132
-continued
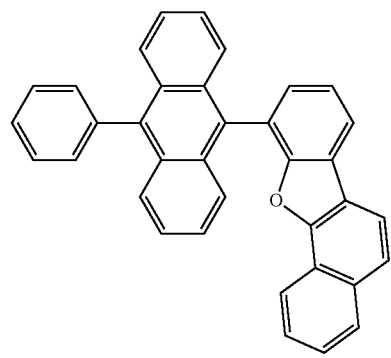
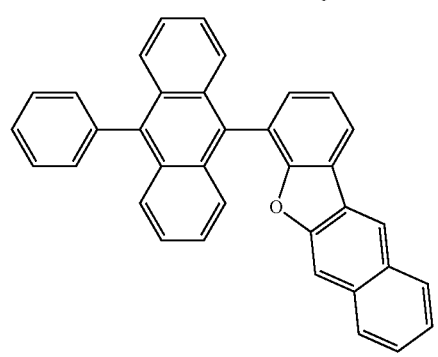
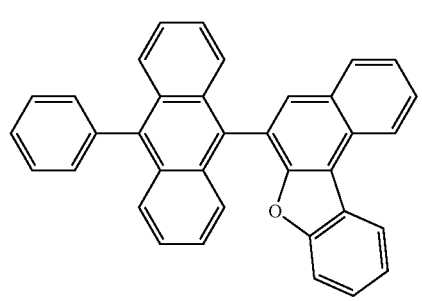
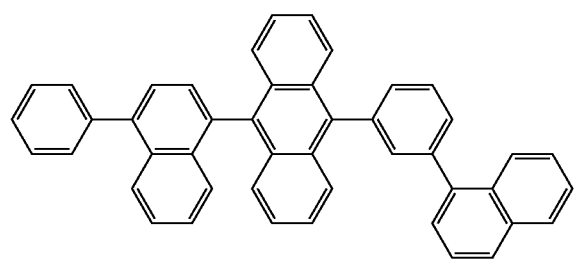
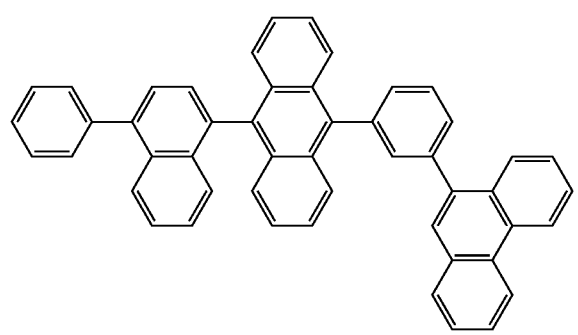

-continued
| 133 | 134 |
|---|---|
| 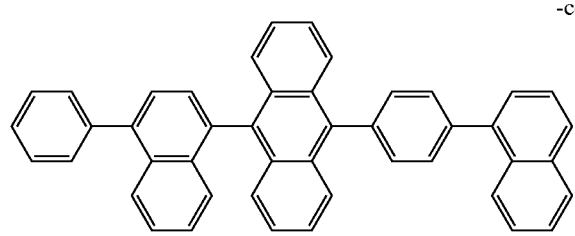 | 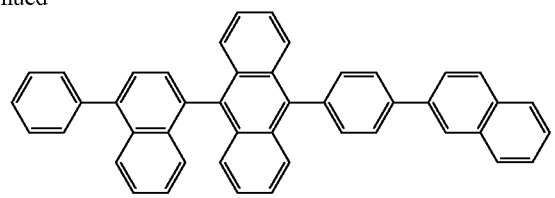 |
| 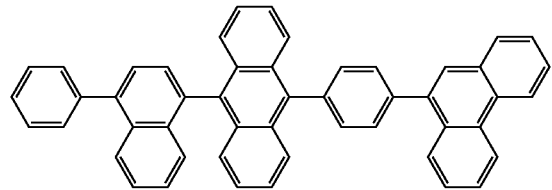 | 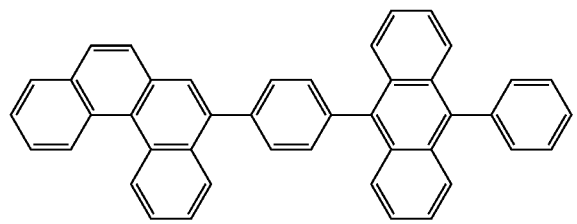 |
| 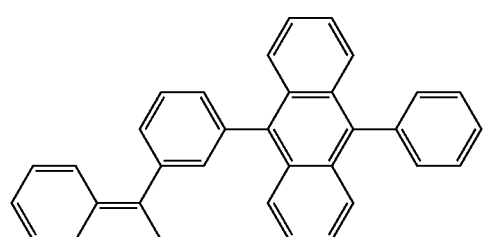 | 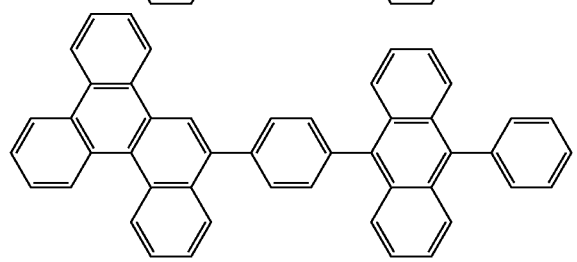 |
| 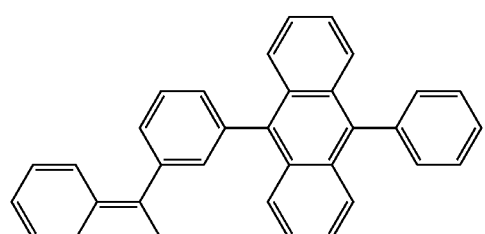 | 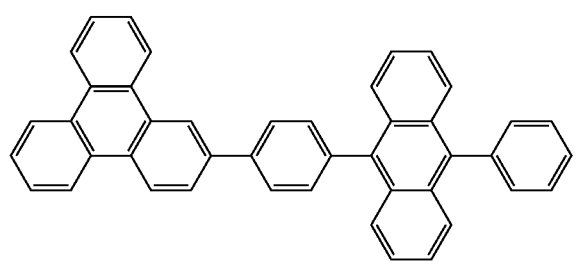 |
| 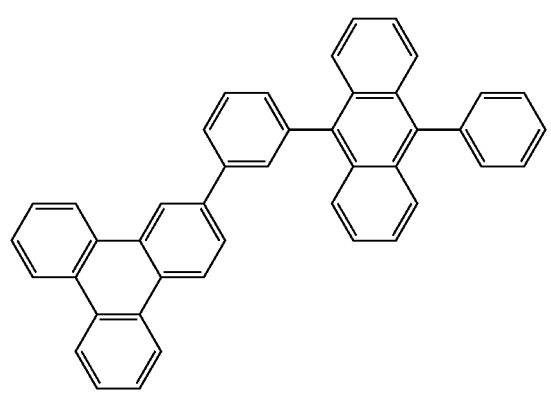 | |

Electron Transporting Layer

The electron transporting layer is a layer containing a material having a high electron transporting ability (an electron transporting material). Examples of the material which can be used for the electron transporting layer include:

(1) a metal complex, such as an aluminum complex, a beryllium complex, and a zinc complex;
(2) a heteroaromatic compound, such as an imidazole derivative, a benzimidazole derivative, an azine derivative, a carbazole derivative, and a phenanthroline derivative; and
(3) a high-molecular weight compound.

Examples of the metal complex include tris(8-quinolinolato)aluminum(III) (abbreviation: Alq), tris(4-methyl-8-quinolinolato)aluminum (abbreviation: Almq3), bis(10-hydroxybenzo[h]quinolinato)beryllium (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ).

Examples of the heteroaromatic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzxazol-2-yl)stilbene (abbreviation: BzOs).

Examples of the high-molecular weight compound include poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy).

The materials are materials having an electron mobility of $10^{-6}$ cm$^2$/Vs or more. Materials other than those as mentioned above may also be used in the electron transporting layer so long as they are materials high in the electron transporting ability rather than in the hole transporting ability.

The electron transporting layer may be a single-layer, or a multi-layer including two or more layers. For example, the electron transporting layer may be a layer including a first electron transporting layer (anode side) and a second electron transporting layer (cathode side). Each of the two or more electron transporting layers is formed of the aforementioned electron transporting material.

Electron Injecting Layer

The electron injecting layer is a layer containing a material having a high electron injection ability. In the electron injecting layer, alkali metals, alkaline earth metals, or compounds thereof, such as lithium (Li), cesium (Cs), calcium (Ca), lithium fluoride (LiF), cesium fluoride (CsF), calcium fluoride (CaF$_2$), and lithium oxide (LiO$_x$), can be used. Besides, a material having an electron transporting ability, in which an alkali metal, an alkaline earth metal, or a compound thereof is contained, specifically Alq in which magnesium (Mg) is contained may be used. In this case, electron injection from the cathode can be more efficiently performed.

Otherwise, in the electron injecting layer, a composite material obtained by mixing an organic compound with an electron donor may be used. Such a composite material is excellent in the electron injection ability and the electron transporting ability because the organic compound receives electrons from the electron donor. In this case, the organic compound is preferably a material excellent in transporting received electrons, and specifically, examples thereof include a material constituting the aforementioned electron transporting layer (a metal complex, a heteroaromatic compound, etc.). As the electron donor, a material having an electron donation property for the organic compound may be used. Specifically, alkali metals, alkaline earth metals, and rare earth metals are preferred, and examples thereof include lithium, cesium, magnesium, calcium, erbium, and ytterbium. In addition, an alkali metal oxide or an alkaline earth metal oxide is preferred, and examples thereof include lithium oxide, calcium oxide, and barium oxide. In addition, a Lewis base, such as magnesium oxide, can also be used. In addition, an organic compound, such as tetrathiafulvalene (abbreviation: TTF), can also be used.

Cathode

It is preferred that a metal, an alloy, an electrically conductive compound, or a mixture thereof which has a low work function (specifically 3.8 eV or less) is used for the cathode. Specific examples of such a cathode material include elements belonging to group 1 or 2 of the periodic table of the elements, that is, alkali metals, such as lithium (Li) and cesium (Cs), alkaline earth metals, such as magnesium (Mg), calcium (Ca), and strontium (Sr), and alloys containing these (for example, MgAg, and AlLi), and rare earth metals, such as europium (Eu), and ytterbium (Yb) and alloys containing these.

When the cathode is formed by using the alkali metals, the alkaline earth metals, and the alloys containing these, a vacuum vapor deposition method or a sputtering method can be adopted. In addition, when a silver paste or the like is used, a coating method, an inkjet method, etc. can be adopted.

By providing the electron injecting layer, the cathode can be formed using various conductive materials, such as Al, Ag, ITO, graphene, and indium oxide-tin oxide containing silicon or silicon oxide regardless of the magnitude of a work function. Such a conductive material can be deposited by using a sputtering method, an inkjet method, a spin coating method, or the like.

Insulating Layer

The organic EL device applies an electric field to an ultrathin film, and thus, pixel defects are likely to occur due to leaks or short-circuiting. In order to prevent this, an insulating layer formed of an insulating thin film layer may be inserted between a pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or a laminate of these may also be used.

Space Layer

The space layer is, for example, a layer provided between a fluorescent light emitting layer and a phosphorescent light emitting layer for the purpose of preventing excitons generated in the phosphorescent light emitting layer from diffusing into the fluorescent light emitting layer, or adjusting a carrier balance, in the case where the fluorescent light emitting layers and the phosphorescent light emitting layers are stacked. The space layer can also be provided among the plurality of phosphorescent light emitting layers.

Since the space layer is provided between the light emitting layers, a material having both an electron transporting ability and a hole transporting ability is preferred. Also, one having a triplet energy of 2.6 eV or more is preferred in order to prevent triplet energy diffusion in the adjacent phosphorescent light emitting layer. Examples of the material used for the space layer include the same as those used for the hole transporting layer as described above.

Blocking Layer

The blocking layer such as the electron blocking layer, the hole blocking layer, or the exciton blocking layer may be provided adjacent to the light emitting layer. The electron blocking layer is a layer that prevents electrons from leaking from the light emitting layer to the hole transporting layer, and the hole blocking layer is a layer that prevents holes from leaking from the light emitting layer to the electron transporting layer. The exciton blocking layer has a function of preventing excitons generated in the light emitting layer from diffusing into the surrounding layers, and trapping the excitons within the light emitting layer.

Each layer of the organic EL device may be formed by a conventionally known vapor deposition method, a coating method, etc. For example, formation can be performed by a known method using a vapor deposition method such as a vacuum vapor deposition method, or a molecular beam vapor deposition method (MBE method), or a coating method using a solution of a compound for forming a layer, such as a dipping method, a spin-coating method, a casting method, a bar-coating method, and a roll-coating method.

The film thickness of each layer is not particularly limited, but is typically 5 nm to 10 μm, and more preferably 10 nm to 0.2 μm because in general, when the film thickness is too small, defects such as pinholes are likely to occur, and conversely, when the film thickness is too large, a high driving voltage is required and the efficiency decreases.

The organic EL device can be used for electronic devices, such as display components of organic EL panel modules, etc., display devices of televisions, mobile phones, personal computers, etc., and light emitting devices of lightings and vehicular lamps.

EXAMPLES

The present invention is hereunder described in more detail by reference to Examples, but it should be construed that the present invention is not limited to the following Examples.

Compounds Used for the Second Hole Transporting Layer in the Following Examples 1-1 to 1-4

Compound 1

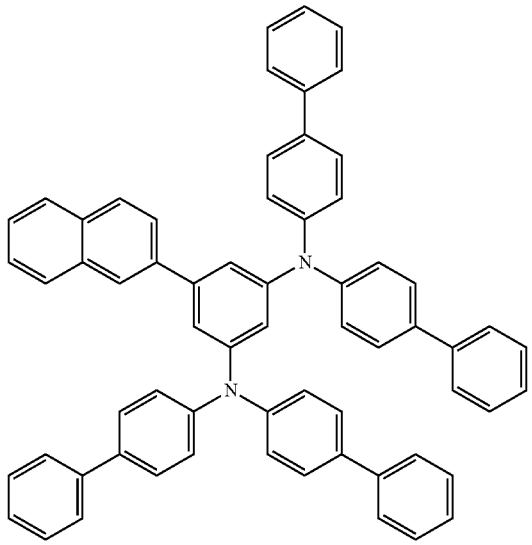

Compound 2

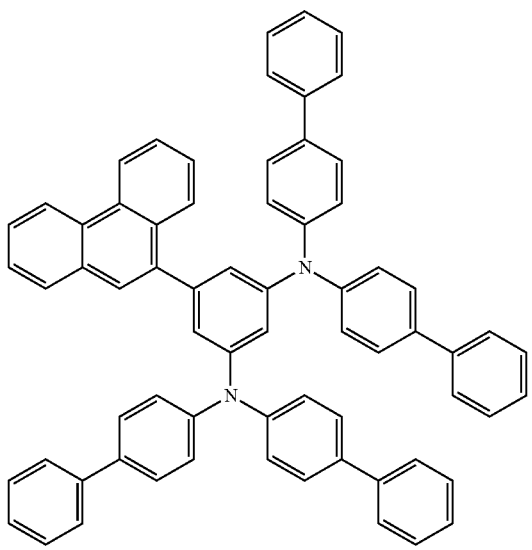

Compound 3

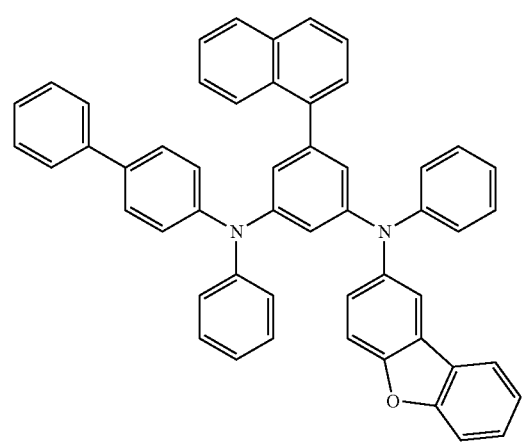

Compound 5
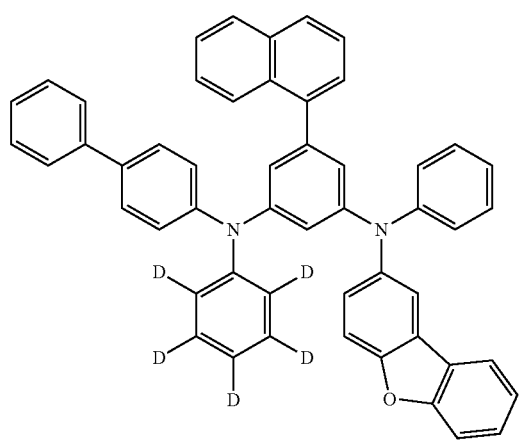
Comparative Compound Used for the Second Hole Transporting Layer of the Following Comparative Example 1-1
Comparative Compound 1
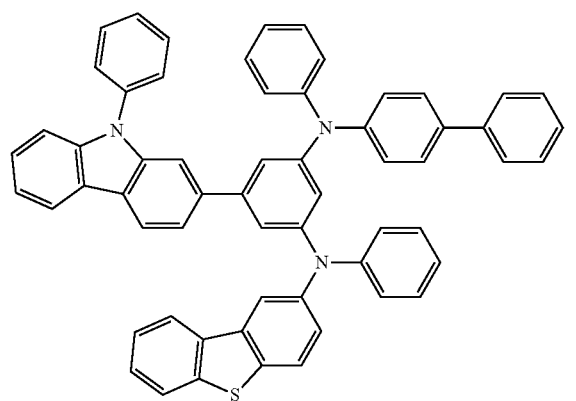
Other Compounds Used for Production of the Organic EL Devices of the Following Examples 1-1 to 1-4 and the Following Comparative Example 1-1
HA
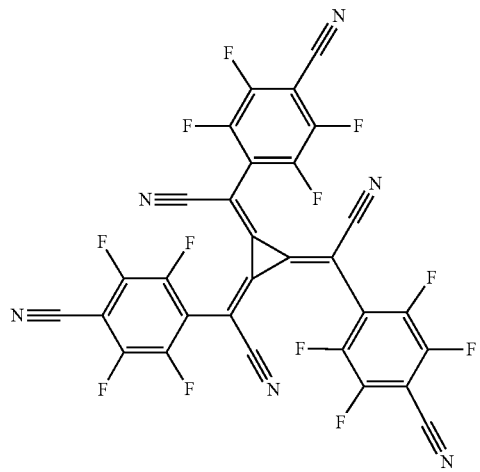
PH-1
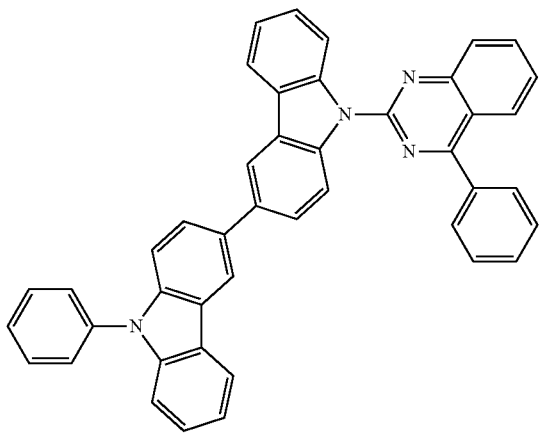
HT-1
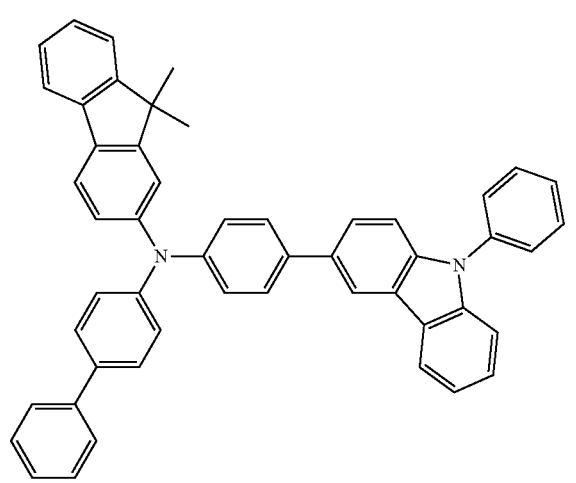
PD-1
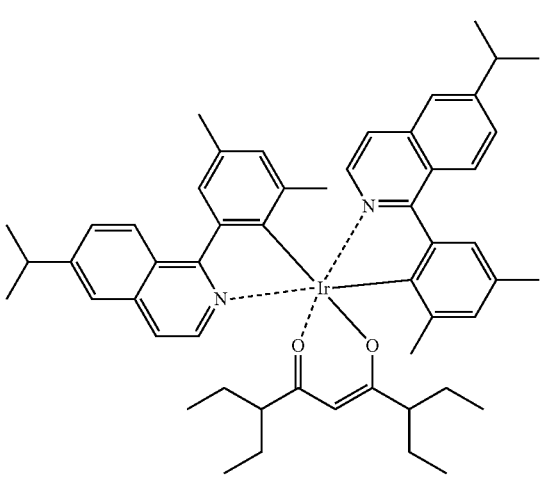

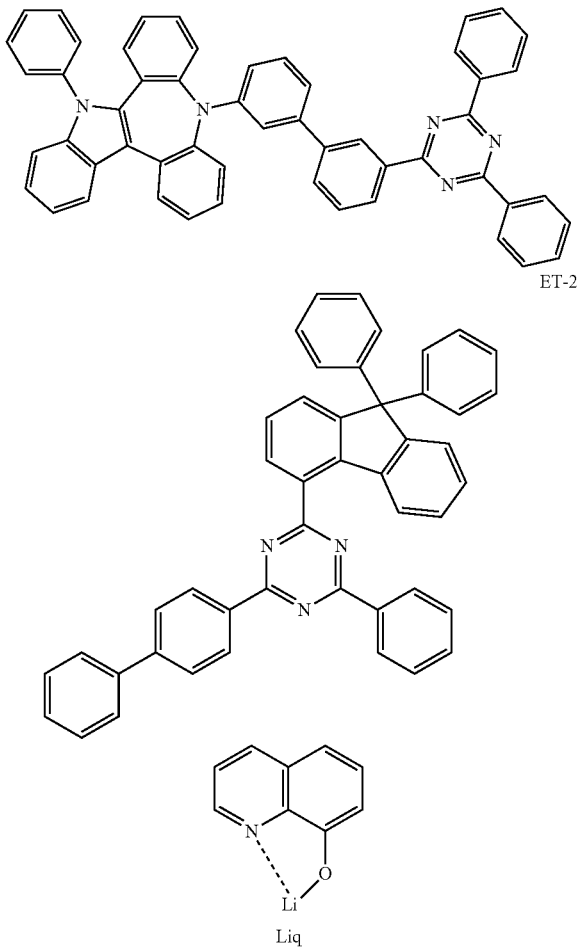

Example 1-1

Production of Organic EL Device

A glass substrate (25 mm×75 mm×1.1 mm) provided with an ITO transparent electrode (manufactured by GEO-MATEC Co., Ltd.) was ultrasonically cleaned in isopropyl alcohol for 5 minutes and then subjected to UV ozone cleaning for 30 minutes. The thickness of the ITO transparent electrode was 130 nm.

The cleaned glass substrate provided with the ITO transparent electrode was mounted on a substrate holder of a vacuum vapor deposition apparatus. First, Compound HT-1 and Compound HA (concentration: 3% by mass) were vapor co-deposited so as to cover the aforementioned transparent electrode, to form a hole injecting layer with a film thickness of 10 nm.

Subsequently, on this hole injecting layer, Compound HT-1 was vapor deposited to form a first hole transporting layer with a film thickness of 105 nm.

Subsequently, on this first hole transporting layer, Compound 1 obtained in Synthesis Example 1 was vapor deposited to form a second hole transporting layer with a film thickness of 85 nm.

Subsequently, on this second hole transporting layer, Compound PH-1 (host material) and Compound PD-1 (dopant material, concentration: 2% by mass) were vapor co-deposited to form a light emitting layer with a film thickness of 35 nm.

Subsequently, on this light emitting layer, Compound ET-1 (first electron transporting layer material) was vapor deposited to form a first electron transporting layer with a film thickness of 5 nm.

Subsequently, on this first electron transporting layer, Compound ET-2 (second electron transporting layer material) and Liq were vapor co-deposited to form a second electron transporting layer with a film thickness of 20 nm.

Subsequently, on this second electron transporting layer, Liq was vapor deposited to form an electron injecting electrode (cathode) with a film thickness of 1 nm.

Then, on this electron injecting electrode, metal Al was vapor deposited to form a metal cathode with a film thickness of 50 nm, thereby producing an organic EL device having the following layer structure.

An outline of the laminate configuration of this organic EL device is as follows. The numerals within the parentheses indicate a film thickness (unit: nm).

ITO (130)/HT-1:HA=97:3(mass ratio)(10)/HT-1(105)/
Compound 1 (85)/PH-1:PD-1=98:2(mass ratio)
(35)/ET-1(5)/ET-2:Liq=50:50(mass ratio)(20)/
Liq(1)/Al(50)

Measurement of Device Lifetime

The obtained organic EL device was subjected to DC drive at a current density of 50 mA/cm$^2$ at room temperature, a time until the luminance was reduced to 95% of the initial luminance was measured, and this was defined as 95% lifetime (LT95). The results are shown in Table 1.

Examples 1-2 to 1-4 and Comparative Example 1-1

Organic EL devices were produced in the same manner as in Example 1-1, except for using, as the second hole transporting material, each compound described in Table 1 in place of Compound 1. In addition, the device lifetime (95% lifetime, LT95) was measured in the same manner as in Example 1-1. The results are shown in Table 1.

TABLE 1

|  | Second hole transporting material | 95% lifetime (h) |
|---|---|---|
| Example 1-1 | Compound 1 | 86 |
| Example 1-2 | Compound 2 | 94 |
| Example 1-3 | Compound 3 | 82 |
| Example 1-4 | Compound 5 | 83 |
| Comparative Example 1-1 | Comparative Compound 1 | 54 |

From comparison of Example 1-1 with Comparative Example 1-1, it is noted that the device containing Compound 1 in the second hole transporting layer remarkably improves the device lifetime as compared with the device containing Comparative Compound 1.

From comparison of Examples 1-2 to 1-4 with Comparative Example 1-1, the same effect can be confirmed, too.

Compounds Used for the Second Hole Transporting Layer in the Following Examples 2-1 to 2-4

Compound 1
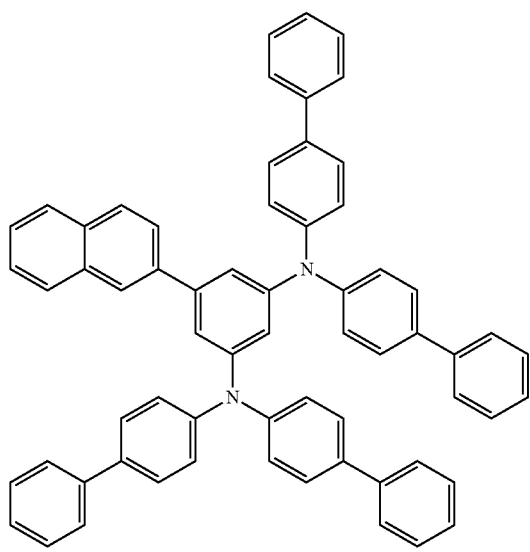
Compound 2
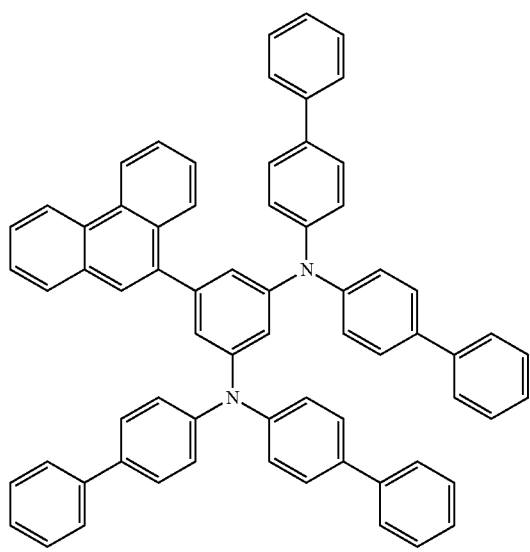
Compound 3
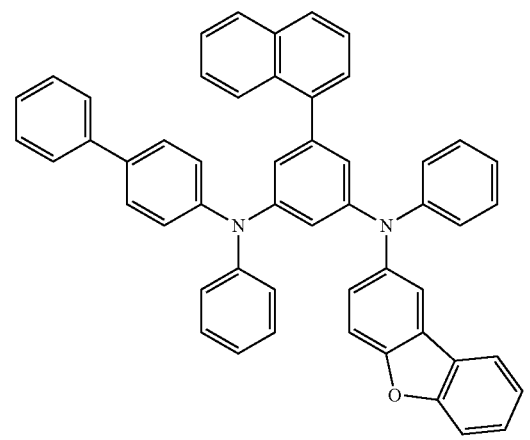
Compound 5
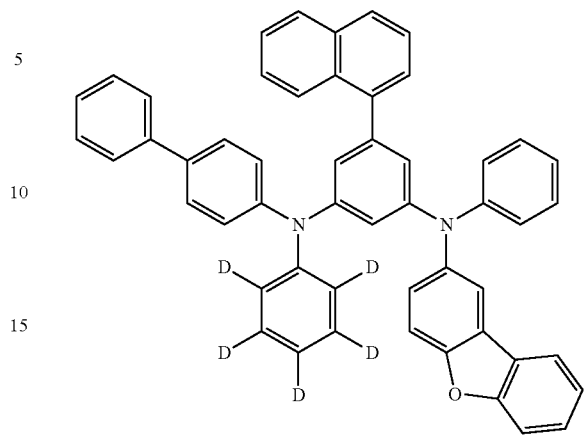
Comparative Compound Used for the Second Hole Transporting Layer of the Following Comparative Example 2-1
Comparative Compound 1
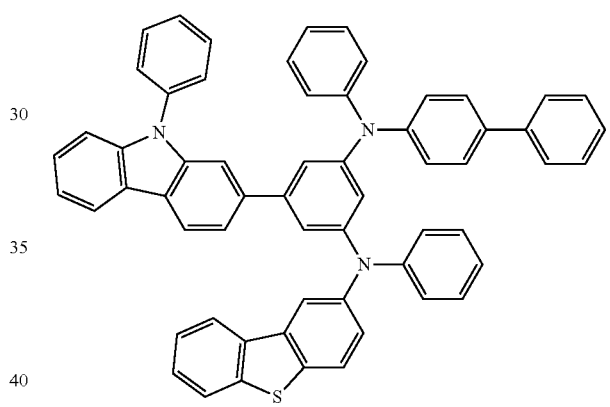
Other Compounds Used for Production of the Organic EL Devices of the Following Examples 1-1 to 1-4 and the Following Comparative Example 1-1
HT-1
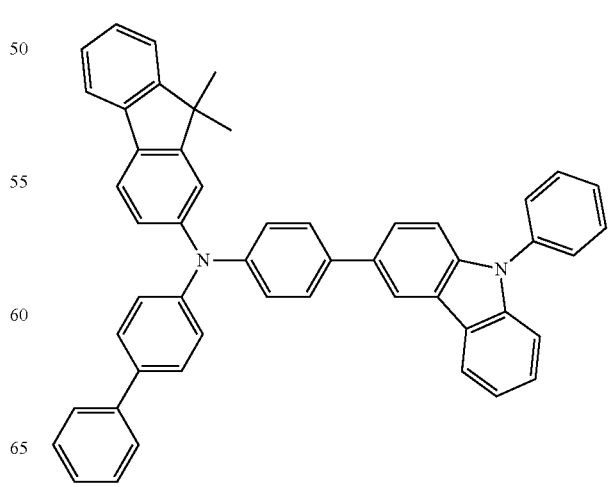

HA
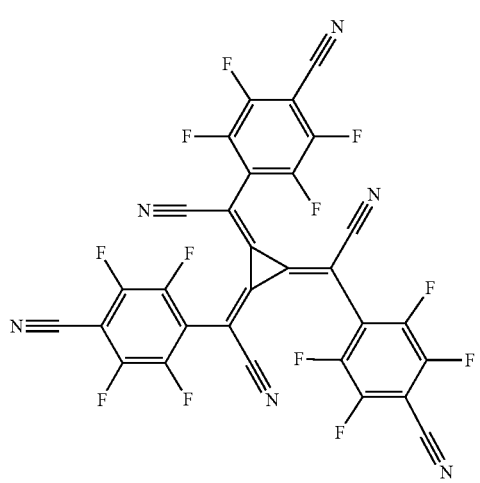

PH-2
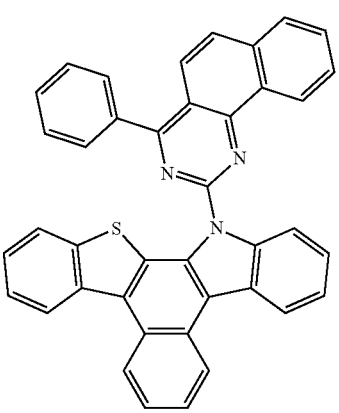

PD-1
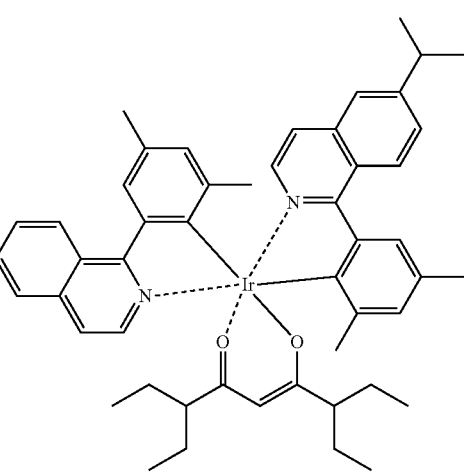

ET-1
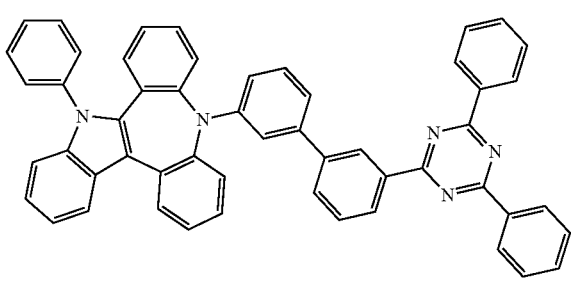

ET-2
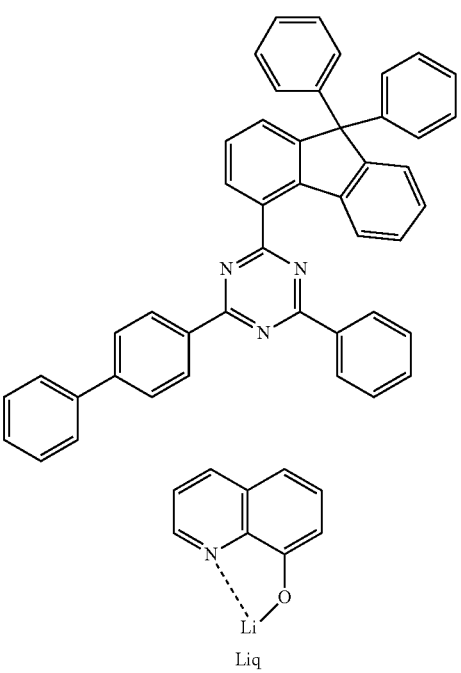

Liq

Example 2-1

An organic EL device was produced in the same manner as in Example 1-1, except for using Compound PH-2 (host material) in place of Compound PH-1 (host material). In addition, the device lifetime (95% lifetime, LT95) was measured in the same manner as in Example 1-1. The results are shown in Table 2.

An outline of the laminate configuration of this organic EL device is as follows. The numerals within the parentheses indicate a film thickness (unit: nm).

ITO(130)/HT-1:HA=97:3(mass ratio)(10)/HT-1(105)/
Compound 1 (85)/PH-2:PD-1=98:2(mass ratio)
(35)/ET-1(5)/ET-2:Liq=50:50(mass ratio)(20)/
Liq(1)/Al(50)

Examples 2-2 to 2-4 and Comparative Example 2-1

Organic EL devices were produced in the same manner as in Example 2-1, except for using, as the second hole transporting material, each compound described in Table 2 in place of Compound 1. In addition, the device lifetime (95% lifetime, LT95) was measured in the same manner as in Example 2-1. The results are shown in Table 1.

TABLE 2

|  | Second hole transporting material | 95% lifetime (h) |
| --- | --- | --- |
| Example 2-1 | Compound 1 | 240 |
| Example 2-2 | Compound 2 | 245 |
| Example 2-3 | Compound 3 | 237 |
| Example 2-4 | Compound 5 | 240 |
| Comparative Example 2-1 | Comparative Compound 1 | 162 |

From comparison of Example 2-1 with Comparative Example 2-1, it is noted that even in the case of using, as the host material, Compound PH-2 in place of Compound PH-1, the device containing Compound 1 in the second hole transporting layer remarkably improves the device lifetime as compared with the device containing Comparative Compound 1.

From comparison of Examples 2-2 to 2-4 with Comparative Example 2-1, the same effect can be confirmed, too.

Compounds Used for the Second Hole Transporting Layer in the Following Examples 3-1 and 3-2

Compound 4

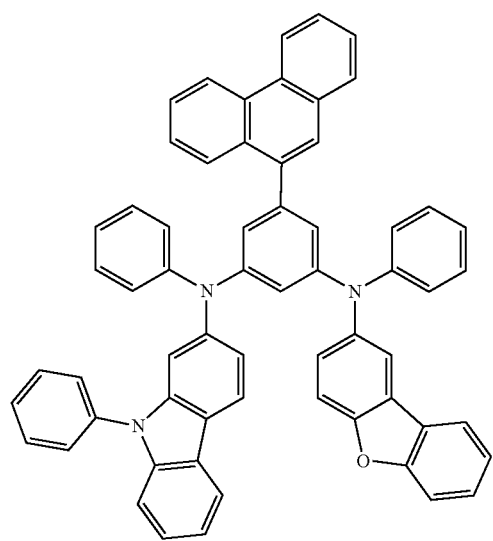

Compound 5

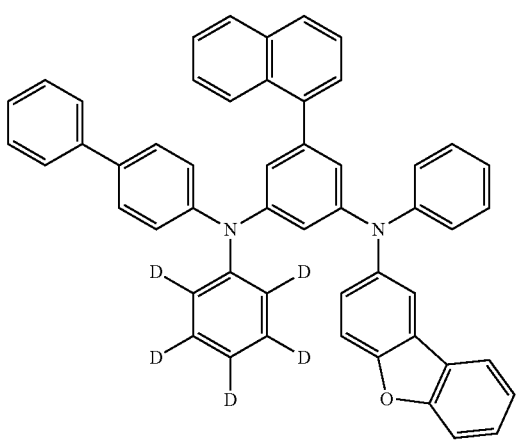

Comparative Compounds Used for the Second Hole Transporting Layer of the Following Comparative Examples 3-1 to 3-4

Comparative Compound 2

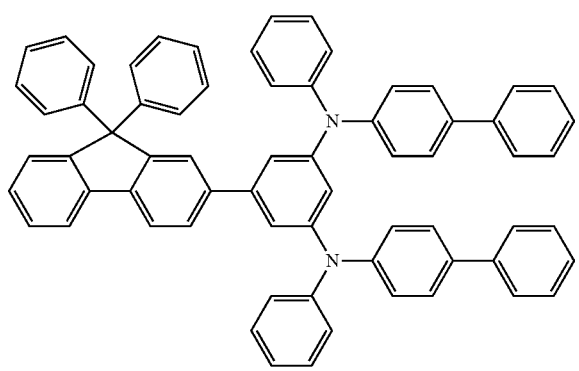

Comparative Compound 3

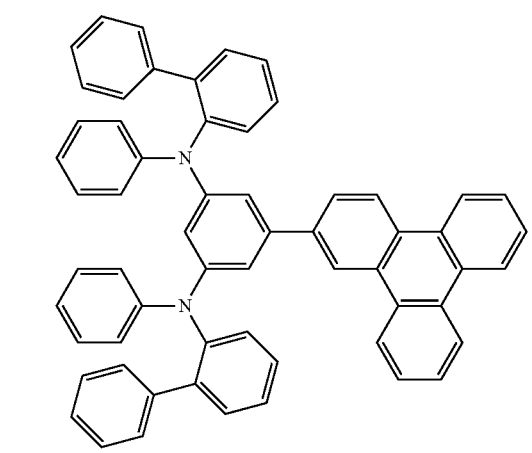

Comparative Compound 4

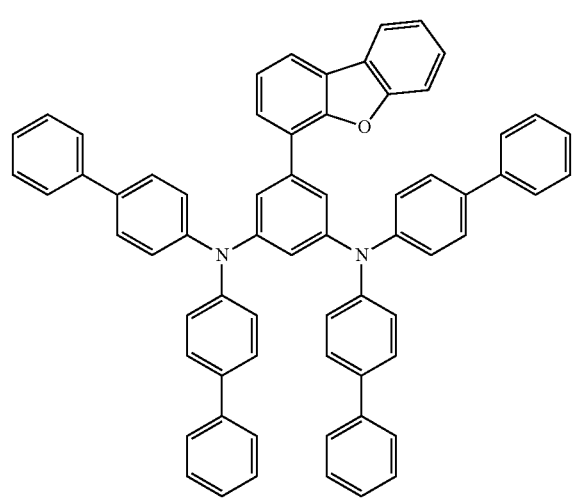

Comparative Compound 5
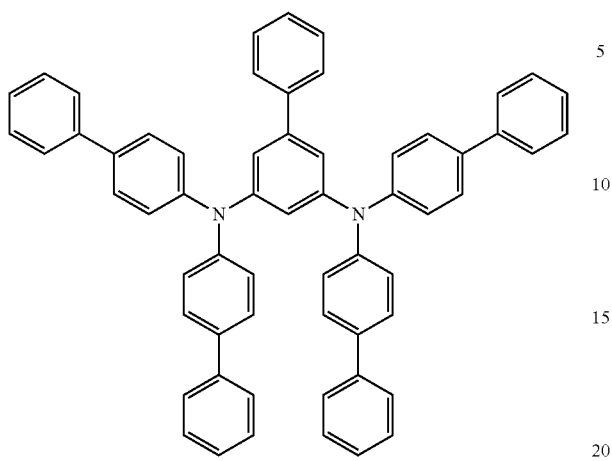
PH-2
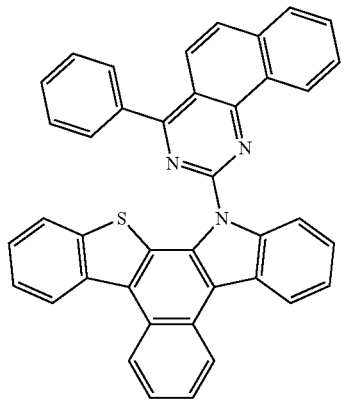 [SMILES: c1ccc(-c2nc(-n3c4ccccc4c4c5ccccc5c5c6ccccc6sc5c43)nc3c2ccc2ccccc23)cc1]
Other Compounds Used for Production of the Organic EL Devices of the Following Examples 3-1 and 3-2 and the Following Comparative Examples 3-1 to 3-4
HT-1
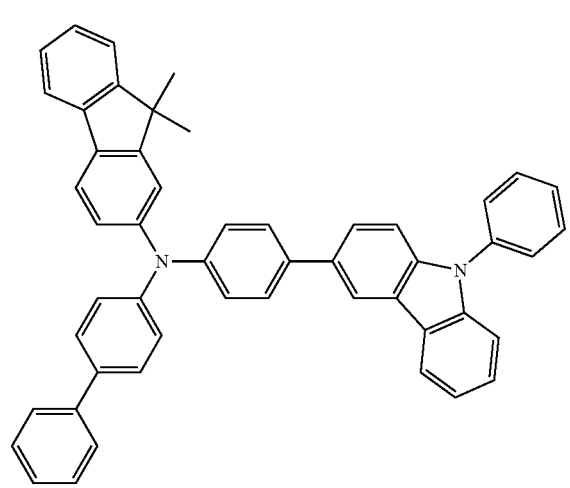
PD-2
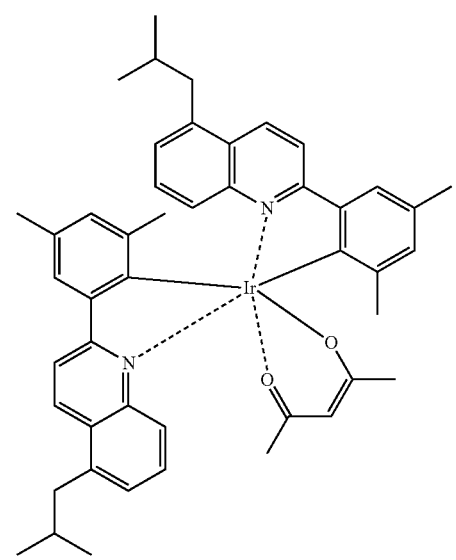
HA
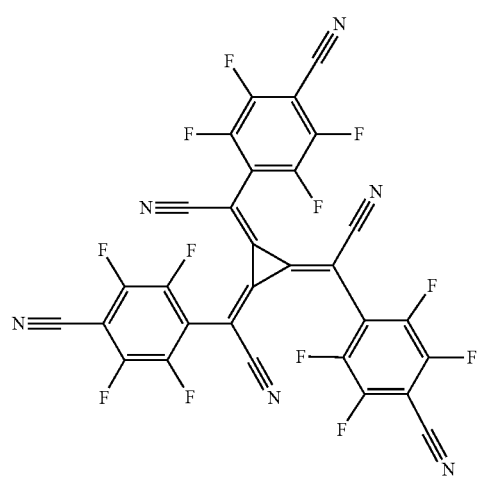
ET-1
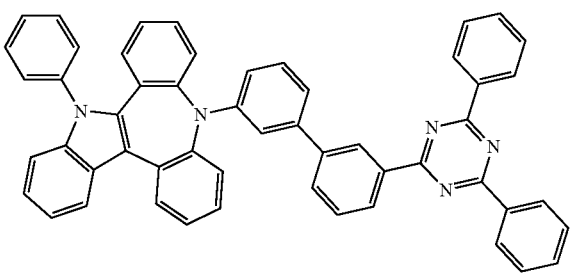

-continued

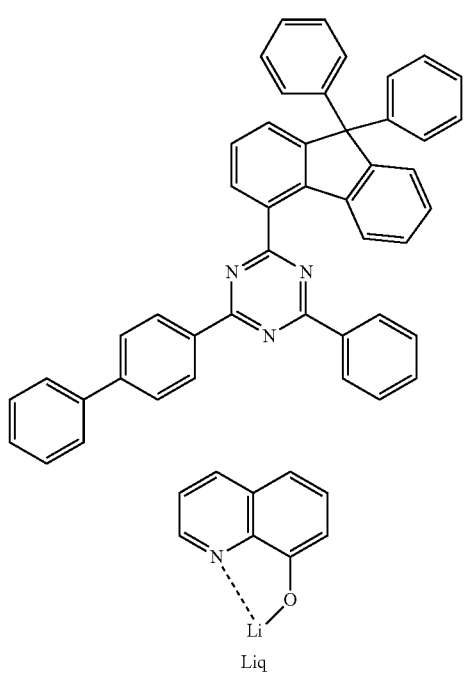

ET-2

Liq

Example 3-1

An organic EL device was produced in the same manner as in Example 2-1, except for using, as the second hole transporting material, Compound 4 in place of Compound 1 and using, Compound PD-2 (dopant material) in place of Compound PD-1 (dopant material).

An outline of the laminate configuration of this organic EL device is as follows. The numerals within the parentheses indicate a film thickness (unit: nm).

ITO(130)/HT-1:HA=97:3(mass ratio)(10)/HT-1(105)/
Compound 1 (85)/PH-2:PD-2=98:2(mass ratio)
(35)/ET-1(5)/ET-2:Liq=50:50(mass ratio)(20)/
Liq(1)/Al(50)

Measurement of Driving Voltage

A voltage when turning on electricity between the anode (ITO transparent electrode) and the metal cathode (metal Al) such that the electric current became 10 mA/cm$^2$ was measured. The results are shown in Table 3.

Examples 3-2 and Comparative Examples 3-1 to 3-4

Organic EL devices were produced in the same manner as in Example 3-1, except for using, as the second hole transporting material, each compound described in Table 3 in place of Compound 4. In addition, the voltage was measured in the same manner as in Example 3-1. The results are shown in Table 3.

TABLE 3

| | Second hole transporting material | Driving voltage (h) |
|---|---|---|
| Example 3-1 | Compound 4 | 3.86 |
| Example 3-2 | Compound 5 | 4.08 |
| Comparative Example 3-1 | Comparative Compound 2 | 5.01 |
| Comparative Example 3-2 | Comparative Compound 3 | 5.30 |
| Comparative Example 3-3 | Comparative Compound 4 | 5.38 |
| Comparative Example 3-4 | Comparative Compound 5 | 4.65 |

From comparison of Example 3-1 with Comparative Example 3-1, it is noted that the device containing Compound 1 in the second hole transporting layer is low in the driving voltage as compared with the device containing Comparative Compound 1.

From comparison of Example 3-1 with Comparative Examples 3-2 to 3-4 and comparison of Example 3-2 with Comparative Examples 3-1 to 3-4, the same effect can be confirmed, too.

Intermediate Synthesis Example 1

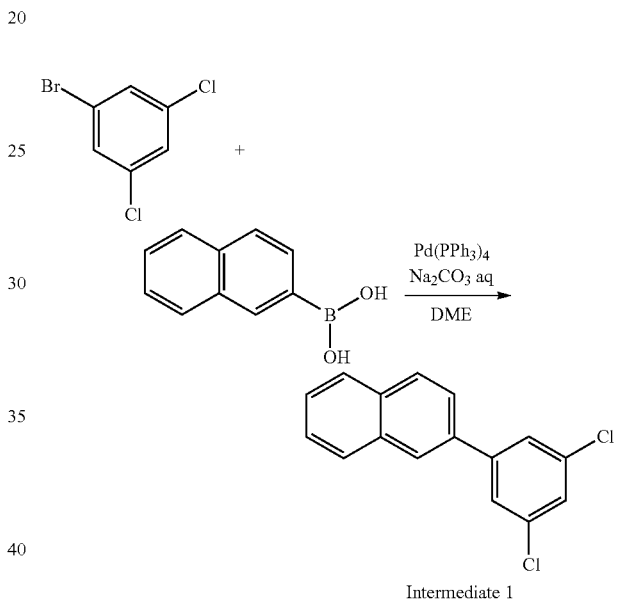

Intermediate 1

To a mixture of 1-bromo-3,5-dichlorobenzene (0.452 g, 2.00 mmol), 2-naphthaleneboronic acid (0.378 g, 2.20 mmol), tetrakis(triphenylphosphine)palladium(0) (0.046 g, 0.04 mmol), and dimethyl ether (20.0 mL), a sodium carbonate aqueous solution (1.5 mL, 2.00 mol/L) was added, and the contents were stirred under heating at 80° C. for 24 hours. To the resulting mixture, a saturated ammonium chloride aqueous solution was added, extraction with dichloromethane was performed, and an organic layer was concentrated under reduced pressure. The resulting residue was purified through column chromatography, to obtain 2-(3,5-dichlorophenyl)naphthalene (Intermediate 1). The yield was 81%.

Intermediate Synthesis Example 2

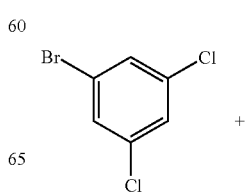

+

-continued

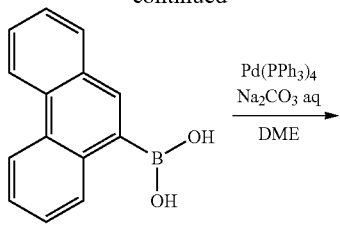

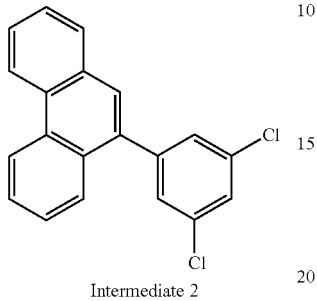

Intermediate 2

9-(3,5-Dichlorophenyl)phenanthrene (Intermediate 2) was obtained in the same method as in Intermediate Synthesis Example 1, except for using 9-phenanthreneboronic acid in place of 2-naphthaleneboronic acid. The yield was 90%.

Intermediate Synthesis Example 3

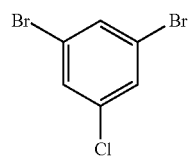

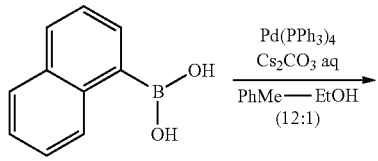

Intermediate 3

A mixture of 1,3-dibromo-5-chlorobenzene (3.510 g, 13.0 mmol), 1-naphthaleneboronic acid (1.720 g, 10.0 mmol), tetrakis(triphenylphosphine)palladium(0) (0.231 g, 0.2 mmol), cesium carbonate (1.590 g, 15.0 mmol), water (10.0 mL), toluene (60.0 mL), and ethanol (5.0 mL) was stirred under heating at 80° C. for 6 hours. To the resulting mixture, toluene was added to perform extraction, and after washing, an organic layer was concentrated under reduced pressure. The resulting residue was purified through column chromatography, to obtain 1-(3-bromo-5-chlorophenyl)naphthalene (Intermediate 3). The yield was 75%.

Intermediate Synthesis Example 4

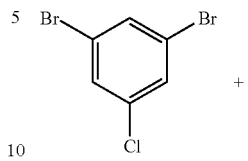

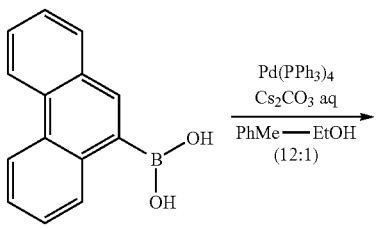

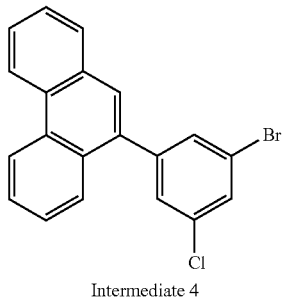

Intermediate 4

9-(3-bromo-5-chlorophenyl)phenanthrene (Intermediate 4) was obtained in the same method as in Intermediate Synthesis Example 3, except for using 9-phenanthreneboronic acid in place of 1-naphthaleneboronic acid. The yield was 81%.

Intermediate Synthesis Example 5

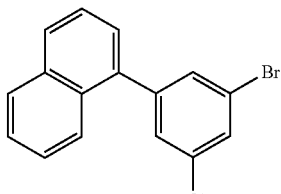

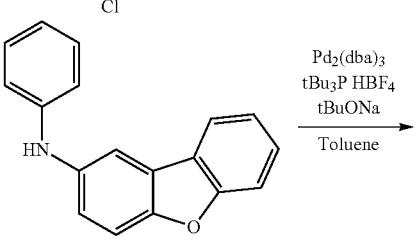

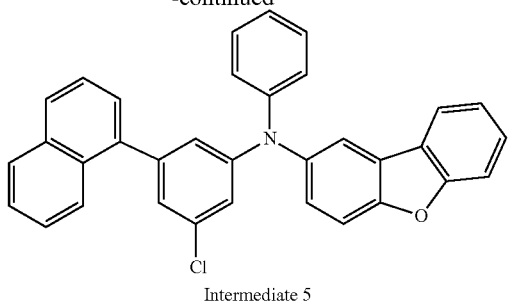

Intermediate 5

A mixture of 1-(3-bromo-5-chlorophenyl)naphthalene (3.490 g, 11.0 mmol), N-phenyl-dibenzofuranamine (2.850 g, 11.0 mmol), tris(dibenzylideneacetone)dipalladium(0) (0.302 g, 0.33 mmol), tri-t-butylphosphonium tetrafluoroborate (0.383 g, 1.32 mmol), sodium-t-butoxide (1.480 g, 15.4 mmol), and toluene (110.0 mL) was stirred under heating at 110° C. for 6 hours in an argon atmosphere. The resulting mixture was filtered and then concentrated under reduced pressure. The resulting residue was purified through column chromatography, to obtain Intermediate 5. The yield was 69%.

Intermediate Synthesis Example 6

Intermediate 6

Intermediate 6 was obtained in the same method as in the synthesis of Intermediate 5, except for using 9-(3-bromo-5-chlorophenyl)phenanthrene in place of 1-(3-bromo-5-chlorophenyl)naphthalene. The yield was 72%.

Synthesis Example 1

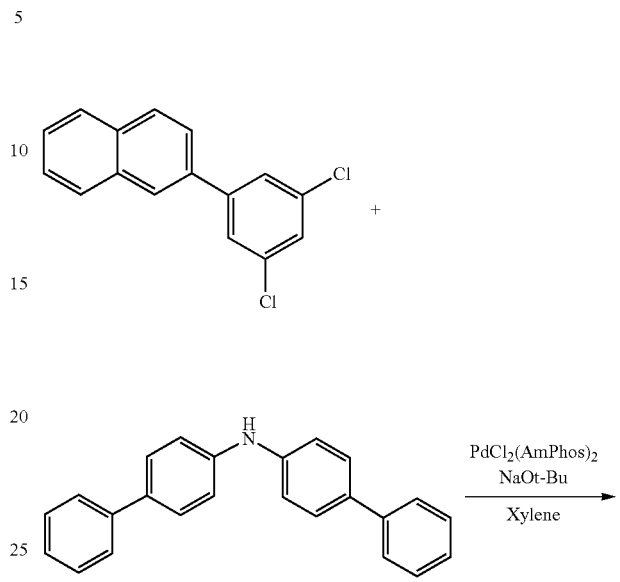

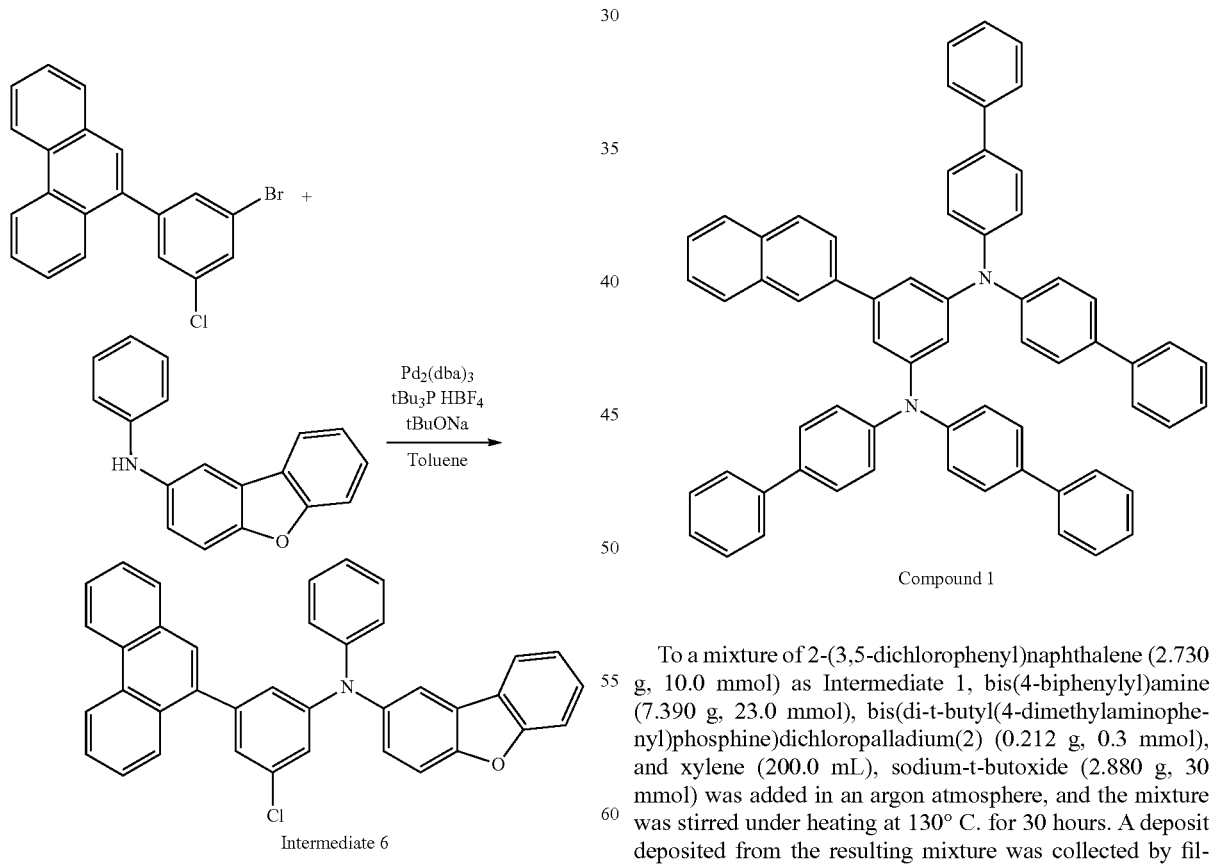

Compound 1

To a mixture of 2-(3,5-dichlorophenyl)naphthalene (2.730 g, 10.0 mmol) as Intermediate 1, bis(4-biphenylyl)amine (7.390 g, 23.0 mmol), bis(di-t-butyl(4-dimethylaminophenyl)phosphine)dichloropalladium(2) (0.212 g, 0.3 mmol), and xylene (200.0 mL), sodium-t-butoxide (2.880 g, 30 mmol) was added in an argon atmosphere, and the mixture was stirred under heating at 130° C. for 30 hours. A deposit deposited from the resulting mixture was collected by filtration and purified through column chromatography, to obtain 0.41 g of a solid.

As a result of mass spectrum analysis, the obtained product (m/e=842 relative to the molecular weight of 842.37) was identified as Compound 1. The yield was 62%.

Synthesis Example 2

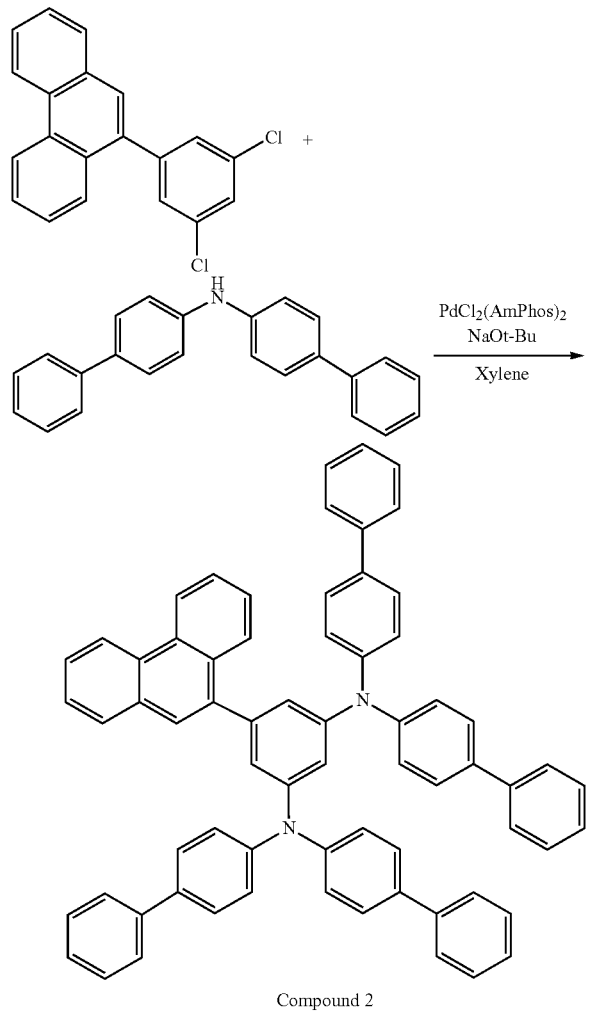

Compound 2

A solid was obtained in the same method as in Synthesis Example 1, except for using 9-(3,5-dichlorophenyl) phenanthrene as Intermediate 2 in place of 2-(3,5-dichlorophenyl)naphthalene as Intermediate 1:

As a result of mass spectrum analysis, the obtained product (m/e=892 relative to the molecular weight of 892.38) was identified as Compound 2. The yield was 59%.

Synthesis Example 3

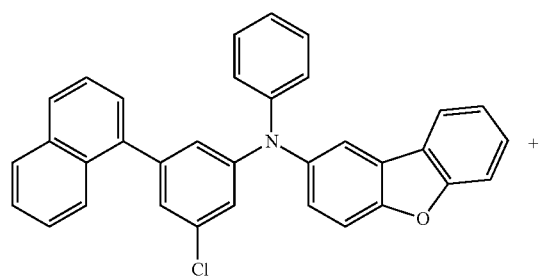

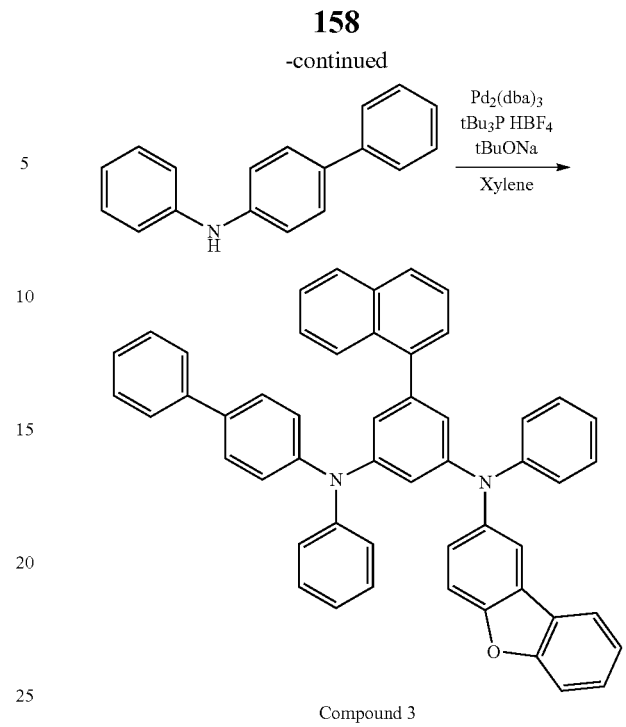

Compound 3

A mixture of Intermediate 5 (2.640 g, 5.32 mmol), N-phenyl-4-biphenylamine (1.436 g, 5.85 mmol), tri-t-butylphosphonium tetrafluoroborate (0.185 g, 0.639 mmol), tris(dibenzylideneacetone)dipalladium(0) (0.146 g, 0.016 mmol), sodium-t-butoxide (0.767 g, 7.98 mmol), and xylene (53.0 mL) was stirred under heating at 140° C. for 6 hours in an argon atmosphere. The resulting mixture was extracted with toluene, and the resulting residue was purified through column chromatography, to obtain a solid.

As a result of mass spectrum analysis, the obtained product (m/e=704 relative to the molecular weight of 704.28) was identified as Compound 3. The yield was 83%.

Synthesis Example 4

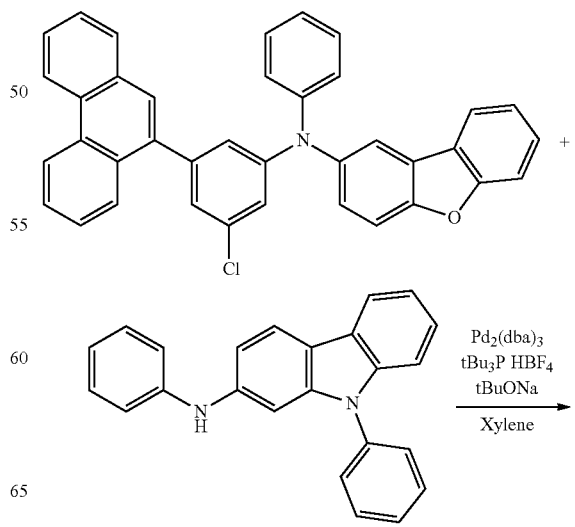

-continued

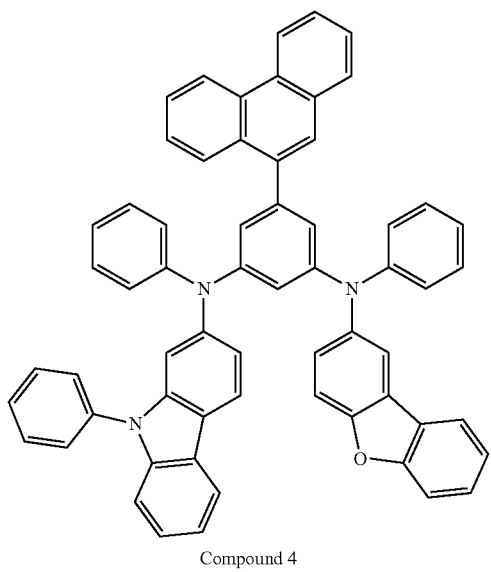

Compound 4

A solid was obtained in the same method as in Synthesis Example 3, except for using Intermediate 6 in place of Intermediate 5 and N-phenyl-9-phenylcarbazole-2-amine having been synthesized by a method already known by literature in place of N-phenyl-4-biphenylamine.

As a result of mass spectrum analysis, the obtained product (m/e=843 relative to the molecular weight of 843.32) was identified as Compound 4. The yield was 59%.

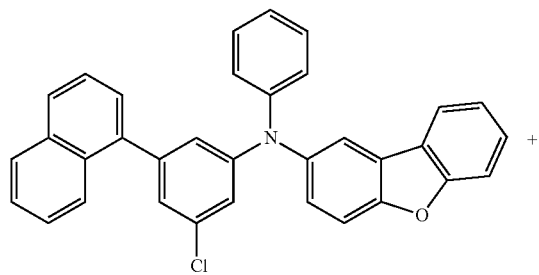

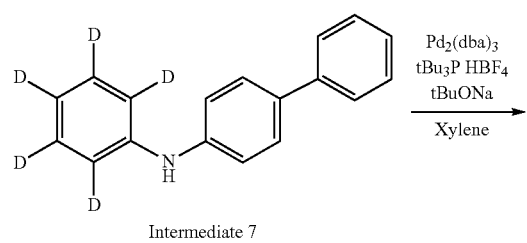

Intermediate 7

-continued

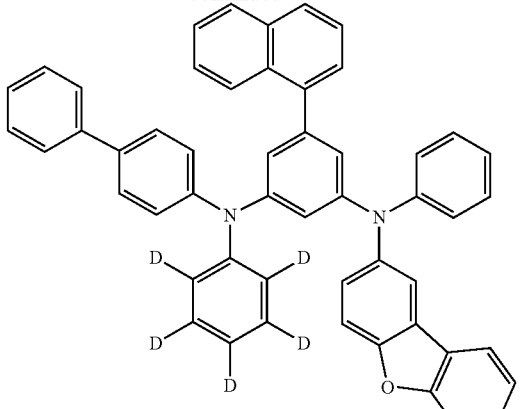

Compound 5

A solid was obtained in the same method as in Synthesis Example 3, except for using Intermediate 7 in place of N-phenyl-4-biphenylamine.

As a result of mass spectrum analysis, the obtained product (m/e=709 relative to the molecular weight of 709.31) was identified as Compound 5. The yield was 83%.

REFERENCE SIGNS LIST 1, 11: Organic EL device
2: Substrate
3: Anode
4: Cathode
5: Light emitting layer
6: Hole transporting zone (hole transporting layer)
6a: First hole transporting layer
6b: Second hole transporting layer
7: Electron transporting zone (electron transporting layer)
7a: First electron transporting layer
7b: Second electron transporting layer
10, 20: Light emitting unit

The invention claimed is:
1. A compound of formula (1):

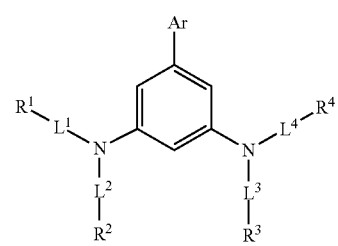

(1)

wherein,
$R^1$ to $R^4$ are each independently selected from the group consisting of a substituted or unsubstituted aryl group having 6 to 30 ring carbon atoms and a substituted or unsubstituted heteroaryl group having 5 to 30 ring atoms,
wherein when substituted, the substituents on $R^1$ to $R^4$ are each independently selected from the group consisting of an alkyl group having 1 to 30 carbon atoms, a cycloalkyl group having 3 to 30 carbon atoms, an aryl group having 6 to 30 ring carbon atoms, an alkoxy group having 1 to 30 carbon atoms, an aryloxy group having 6 to 30 ring carbon atoms, a mono-, di- or tri-substituted silyl group having a substituent selected from an alkyl group having 1 to 30 carbon atoms, and an aryl group having 6 to 30 ring carbon atoms, and a heteroaryl group having 5 to 30 ring atoms, $L^1$ to $L^4$ are each independently selected from the group consisting of a single bond and a substituted or unsubstituted arylene group having 6 to 30 ring carbon atoms, $R^1$ or $L^1$ does not bond to $R^2$ or $L^2$ to form a ring structure, and $R^3$ or $L^3$ does not bond to $R^4$ or $L^4$ to form a ring structure, $R^1$ does not bond to $R^3$ to form a ring structure, $R^1$ does not bond to $R^4$ to form a ring structure, $R^2$ does not bond to $R^3$ to form a ring structure, and $R^2$ does not bond to $R^4$ to form a ring structure, and Ar is formula (A) or (B):

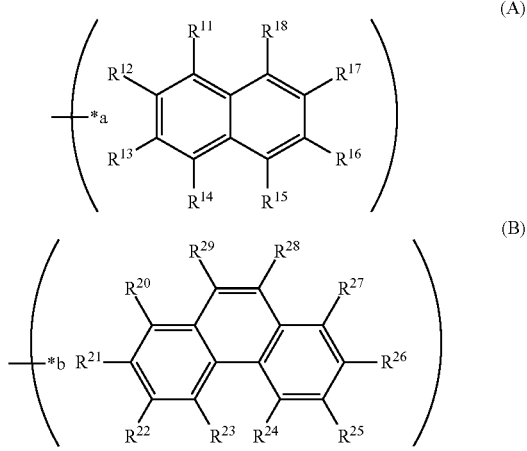

wherein, $R^{11}$ to $R^{18}$ and $R^{20}$ to $R^{29}$ are each a hydrogen atom provided that one selected from $R^{11}$ to $R^{18}$ is a single bond bonding to *a, and one selected from $R^{20}$ to $R^{29}$ is a single bond bonding to *b, and Ar does not bond to a benzene ring bonding to Ar to form a ring structure.

2. The compound according to claim 1, wherein $R^1$ to $R^4$ are each independently selected from the group consisting of a substituted or unsubstituted phenyl group, a substituted or unsubstituted biphenylyl group, a substituted or unsubstituted terphenylyl group, a substituted or unsubstituted fluorenyl group, a substituted or unsubstituted dibenzofuranyl group, a substituted or unsubstituted dibenzothiophenyl group, and a substituted or unsubstituted carbazolyl group.

3. The compound according to claim 2, wherein in the substituted or unsubstituted biphenylyl group, the biphenylyl group is a p-, o-, or m-biphenylyl group.

4. The compound according to claim 2, wherein in the substituted or unsubstituted biphenylyl group, the biphenylyl group is a p-biphenylyl group.

5. The compound according to claim 2, wherein the substituted or unsubstituted terphenylyl group is a 1,1':4',1''-terphenyl-4-yl group, a 1,1':3',1''-terphenyl-4-yl group, or a 1,1':3',1''-terphenyl-2-yl group.

6. The compound according to claim 2, wherein in the substituted or unsubstituted fluorenyl group, the fluorenyl group is a 1-, 2-, 3-, or 4-fluorenyl group.

7. The compound according to claim 2, wherein in the substituted or unsubstituted fluorenyl group, the fluorenyl group is a 2-fluorenyl group or a 4-fluorenyl group.

8. The compound according to claim 2, wherein in the substituted or unsubstituted dibenzofuranyl group, the dibenzofuranyl group is a 2- or 3-dibenzofuranyl group.

9. The compound according to claim 2, wherein in the substituted or unsubstituted dibenzofuranyl group, the dibenzofuranyl group is a 2-dibenzofuranyl group.

10. The compound according to claim 2, wherein in the substituted or unsubstituted dibenzothiophenyl group, the dibenzothiophenyl group is a 2- or 3-dibenzothiophenyl group.

11. The compound according to claim 2, wherein in the substituted or unsubstituted dibenzothiophenyl group, the dibenzothiophenyl group is a 2-dibenzothiophenyl group.

12. The compound according to claim 2, wherein in the substituted or unsubstituted carbazolyl group, the carbazolyl group is a 1-, 2-, 3-, or 4-carbazolyl group.

13. The compound according to claim 2, wherein in the substituted or unsubstituted carbazolyl group, the carbazolyl group is a 2- or 3-carbazolyl group.

14. The compound according to claim 2, wherein in the substituted or unsubstituted carbazolyl group, the carbazolyl group is a 2-carbazolyl group.

15. The compound according to claim 1, wherein Ar is the formula (A), and $R^{11}$ or $R^{12}$ is a single bond bonding to *a.

16. The compound according to claim 1, wherein Ar is the formula (B), and one selected from $R^{20}$ to $R^{23}$ and $R^{29}$ is a single bond bonding to *b.

17. The compound according to claim 1, wherein Ar is the formula (B), and $R^{29}$ is a single bond bonding to *b.

18. The compound according to claim 1, wherein $L^1$ to $L^4$ are a single bond.

19. The compound according to claim 1, wherein the compound of formula (1) comprises at least one deuterium atom.

20. A material for organic electroluminescent devices comprising the compound according to claim 1.

21. An organic electroluminescent device comprising a cathode, an anode, and organic layers between the cathode and the anode, wherein the organic layers comprise a light emitting layer, and at least one layer of the organic layers comprises the compound according to claim 1.

22. The organic electroluminescent device according to claim 21, wherein the organic layer comprises a hole transporting zone between the anode and the light emitting layer, and the hole transporting zone comprises the compound.

23. The organic electroluminescent device according to claim 21, wherein the hole transporting zone comprises a first hole transporting layer on the anode side and a second hole transporting layer on the cathode side, and the first hole transporting layer, the second hole transporting layer, or both of them comprise the compound.

24. The organic electroluminescent device according to claim 23, wherein the first hole transporting layer comprises the compound.

25. The organic electroluminescent device according to claim 23, wherein the second hole transporting layer comprises the compound.

26. The organic electroluminescent device according to claim 25, wherein the second hole transporting layer is adjacent to the light emitting layer.

27. The organic electroluminescent device according to claim 21, wherein the light emitting layer contains a fluorescent light emitting material.

* * * * *